(12) United States Patent
Ogino et al.

(10) Patent No.: US 6,846,835 B2
(45) Date of Patent: Jan. 25, 2005

(54) ESTER DERIVATIVES

(75) Inventors: Yoshio Ogino, Tsukuba (JP); Hideki Kurihara, Tsukuba (JP); Kenji Matsuda, Tsukuba (JP); Tomoshige Numazawa, Tsukuba (JP); Norikazu Otake, Tsukuba (JP); Kazuhito Noguchi, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/332,617

(22) PCT Filed: Jul. 10, 2001

(86) PCT No.: PCT/JP01/05987
§ 371 (c)(1),
(2), (4) Date: Jan. 10, 2003

(87) PCT Pub. No.: WO02/04402
PCT Pub. Date: Jan. 17, 2002

(65) Prior Publication Data
US 2003/0191316 A1 Oct. 9, 2003

(30) Foreign Application Priority Data
Jul. 11, 2000 (JP) .......................................... 2000-210591

(51) Int. Cl.⁷ .................. A61K 31/445; A61K 31/4465; C07D 221/02; C07D 211/04
(52) U.S. Cl. ....................... 514/317; 514/318; 546/192; 546/194; 546/236
(58) Field of Search ................................. 546/192, 194, 546/236; 514/317, 318

(56) References Cited

U.S. PATENT DOCUMENTS

| 3,903,094 | A  | * | 9/1975  | Witten et al. | ............... | 546/204 |
| 6,482,837 | B1 | * | 11/2002 | Wood          | ............... | 514/315 |
| 6,484,837 | B1 | * | 11/2002 | Buell et al.  | ............... | 180/225 |

FOREIGN PATENT DOCUMENTS

| EP | 140434    | 5/1985 |
| EP | 0 309 424 | 3/1989 |
| FR | 1352332   | 1/1964 |
| JP | 1-131145  | 5/1989 |
| WO | 98/21183  | 5/1998 |

OTHER PUBLICATIONS

V. Tumiatti et al., "Affinity and selectivity at M₂ and M₃ muscarinic receptor subtypes of cyclic and open oxygenated analogues of 4–DAMP (*)", Farmaco, vol. 47, No. 9, pp. 1133–1147, 1992.

* cited by examiner

Primary Examiner—Rita Desai
(74) Attorney, Agent, or Firm—Wenderoth, Lind & Ponack, L.L.P.

(57) ABSTRACT

This invention relates to compounds which exhibit selective muscarinic $M_3$ receptor antagonism, have little side effects, are suitable for inhalation therapy and are useful as treating agents of respiratory system diseases, of the general formula (I);

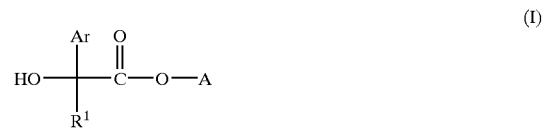

[in which A signifies a group expressed by a formula ($a_0$) or ($b_0$);

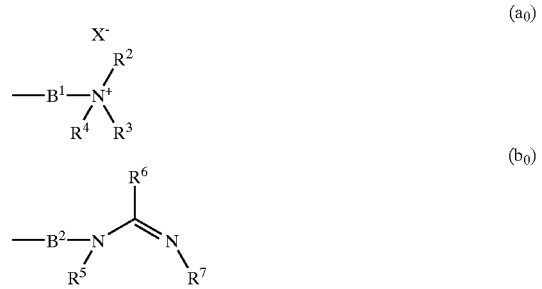

Ar signifies optionally substituted aryl or heteroaryl; $B^1$ and $B^2$ signify aliphatic hydrocarbon; $R^1$ signifies fluorine-substituted cycloalkyl; $R^2$, $R^3$ and $R^4$ signify lower alkyl, single bond or alkylene bonded to $B^1$, or $R^2$ and $R^3$ are united to signify alkylene; $R^5$ and $R^7$ signify hydrogen, lower alkyl, or a single bond or alkylene bonded to $B^2$; $R^6$ signifies hydrogen, lower alkyl or a group expressed as —N($R^8$)$R^9$; and $X^-$ signifies an anion].

32 Claims, No Drawings

ESTER DERIVATIVES

This application is a U.S. National Stage of International Application No. PCT/JP01/05987 filed Jul. 10, 2001.

TECHNICAL FIELD

This invention relates to novel ester derivatives, processes for preparing them, pharmaceutics containing them and their use as medicines, especially for the treatment of various diseases of the respiratory system.

BACKGROUND ART

Antagonism to muscarinic receptors are known to cause bronchodilation, gastrointestinal hypanakinesis, gastric hyposecretion, dry mouth, mydriasis, suppression of bladder contraction, hypohydrosis, tachycardia and the like [cf. "*Basic and Clinical Pharmacology*, 4th ed., (APPLETON & LANGE), pp.83–92, (1989); and *Drug News & Perspective*, 5(6), pp.345–352 (1992)].

It has been made clear through recent studies that there are at least three subtypes of muscarine receptors ($M_1$ receptors, $M_2$ receptors and $M_3$ receptors); which receptors are present in tissues or organs at different distribution patterns. $M_1$ receptors are present mainly on the brain; $M_2$ receptors, on the heart; and $M_3$ receptors, on the smooth muscles and glandular tissues. Whereas, all of the large number of compounds heretofore known to exhibit antagonism to muscarinic receptors antagonize these three subtypes of muscarinic receptors non-selectively. Consequently, in oral administration of these compounds as therapeutic or prophylactic agents for treatment of diseases of, for example, the respiratory system, in addition to such side effects as dry mouth, nausea and mydriasis, serious side effects associated with the central nervous system, such as dementia, induced particularly by $M_1$ receptors and those associated with the heart, such as tachycardia caused by $M_2$ receptors present problems.

Currently, administration by inhalation of non-selective muscarine antagonists as therapeutic or prophylactic agents for respiratory diseases is clinically applied. However, those medicines are subject to the problems that durability of their action is short and their inhalation plural times per day is necessary, and also that they have such side effects as tachycardia and dry mouth attributable to the non-selectivity of said receptors.

As compounds having a structure resembling that of the compounds of the present invention, for example, those described in JP-Hei 1 (1989)-131145A or in *Farmaco*, Vol.47, No.9, pp.1133–1147 (1992) can be cited, which, however, neither concretely disclose nor suggest the compounds of the present invention.

DISCLOSURE OF THE INVENTION

The object of the present invention is to provide treating agents of diseases associated with muscarine $M_3$ receptors, which exhibit highly selective antagonism to muscarine $M_3$ receptors but little side effect and hence are safe and effective.

We have discovered that the compounds represented by a general formula (I):

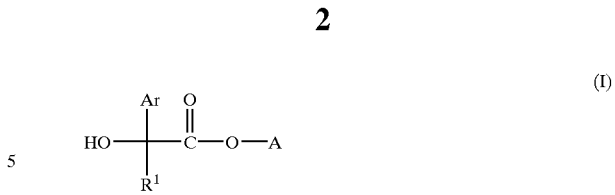

[in which A signifies a group expressed by a formula ($a_0$) or ($b_0$);

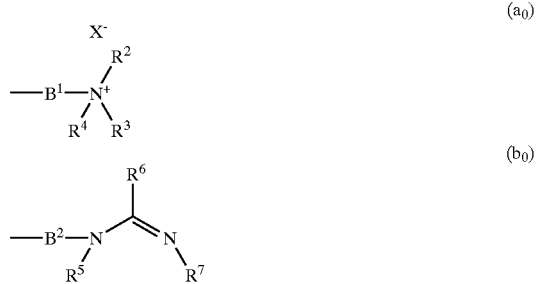

Ar signifies aryl or heteroaryl optionally having substituent(s) selected from a group consisting of halogen, lower alkyl, lower alkenyl and lower alkoxy; $B^1$ and $B^2$ signify, independently of each other, straight chain, branched chain and/or cyclic portion-containing $C_2$–$C_{10}$ saturated or unsaturated aliphatic hydrocarbon which may have hyroxyl group(s) and/or be interrupted with nitrogen atom(s); $R^1$ signifies a fluorine-substituted $C_4$–$C_6$ cycloalkyl optionally having hydroxyl group(s); $R^2$, $R^3$ and $R^4$ signify, either independently of each other, a lower alkyl optionally having substituent(s) selected from a group consisting of phenyl and cycloalkyl, or $R^2$ and $R^3$ together signify a $C_2$–$C_5$ alkylene which may be interrupted with oxygen; or $R^4$ signifies a single bond or a $C_1$–$C_3$ alkylene binding to a bindable optional site on $B^1$; $R^5$ signifies hydrogen or a lower alkyl optionally having substituent(s) selected from a group consisting of phenyl and cycloalkyl and $R^7$ signifies hydrogen or a lower alkyl, or either one of $R^5$ and $R^7$ signifies a single bond or a $C_1$–$C_3$ alkylene binding to a bindable optional site on $B^2$; $R^6$ signifies hydrogen, lower alkyl or a group represented by —N($R^8$)$R^9$; $R^8$ and $R^9$ signify, independently of each other, hydrogen or lower alkyl; and $X^-$ signifies an anion] exhibit highly selective antagonism to muscarine $M_3$ receptors and hence have little side effect and are safe. Furthermore, they also exhibit excellent pharmacological effect and durability of the action in inhalation therapy. Accordingly, we found the compounds very useful for treating various diseases associated with muscarine $M_3$ receptors, e.g., respiratory diseases such as chronic obstructive pulmonary diseases, chronic bronchitis, asthma, chronic respiratory tract obstruction, fibroid lung, pulmonary emphysema and rhinitis. The present invention is whereupon completed.

This invention relates to the compounds represented by the general formula (I) or salts thereof, and their production processes and their utility.

The invention furthermore relates to the compounds which are intermediate products of the compounds represented by the general formula (I) and exhibit highly selective antagonism to muscarine $M_3$ receptors, i.e., the compounds represented by a general formula (II)

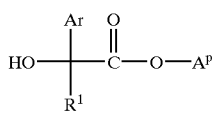

(II)

[in which $A^p$ signifies a group represented by a formula $(a_{p0})$ or $(b_{p0})$]

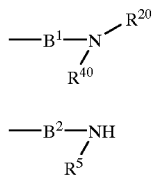

$R^{20}$ signifies hydrogen or a lower alkyl optionally having substituent(s) selected from a group consisting of phenyl and cycloalkyl; $R^{40}$ signifies lower alkyl which may have substituent(s) selected from a group consisting of phenyl and cycloalkyl, or a single bond or a $C_1$–$C_3$ alkylene group binding to a bindable optional site on $B^1$; and Ar, $B^1$, $B^2$, $R^1$ and $R^5$ have the earlier given significations] and salts thereof.

Hereinafter we will explain the meanings of the terms used in this specification and describe the present invention in further details.

"Halogen" means fluorine, chlorine, bromine and iodine atoms.

"Lower alkyl" means $C_1$–$C_6$ straight chain or branched alkyl groups, examples of which include methyl, ethyl, propyl, isopropyl, butyl, isobutyl, sec-butyl, tert-butyl, pentyl, isopentyl, hexyl and isohexyl groups.

"Lower alkenyl" means $C_2$–$C_6$ straight chain or branched alkenyl groups, examples of which include vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl and 4-pentenyl groups.

"Lower alkoxy" means $C_1$–$C_6$ straight chain or branched alkoxy groups or $C_1$–$C_3$ alkylenedioxy groups, examples of which include methoxy, ethoxy, propoxy, isopropoxy, butoxy, sec-butoxy, isobutoxy, tert-butoxy, pentyloxy, isopentyloxy, hexyloxy, isohexyloxy, methylenedioxy, ethylenedioxy and trimethylenedioxy groups.

"Aryl" means $C_6$–$C_{11}$ aryl groups, examples of which include phenyl and naphthyl groups.

"Heteroaryl" means 5- or 6-membered monocyclic heteroaryl groups containing one or two same or different hetero atoms selected from a group consisting of nitrogen, oxygen and sulfur atoms, or condensed ring-type heteroaryl groups formed by condensation of one of said monocyclic heteroaryl groups with one of aforesaid aryl groups, or by mutual condensation of same or different monocyclic heteroaryl groups as above-explained, examples of which include 2-pyridyl, 3-pyridyl, 4-pyridyl, 2-thiazolyl, 4-thiazolyl, 2-thienyl, 3-thienyl, 1-imidazolyl, 2-imidazolyl, 4-imidazolyl, 3-pyrazolyl, 4-pyrazolyl, 2-furyl, 3-furyl, 2-pyrrolyl, 3-pyrrolyl, 2-pyrimidinyl, 4-pyrimidinyl, 5-pyrimidinyl, 2-pyrazinyl, 3-pyridazinyl, 4-pyridazinyl, 2-quinolinyl, 2-benzothienyl and 2-indolyl groups.

"Straight chain, branched chain and/or cyclic portion-containing $C_2$–$C_{10}$ saturated or unsaturated aliphatic hydrocarbon which may have hydroxyl group(s) and/or be interrupted with nitrogen atom(s)" means straight chain, branched chain and/or cyclic portion-containing $C_2$–$C_{10}$ saturated or unsaturated aliphatic hydrocarbon groups which have 1, 2 or more, preferably 1, hydroxyl group(s) on optional, substitutable position(s) on such saturated or unsaturated aliphatic hydrocarbon group or do not have them and, furthermore, which are interrupted with 1, 2 or more, preferably 1, nitrogen atom(s) at interruptable, optional position(s) in the hydrocarbon chain of said group or not interrupted, examples of which include those groups represented by formulae (11)

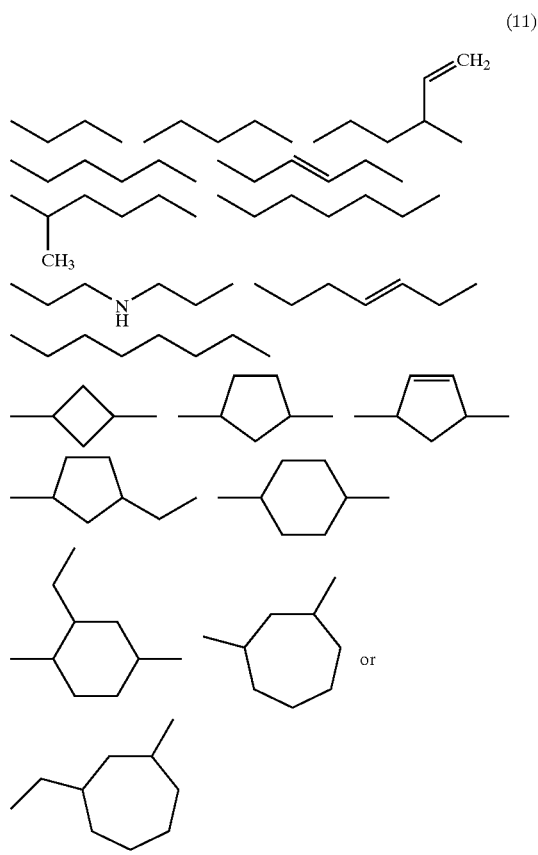

or those of the above formulae which however have 1, 2 or more, preferably 1, hydroxyl group(s) at optional, substitutable position(s) thereof.

"Cycloalkyl" means $C_3$–$C_7$ cycloalkyl groups, examples of which include cyclopropyl, cyclobutyl, cyclopentyl, cyclohexyl and cycloheptyl groups.

"$C_2$–$C_5$ alkylene which may be interrupted with oxygen" means $C_2$–$C_5$ alkylene groups which are interrupted with 1, 2 or more, preferably 1, oxygen atom(s) at interruptable, optional site(s) in said alkylene chain or not interrupted, examples of which include ethylene, trimethylene, tetramethylene, pentamethylene, 2-oxatetramethylene, 2-oxapentamethylene and 3-oxapentamethylene groups.

Examples of "$C_1$–$C_3$ alkylene" include methylene, ethylene and trimethylene groups.

Definition of each of $B^{11}$ and $B^{12}$ (or $B^{21}$ and $B^{22}$), "$C_1$–$C_6$ saturated or unsaturated aliphatic hydrocarbon which may be mutually crosslinked" means $C_1$–$C_6$ saturated or unsaturated aliphatic hydrocarbon groups which are not mutually crosslinked or have a mutual single bond or $C_1$–$C_4$ crosslinkage.

Examples of said $C_1$–$C_6$ saturated or unsaturated aliphatic hydrocarbon groups are divalent or trivalent groups formed of, e.g., methane, ethane, propane, propene, butane, 1-pentene, hexane or the like. More specifically, they form together with nitrogen atom adjacent to these groups, when they do not have crosslinkage, monocyclic groups comprising, e.g., aziridine ring, azetidine ring, pyrrolidine ring, piperidine ring, tetrahydropyridine ring or 2-vinylpiperidine ring; whereas, when they have crosslinkage, bicyclic groups comprising, e.g., 8-azabicyclo[3.2.1]octane ring, 3-azabicyclo[3.3.0]octane ring or 3-azabicyclo[3.3.1]nonane ring.

[Anion] is to make a pair with the ammonium ion on a compound of the present invention to electrically neutralize said compound and is not subject to any particular limitation so long as it is pharmaceutically acceptable. For example, anions formed from halogen, inorganic acid, organic sulfonic acid, carboxylic acid and the like, such as $F^-$, $Cl^-$, $Br^-$, $I^-$, $\frac{1}{2}SO_4^{2-}$, $HSO_4^-$, $\frac{1}{3}PO_4^{3-}$, $\frac{1}{2}HPO_4^{2-}$, $H_2PO_4^-$, $NO_3^-$, $CH_3OSO_3^-$, $CH_3SO_3^-$, $CH_3CH_2SO_3^-$,

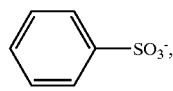

$HCOO^-$, $CH_3COO^-$,

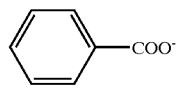

may be used.

Salts of the compounds represented by the general formula (I) means, for example, customary pharmaceutically acceptable salts of the compounds in which "A" in the formula stands for the groups expressed by formula ($b_0$). As such salts, for example, inorganic acid salts such as hydrochloride, sulfate, nitrate, phosphate and perchlorate; organic carboxylic acid salts such as benzoate, maleate, fumarate, succinate, tartarate, citrate and ascorbate; and organic sulfonic acid salts such as methanesulfonate, ethanesulfonate, isethionate, benzenesulfonate and p-toluenesulfonate may be named.

"Treating agent" means medicines which are applied to patients suffering from various diseases for therapeutic and/or prophylactic purposes.

"Inhalant" means those medicines per se well known in the medical field, which are in the form of being used by inhaling through the respiratory organ at the application time, such as aerosol, inhalant powder, inhalant liquid, and the like.

The compounds of the present invention in occasions have stereoisomers or tautomers such as optical isomers, diastereoisomers or geometrical isomers, depending on configuration of substituents. The invention includes all of such stereoisomers, tautomers and their mixtures within its scope.

With the view to disclose the compounds of the invention still more specifically, the symbols and signs are explained in further details hereunder, citing preferred specific examples.

A signifies the groups expressed by the formulae ($a_0$) or ($b_0$)

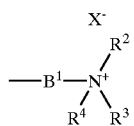

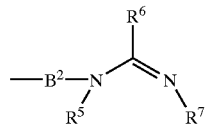

$B^1$ and $B^2$ signify, independently of each other, straight chain, branched chain and/or cyclic portion-containing $C_2$–$C_{10}$ saturated or unsaturated aliphatic hydrocarbon which may have hydroxyl group(s) and/or be interrupted with nitrogen atom(s).

As $B^1$, for example, those groups represented by formulae (12)

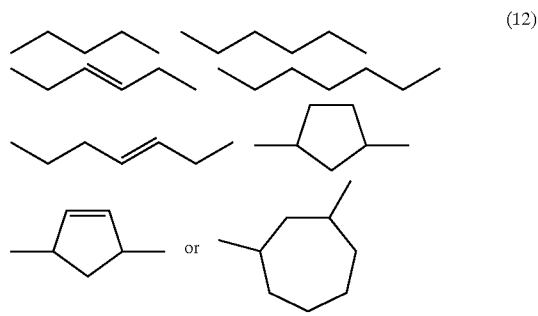

are convenient, in particular, those represented by formulae (13) are preferred.

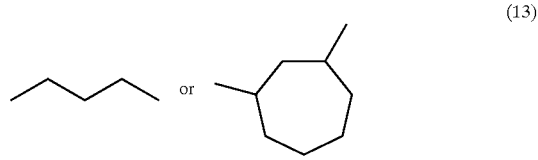

As $B^2$, for example, those groups represented by formulae (14)

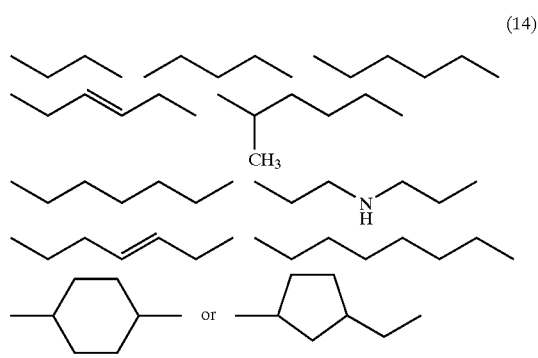

are convenient, in particular, that represented by a formula (15) is preferred.

In the formula ($a_0$), $R^2$, $R^3$ and $R^4$ signify, either independently of each other, a lower alkyl optionally having substituent(s) selected from a group consisting of phenyl and cycloalkyl, or $R^2$ and $R^3$ together signify a $C_2$–$C_5$ alkylene which may be interrupted with oxygen, or $R^4$ signifies a single bond or $C_1$–$C_3$ alkylene binding to a bindable optional site on $B^1$, and $X^-$ signifies an anion.

Said "lower alkyl optionally having substituent(s) selected from a group consisting of phenyl and cycloalkyl" defining $R^2$, $R^3$ and $R^4$ signify aforesaid unsubstituted lower alkyl or the lower alkyl having substituent(s) on substitutable, optional position(s), said 1, 2 or more, preferably 1, substituent(s) which are the same or different and selected from the group consisting of phenyl and cycloalkyl.

As cycloalkyl which can be present as the substituent, for example, cyclohexyl, cycloheptyl and the like are preferred.

Where $R^2$, $R^3$ or $R^4$ are "lower alkyl", for example, methyl, ethyl, propyl, isopropyl and the like are preferred.

Accordingly, where $R^2$, $R^3$ and $R^4$ represent, independently of each other, "lower alkyl optionally having substituent(s)", specific examples include methyl, ethyl, propyl, isopropyl, cyclohexylmethyl, cycloheptylmethyl, benzyl and the like, methyl being preferred.

As "$C_2$–$C_5$ alkylene which may be interrupted with oxygen" formed by $R^2$ and $R^3$ together, for example, tetramethylene, pentamethylene, 3-oxapentamethylene and the like are convenient. In particular, 3-oxapentamethylene group is preferred.

Where $R^4$ binds to a bindable optional site on $B^1$, single bond or methylene or ethylene are preferred as such $R^4$.

In preferred embodiments of $R^2$, $R^3$ and $R^4$, for example, $R^2$ and $R^3$ either stand for, independently of each other, lower alkyl optionally having substituent(s) selected from the group consisting of phenyl and cycloalkyl; or $R^2$ and $R^3$ together signify a $C_2$–$C_5$ alkylene which may be interrupted with oxygen and $R^4$ signifies a single bond or $C_1$–$C_3$ alkylene which binds to a bindable optional site on $B^1$.

As $X^-$, for example, anions formed from halogen atoms such as $Cl^-$, $Br^-$, and the like are preferred.

More specific, preferred embodiments of A in the general formula (I) in which A is a group represented by the formula ($a_0$) include, for example, a group expressed by a formula ($a_1$)

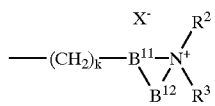

(a₁)

[in which $B^{11}$ and $B^{12}$ are, independently of each other, $C_1$–$C_6$ saturated or unsaturated aliphatic hydrocarbon groups, which may be mutually crosslinked; k is 0, 1 or 2; and $R^2$, $R^3$ and $X^-$ have the earlier given significations (provided that the sum of carbon atoms of $B^{11}$ and $B^{12}$, carbon atoms forming the crosslinkage and k does not exceed 13)]. In particular, as A, a group expressed by any one of formulae ($a_2$):

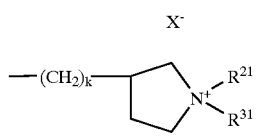

(a₂)

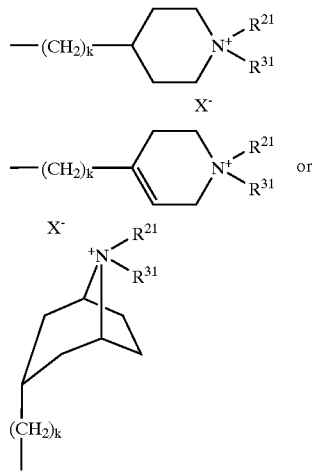

[in which $R^{21}$ and $R^{31}$ signify lower alkyl independently of each other; and k and $X^-$ have the earlier given significations] is preferred. In the most favorable embodiments, A is a group expressed by a formula ($a_3$)

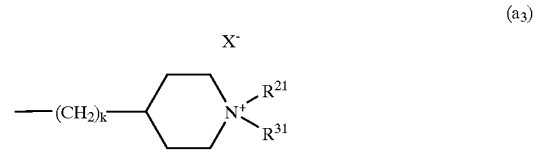

(a₃)

[in which k, $R^{21}$, $R^{31}$ and $X^-$ have the earlier given significations] or a formula ($a_4$)

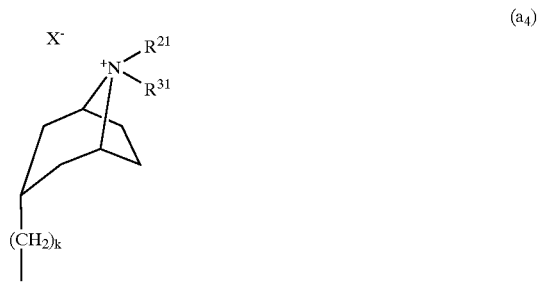

(a₄)

[in which k, $R^{21}$, $R^{31}$ and $X^-$ have the earlier given significations].

The embodiments in which k in the formulae ($a_1$), ($a_2$), ($a_3$) or ($a_4$) is zero (0) are preferred.

Furthermore, the embodiments in which both $R^{21}$ and $R^{31}$ in the formulae ($a_2$), ($a_3$) or ($a_4$) are methyl groups are preferred.

As $X^-$ in the formulae ($a_1$), ($a_2$), ($a_3$) or ($a_4$), for example, anions formed from halogen atoms such as $Cl^-$, $Br^-$, and the like are preferred.

In the formula ($b_0$), $R^5$ signifies hydrogen or a lower alkyl optionally having substituent(s) selected from the group consisting of phenyl and cycloalkyl, and $R^7$ signifies hydrogen or a lower alkyl; or either one of $R^5$ and $R^7$ signifies a single bond or $C_1$–$C_3$ alkylene binding to a bindable optional site on $B^2$.

Said definition of $R^5$, "lower alkyl optionally having substituent(s) selected from the group consisting of phenyl and cycloalkyl", signifies the same to the earlier given definition of $R^2$, $R^3$ or $R^4$, "lower alkyl optionally having substituent(s) selected from the group consisting of phenyl and cycloalkyl", specific examples of which also being the same. Of those named examples, methyl and ethyl are preferred.

As lower alkyl represented by $R^7$, methyl and ethyl are preferred.

Where either one of $R^5$ and $R^7$ binds to a bindable optional site on $B^2$, preferred $R^5$ or $R^7$ is single bond, methylene or ethylene.

$R^6$ signifies hydrogen, lower alkyl or a group represented by $-N(R^8)R^9$.

As lower alkyl represented by $R^6$, methyl, ethyl, propyl and butyl are preferred.

$R^8$ and $R^9$ signify, independently of each other, hydrogen or lower alkyl.

As lower alkyl represented by $R^8$ or $R^9$, methyl, ethyl, and propyl are preferred.

It is preferable that both $R^8$ and $R^9$ are hydrogen atoms.

Therefore, as the groups expressed as $-N(R^8)R^9$, for example, amino, methylamino, dimethylamino, ethylmethylamino and diethylamino, in particular, amino, are preferred.

As $R^6$, hydrogen and those groups expressed as $-N(R^8)R^9$ are preferred, hydrogen being the most preferred.

In preferred embodiments of $R^5$, $R^6$ and $R^7$, $R^5$ signifies a single bond or a $C_1$–$C_3$ alkylene binding to a bindable optional site on $B^2$; $R^6$ signifies hydrogen, lower alkyl or a group expressed as $-N(R^8)R^9$, preferably hydrogen; and $R^7$ signifies hydrogen.

In more specific, preferred embodiments where A in the general formula (I) is a group expressed by the formula $(b_0)$, A is a group represented by a formula $(b_1)$

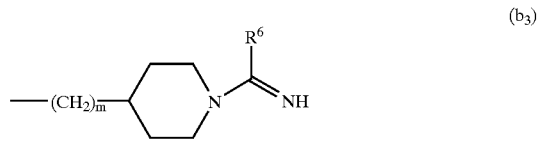

(b_1)

[in which $B^{21}$ and $B^{22}$ signify, independently of each other, a $C_1$–$C_6$ saturated or unsaturated aliphatic hydrocarbon group, which may be mutually crosslinked; m signifies 0, 1 or 2; $R^{71}$ signifies hydrogen or lower alkyl; and $R^6$ has the earlier given signification (provided that the sum of carbon atoms of $B^{21}$ and $B^{22}$, carbon atoms forming the crosslinkage and m does not exceed 13)], in particular, $R^{71}$ in that group is hydrogen. In still more favorable embodiments, A is a group represented by any one of the formulae $(b_2)$

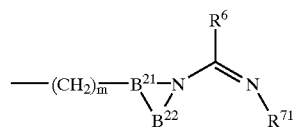

(b_2)

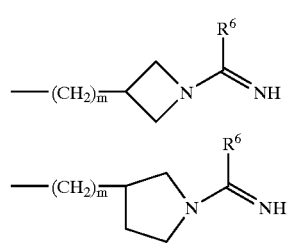

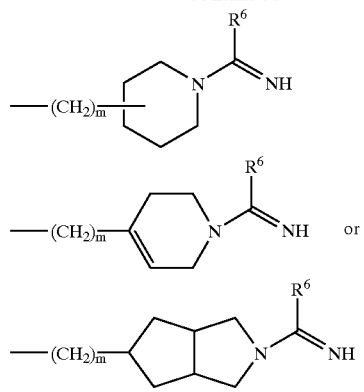

[in which m and $R^6$ have the earlier given significations]. It is of particular advantage that A is a group represented by a formula $(b_3)$ (b_3)

[in which m and $R^6$ have the earlier given significations].

In the formulae $(b_1)$, $(b_2)$ or $(b_3)$, m is preferably 1 or 2.

Furthermore, in the formulae $(b_1)$, $(b_2)$ or $(b_3)$, $R^6$ is preferably hydrogen.

Ar signifies aryl or heteroaryl optionally having substituent(s) selected from a group consisting of halogen, lower alkyl, lower alkenyl and lower alkoxy.

"Aryl or heteroaryl optionally having substituent(s) selected from a group consisting of halogen, lower alkyl, lower alkenyl and lower alkoxy" signify unsubstituted aryl or heteroaryl, or the aryl or heteroaryl having substituent(s) at substitutable optional position(s) thereon, said 1, 2 or more, preferably 1 or 2, substituent(s) which are the same or different and selected from the group consisting of halogen, lower alkyl, lower alkenyl and lower alkoxy.

As the substituent halogen, for example, fluorine, chlorine and bromine are preferred.

As the substituent lower alkyl, for example, methyl, ethyl, propyl and isopropyl are preferred.

As the substituent lower alkenyl, for example, vinyl is preferred.

As the substituent lower alkoxy, for example, methoxy, ethoxy and methylenedioxy are preferred.

As the substituent(s), halogen is preferred.

Where Ar is "aryl", for example, phenyl is preferred.

Where Ar is "heteroaryl", for example, 2-pyridyl, 2-thiazolyl, 2-thienyl and 3-thienyl are preferred.

Accordingly, as examples of Ar, phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2, 4-difluorophenyl, 3,4-difluorophenyl, 2-chloro-4-fluorophenyl, 2-methylphenyl, 3-methylphenyl, 4-methylphenyl, 2-ethylphenyl, 3-ethylphenyl, 4-ethylphenyl, 2-vinylphenyl, 3-vinylphenyl, 4-vinylphenyl, 4-methoxyphenyl, 4-ethoxyphenyl and 3,4-methylenedioxyphenyl can be named. Of those, phenyl, 4-fluorophenyl, 2-chlorophenyl, 4-chlorophenyl, 4-bromophenyl, 3,4-difluorophenyl, 4-methylphenyl, 4-ethylphenyl, 4-vinylphenyl and 3,4-methylenedioxyphenyl are preferred. In particular, where A in the general formula (I) is a group represented by the formula ($a_0$), 4-chlorophenyl is preferred, and where A is a group represented by the formula ($b_0$), unsubstituted phenyl is preferred.

$R^1$ signifies a fluorine-substituted $C_4$–$C_6$ cycloalkyl optionally having hydroxyl group(s). "Fluorine-substituted $C_4$–$C_6$ cycloalkyl optionally having hydroxyl group(s)" include $C_4$–$C_6$ cycloalkyl substituted with 1, 2 or more, preferably 1 or 2, inter alia, 2 fluorine atoms at substitutable, optional position(s), said cycloalkyl groups further having 1, 2 or more, preferably 1, hydroxyl group(s) at substitutable optional position(s) thereon or not having them.

As "cycloalkyl" of $R^1$, for example, cyclopentyl is preferred.

Accordingly, examples of $R^1$ include 1-fluorocyclobutyl, 1-fluorocyclopentyl, 2-fluorocyclobutyl, 2-fluorocyclopentyl, 3-fluorocyclobutyl, 3-fluorocyclopentyl, 2,2-difluorocyclobutyl, 2,2-difluorocyclopentyl, 3,3-difluorocyclobutyl, 3,3-difluorocyclopentyl, 3,3-difluoro-4-hydroxycyclopentyl, 3,3,4,4-tetrafluorocyclopentyl, 2,3-difluorocyclobutyl, 2,3-difluorocyclopentyl, 3,4-difluorocyclopentyl, 2,2,3,3-tetrafluorocyclobutyl and 2,2,3,3-tetrafluorocyclopentyl. Of those, 2-fluorocyclobutyl, 2-fluorocyclopentyl, 3-fluorocyclobutyl, 3-fluorocyclopentyl, 2,2-difluorocyclobutyl, 2,2-difluorocyclopentyl, 3,3-difluorocyclobutyl, 3,3-difluorocyclopentyl, 3,3-difluoro-4-hydroxycyclopentyl, 3,3,4,4-tetrafluorocyclopentyl and 2,2,3,3-tetrafluorocyclopentyl are convenient. In particular, 3,3-difluorocyclopentyl is preferred.

In the general formula (II), $A^P$ signifies a group represented by the formulae ($a_{p0}$) or ($b_{p0}$)

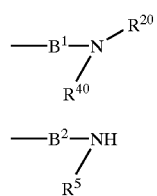

(a_{p0})

(b_{p0})

[in which $B^1$, $B^2$, $R^5$, $R^{20}$ and $R^{40}$ have the earlier given significations].

Needless to say, preferred embodiments of the compounds represented by the general formula (II) correspond to the preferred embodiments of the compounds represented by the general formula (I).

As examples of "optionally substituted lower alkyl" of $R^{20}$ or $R^{40}$, independently of each other, methyl, ethyl, propyl, isopropyl, cyclohexylmethyl, cycloheptylmethyl and benzyl can be named, in particular, methyl being preferred.

As $R^{40}$, a single bond or $C_1$–$C_3$ alkylene which bind to a bindable optional site on $B^1$, in particular, a single bond, methylene or ethylene are preferred.

In more specific, preferred embodiments wherein $A^P$ is a group represented by the formula ($a_{p0}$), for example, $A^P$ is a group represented by a formula ($a_{p1}$)

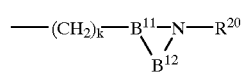

(a_{p1})

[in which $B^{11}$, $B^{12}$, k and $R^{20}$ have the earlier given significations], in particular, a group represented by any one of formulae ($a_{p2}$)

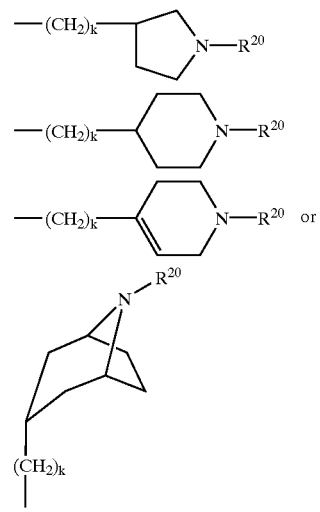

(a_{p2})

[in which k and $R^{20}$ have the earlier given significations]. In most favorable embodiments, for example, $A^P$ is a group represented by a formula ($a_{p3}$)

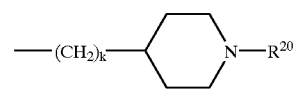

(a_{p3})

[in which k and $R^{20}$ have the earlier given significations] or a formula ($a_{p4}$)

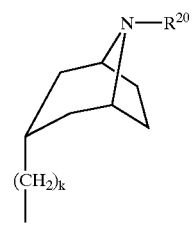

(a_{p4})

[in which k and $R^{20}$ have the earlier given significations].

In more specific, preferred embodiments wherein $A^P$ is a group represented by the formula ($b_{p0}$), for example, $A^P$ is a group represented by a formula ($b_{p1}$)

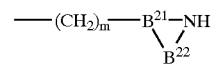

(b_{p1})

[in which $B^{21}$, $B^{22}$ and m have the earlier given significations], in particular, is a group represented by any one of formulae ($b_{p2}$)

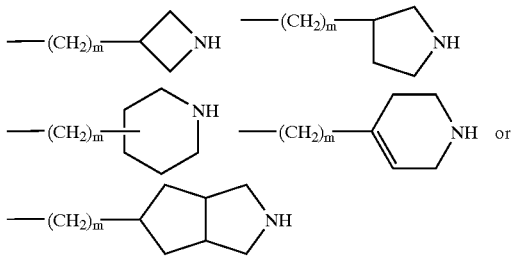

[in which m has the earlier given signification]. In most favorable embodiments, $A^p$ is a group represented by a formula ($b_{p3}$)

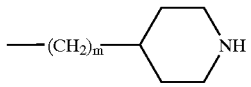

[in which m has the earlier given signification].

As Ar or $R^1$ in the general formula (II), examples similar to those named for Ar or $R^1$ of the general formula (I) can be named, preferred examples again being the same. Specific examples of $B^{11}$, $B^{12}$, $B^{21}$, $B^{22}$, k, m or $R^5$ in the formulae ($a_{p1}$), ($a_{p2}$), ($a_{p3}$), ($a_{p4}$), ($b_{p0}$), ($b_{p1}$), ($b_{p2}$) or ($b_{p3}$) are same to those for $B^{11}$, $B^{12}$, $B^{21}$, $B^{22}$, k, m or $R^5$ in the formulae ($a_1$), ($a_2$), ($a_3$), ($a_4$), ($b_0$), ($b_1$), ($b_2$) or ($b_3$), preferred examples again being the same.

As "salts" of the compounds represented by the general formula (II), for example, those acid addition salts via basic nitrogen atoms can be named.

As said acid addition salts, for example, inorganic acid salts such as hydrochloride, sulfate, nitrate, phosphate and perchlorate; organic acid salts such as maleate, fumarate, tartarate, citrate, asocorbate and trifluoroacetate; and sulfonic acid salts such as methanesulfonate, isethionate, benzenesulfonate and p-toluene-sulfonate can be named.

Now production processes of the compounds to which the present invention relates shall be explained.

Compounds (I) of the present invention can be produced, for example, by the following processes or those described in working examples, it being understood that production processes of the compounds (I) of the present invention are not limited by these reaction examples.

Production Process 1

Through reaction of a compound represented by a general formula (II-1)

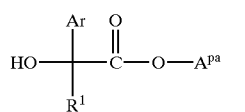

(II-1)

[in which $A^{pa}$ signifies a group represented by the formula ($a_{p0}$)

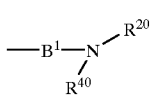

($a_{p0}$)

and Ar, $B^1$, $R^1$, $R^{20}$ and $R^{40}$ have the earlier given significations] or a salt thereof, with a compound represented by a general formula (III)

[in which L signifies a leaving group, and $R^{30}$ signifies a lower alkyl optionally having substituent(s) selected from a group consisting of phenyl and cycloalkyl], a compound represented by a general formula (I-1)

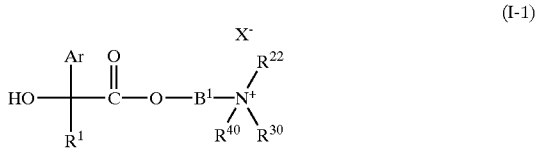

(I-1)

[in which $R^{22}$ signifies a lower alkyl optionally having substituent(s) selected from the group consisting of phenyl and cycloalkyl; and Ar, $B^1$, $R^1$, $R^{30}$, $R^{40}$ and $X^-$ have the earlier given significations] can be prepared.

"Salts" of the compounds represented by the general formula (II-1) signify acid addition salts via amino or imino, examples of which include inorganic acid salts such as hydrochloride, sulfate, nitrate, phosphate and perchlorate; organic acid salts such as maleate, fumarate, tartarate, citrate, ascorbate and trifluoroacetate; and sulfonic acid salts such as methanesulfonate, isethionate, benzenesulfonate and p-toluenesulfonate.

As the "leaving group" expressed as L, for example, halogen atoms such as chlorine, bromine and iodine; alkylsulfonyloxy group such as methylsulfonyloxy: and arylsulfonyloxy group such as p-toluenesulfonyloxy may be named.

The reaction of a compound represented by the general formula (II-1) or a salt thereof with a compound represented by the general formula (III) is normally conducted in an inert solvent having no adverse influence on the reaction.

As such inert solvent, for example, ethers such as diethyl ether, tetrahydrofuran and dioxane; aromatic hydrocarbons such as benzene, toluene, chlorobenzene and xylene; halogenated solvents such as chloroform and dichloromethane; aprotic polar solvents such as acetone and acetonitrile; or mixed solvents of the foregoing can be used.

The compound of the general formula (III) is normally used at the ratios of 1 mol-molar excess, in particular, 1–10 mols, per mol of the (II-1) compound. Especially when $R^{20}$ in the (II-1) compound is hydrogen, at least 2 mols of (III) compound is used.

The reaction temperature is normally in a range from about 0° C. to boiling point of the solvent, and the reaction time, from 10 minutes to 48 hours, while those conditions deviating from above ranges can be used where necessary.

The above reaction may be conducted in the presence of a base, for smooth progress of the reaction.

As suitable base, for example, alkali metal bicarbonates such as sodium hydrogencarbonate and potassium hydrogencarbonate; alkali metal carbonates such as sodium carbonate and potassium carbonate; tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-diazabicyclo[4.3.0]non-5-ene (DBN); and aromatic amines such as pyridine, 4-dimethylaminopyridine, picoline, lutidine, quinoline and isoquinoline may be named.

The use rate of said base is normally in a range of 1 mol-molar excess, preferably 1–10 mols, per mol of the (II-1) compound.

After termination of the reaction, conventional treatments are conducted to provide a compound of the general formula (I-1).

Production Process 2

Through reaction of a compound of a general formula (II-2)

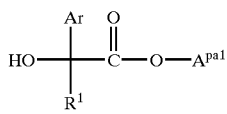
(II-2)

[in which $A^{pa1}$ signifies a group expressed by the formula $(a_{p01})$]

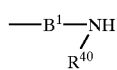
$(a_{p01})$ and Ar, $B^1$, $R^1$ and $R^{40}$ have the earlier given significations] or a salt thereof with a compound of a general formula (IV)

$$L^1—R^{31}—L^2 \quad (IV)$$

[in which $L^1$ and $L^2$ respectively signifies a leaving group independently of each other; and $R^{31}$ signifies a $C_2$–$C_5$ alkylene which may be interrupted with oxygen], a compound represented by a general formula (I-2)

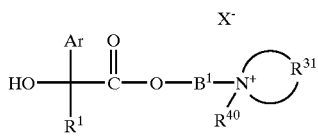
(I-2)

[in which Ar, $B^1$, $R^1$, $R^{31}$, $R^{40}$ or $X^-$ have the earlier given significations] can be prepared.

As examples of the "salts" of the compounds represented by the general formula (II-2), those similar to the salts of the compounds (II-1) in the above production process 1 can be named.

As $L^1$ or $L^2$ "leaving group", same leaving groups as those expressed as L in the above production process 1 can be named.

The reaction of a compound of the general formula (II-2) or a salt thereof with a compound of the general formyla (IV) can be conducted in the manner similar to the reaction of a compound of the general formula (II-1) or a salt thereof with a compound of the general formula (III) in the production process 1.

After termination of the reaction, conventional treatments are conducted to provide a compound of the general formula (I-2).

Production Process 3

Through reaction of a compound of a general formula (II-3)

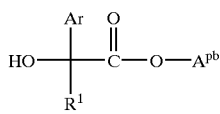
(II-3)

[in which $A^{pb}$ signifies a group represented by the formula $(b_{p0})$]

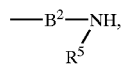
$(b_{p0})$ and Ar, $B^2$, $R^1$ and $R^5$ have the earlier given significations] or a salt thereof with a compound of a general formula (V)

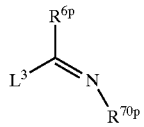
(V)

[in which $L^3$ signifies a leaving group; $R^{6p}$ signifies hydrogen, a lower alkyl or a group expressed as —N($R^{8p}$)$R^{9p}$; $R^{70p}$ signifies a protective group of imino, hydrogen or a lower alkyl; $R^{8p}$ and $R^{9p}$ signify, independently of each other, a protective group of amino or imino, hydrogen or lower alkyl] or a salt thereof, a compound of a general formula (VI)

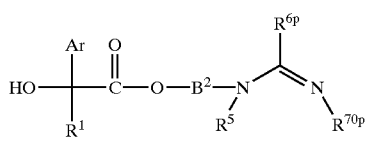
(VI)

[in which Ar, $B^2$, $R^1$, $R^5$, $R^{6p}$ and $R^{70p}$ have the earlier given significations] or its salt is obtained. Upon optionally removing the protective groups, a compound of a general formula (I-3)

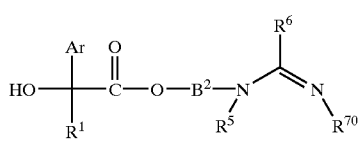
(I-3)

[in which $R^{70}$ signifies hydrogen or a lower alkyl, and Ar, $B^2$, $R^1$, $R^5$ and $R^6$ have the earlier given significations] or a salt thereof can be produced.

As the "salts" of the compounds represented by the general formula (II-3), (V) or (VI), those similar to the named salts of compounds (II-1) in the production process 1 can be used.

As the "leaving group" expressed as $L^3$, for example, halogen such as chlorine, bromine and iodine; lower alkoxy such as methoxy, ethoxy, butoxy, propoxy and isopropoxy; lower alkylthio such as methylthio and ethylthio; 1-imidazolyl, 1-pyrazolyl, 1-benzotriazolyl and the like may be named.

In the above reaction, when the reactant(s) contain amino or imino group(s) not participating in the reaction, said amino or imino group(s) are adequately protected with protective group(s), preceding the reaction, The protective groups can be removed after the reaction.

As such "protective groups of amino or imino group(s)", for example, aralkyl such as benzyl, p-methoxybenzyl, 3,4-dimethoxybenzyl, o-nitrobenzyl, p-nitrobenzyl, benzhydryl and trityl; lower alkanoyl such as formyl, acetyl, propionyl, butyryl and pivaloyl; benzoyl; arylalkanoyl such as phenylacetyl and phenoxyacetyl; lower alkoxycarbonyl such as methoxycarbonyl, ethoxycarbonyl, propyloxycarbonyl and tert-butoxycarbonyl; aralkyloxycarbonyl such as benzyloxycarbonyl, p-nitrobenzyloxycarbonyl and phenethyloxycarbonyl; lower alkylsilyl such as trimethylsilyl and tert-butyldimethylsilyl; phthaloyl; aralkylidene such as benzylidene, p-chlorobenzylidene and o-nitrobenzylidene may be named. Also as a protective group of imino on, for example, an amidino group, nitro can be named. Of those protective groups, in particular, acetyl, pivaloyl, benzoyl, ethoxycarbonyl, tert-butoxycarbonyl and benzyloxycarbonyl groups are preferred.

The reaction of a compound of the general formula (II-3) or a salt thereof with a compound of the general formula (V) or a salt thereof is normally conducted in an inert solvent having no adverse effect on the reaction, using 1 mol-molar excess, preferably 1–2 mols, of the compound (V) or a salt thereof, per mol of the compound (II-3) or a salt thereof.

As the inert solvent, for example, alcohols such as methanol and ethanol; ethers such as diethyl ether, tetrahydrofuran and dioxane; aromatic hydrocarbons such as benzene, toluene, chlorobenzene and xylene; aprotic polar solvents such as dimethylsulfoxide, N,N-dimethylformamide, acetonitrile and hexamethylphosphoric triamide or their mixtures can be used.

The reaction temperature is normally in a range from $-70°$ C. to boiling point of the solvent used in the reaction, preferably from $-20°$ C. to $100°$ C.

The reaction time normally ranges from 5 minutes to 7 days, preferably from 10 minutes to 24 hours.

The reaction may be conducted in the presence of a base, for smooth progress of the reaction.

As the base, those similar to the useful bases in the reaction of a compound (II-1) or a salt thereof with a compound (III) in the production process 1 may be named as examples.

The use rate of said base is normally in a range of 1 mol-molar excess, preferably 1–10 mols, per mol of the compound (V) where said compound contains a protective group.

On the other hand, where an unprotected compound is used as the compound (V), preferably a salt of the same compound is used. In such a case, furthermore, it is preferred that an equivalent amount to the product of an acid be present in the reaction system and as the acid, one derived from the salt of the compound (V) can be utilized. Accordingly, when a compound (II-3) is used in free form as a starting material, the best result can be obtained when the free compound (II-3) and a salt of a compound (V) are reacted at a ratio of substantially 1:1. Where a salt of a compound (II-3) is used, the reaction is preferably conducted in the presence of a base of an amount suitable for neutralizing the excessive acid in the present reaction system.

After termination of the reaction, ordinary post-treatments are conducted to provide a crude product of a compound of the general formula (VI) or a salt thereof. Thus obtained compound (VI) or a salt thereof is optionally purified by a means known per se, and optionally subjected to a deprotection reaction of the amino or imino group, to provide a compound of the formula (I-3) or a salt thereof.

Method for removing protective groups differs depending on such factors as the kind of the protective groups and stability of the object compound (I-3). The deprotection can be carried out using the methods known per se, for example, those described in *Protective Groups in Organic Synthesis*, T. W. Greene, John Wiley & Sons Co., Ltd. (1981) or methods analogous thereto, e.g., solvolysis using an acid or a base, that is, a method in which 0.01 mole to over excess of an acid, preferably trifluoroacetic acid, formic acid, hydrochloric acid and the like, or equimole to over excess of a base, preferably potassium hydroxide, calcium hydroxide and the like are acted; chemical reduction using a metal hydride complex; or catalytic reduction using a palladium-carbon catalyst, a Raney nickel catalyst or the like.

Production Process 4

Through reduction of a compound represented by a general formula (VII)

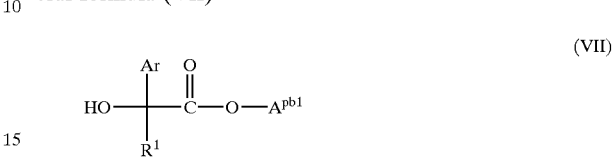

[in which $A^{pb1}$ signifies a group represented by a formula $(b_{p01})$]

$B^{23}$ signifies a straight chain, branched chain and/or cyclic portion-containing $C_2$–$C_{10}$ saturated or unsaturated aliphatic hydrocarbon which may have hydroxyl group(s) and/or be interrupted with nitrogen atom(s); $R^{71}$ signifies a single bond or a $C_1$–$C_3$ alkylene; Z signifies sulfur or a group expressed as =N—NO$_2$; and Ar and $R^1$ have the earlier given significations] or a salt thereof, and subsequent optional introduction into the same compound a lower alkyl, a compound represented by a general formula (I-4)

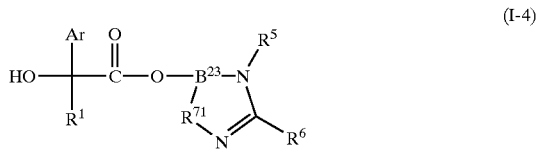

[in which Ar, $B^{23}$, $R^1$, $R^5$, $R^6$ and $R^{71}$ have the earlier given significations] or a salt thereof can be prepared.

As the "salts" of the compounds of the general formula (VII), those similar to the salts of the compounds (II-1) used in the production process 1 can be named as examples.

The reducing reaction of a compound of the general formula (VII) can be conducted, for example, by the method described in JP-Hei 1 (1989)-128970A or methods analogous thereto. That is, where Z stands for sulfur, the reduction can be conducted in an inert solvent, e.g., methylene chloride, by treating the compound (VII) with Raney nickel at temperatures ranging $0°$ C.–$40°$ C. Where Z is a group expressed as =N—NO$_2$, the reduction can be conducted by transfer hydrogenation using, for example, formic acid, hydrazine or cyclohexene as the hydrogen donor, and palladium, as the catalyst.

The lower alkyl-introducing reaction can be optionally conducted, by methods known per se or those analogous thereto, by using, for example, alkyl iodide, dialkyl sulfate, and the like.

After termination of the reaction, conventional treatments are conducted to provide a compound represented by the general formula (I-4) or a salt thereof.

Isolation and purification of those compounds represented by the general formulae (I-1), (I-2), (I-3) or (I-4) or their salts can be conducted by applying customary separation means such as column chromatography using silica gel, adsorbent resin or the like; liquid chromatography; solvent extraction, or recrystallization, reprecipitation and the like, either singly or in suitable combination.

Those anions which are expressed as $X^-$ in the compounds represented by the general formula (I-1) or (I-2) are convertible to different kind of anions by methods known per se.

As such anion-converting methods, for example, a method comprising adsorbing a compound of the general formula (I-1) or (I-2), which has a certain kind of anion, onto a column filled with a suitable carrier, treating the same with a salt of an acid capable of providing an excess of a desired anion, and thereafter eluting the formed compound having the desired kind of anion can be used.

Compounds represented by the general formula (I-3) or (I-4) or their salts can be converted from free compounds to pharmaceutically acceptable salts by conventional methods. The salts can also be converted to free compounds.

Compounds represented by the general formula (I-3) or (I-4) are preferably isolated in the form of their salts, and therefore, after being isolated as a certain kind of salt, can be converted into a different, desired kind of salt.

As such salt-converting methods, for example, a method comprising adsorbing a salt of a compound of the general formula (I-3) or (I-4) onto a column filled with a suitable carrier, treating the same with an excess of a salt of a desired acid and thereafter eluting the formed, desired salt of the same compound can be used.

Compounds represented by the general formulae (II-1), (III), (II-2), (IV), (II-3), (V) or (VII) are commercially available, or they can be prepared by known methods or methods taught in literature [cf. International Publications WO 98/05641, WO 99/40070 and WO 00/31078; *Angew. Chem. Int. Edit.*, Vol.6, p.566 (1967); *Synth. Commun.*, Vol.25, No.8, p.1173 (1995) and Vol.27, No. 14, p.2393 (1997); *J. Org. Chem.*, Vol.52, p.1700 (1987) and Vol.57, p.2497 (1992)], methods analogous thereto or those described in the following Examples and Referential Examples.

Production Method A

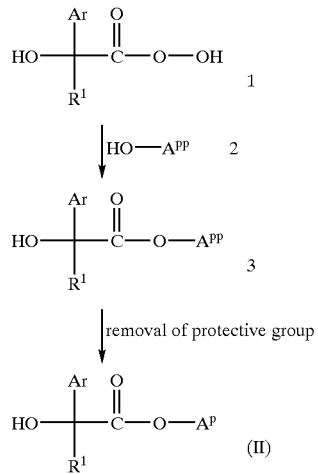

[in which $A^{pp}$ signifies a group represented by the formula $(a_{p0})$ or $(b_{p0p})$

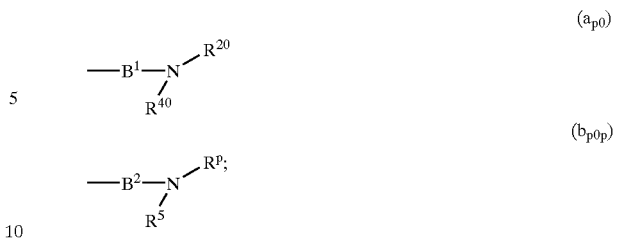

$R^p$ signifies a protective group of amino or imino, or hydrogen, or a lower alkyl optionally having substituent(s) selected from the group consisting of phenyl and cycloalkyl; and $A^p$, Ar, $B^1$, $B^2$, $R^1$, $R^5$, $R^{20}$ and $R^{40}$ have the earlier given significations].

This production method is for making compounds of the general formula (II). According to this method, a compound of the general formula (II) can be prepared by causing a compound of the general formula 2 to act on a carboxylic acid of the general formula 1 or a reactive derivative thereof to form a compound of the general formula 3, and optionally removing the protective group in said compound 3.

Those compounds represented by the general formulae (II-1), (II-2) or (II-3) are covered by the scope of the general formula (II).

The reaction between carboxylic acid of the general formula 1 or a reactive derivative thereof with a compound of the general formula 2 is normally conducted using 1–5 moles, preferably 1–2 moles, of the compound 2 per mole of the compound 1 or a reactive derivative thereof.

As "reactive derivatives" of the carboxylic acid represented by the general formula 1, for example, mixed acid anhydrides, active esters and active amides can be named, which can be obtained, for example, by those methods described in Internationl Publication WO 98/05641.

Where a carboxylic acid of formula 1 is used in the above reaction, the reaction is preferably carried out in the presence of a condensing agent such as carbonyldiimidazole, N,N'-dicyclohexylcarbodiimide, 1-ethyl-3-(3-dimethylaminopropyl)-carbodiimide, diphenylphosphorylazide, dipyridyldisulfide-triphenylphosphine and the like, in particular, carbonyldiimidazole.

The use rate of the condensing agent is not subject to strict limitation, while it is normally used in a range of 1–5 moles, preferably 1–2 moles, per mole of the carboxylic acid of the general formula 1.

The reaction is normally carried out in an inert solvent. As examples of the inert solvent, diethyl ether, tetrahydrofuran, N,N-dimethylformamide, dioxane, benzene, toluene, chlorobenzene, methylene chloride, chloroform, carbon tetrachloride, dichloroethane and trichloroethylene, or their mixtures can be named. Of these, diethyl ether, tetrahydrofuran, N,N-dimethylformamide and dioxane are preferred.

The reaction temperature normally ranges from −70° C. to boiling point of the used solvent, preferably from −20° C. to 100° C.

The reaction time normally ranges from 5 minutes to 7 days, preferably from 10 minutes to 24 hours.

The reaction can also be conducted in the presence of a base, for smooth progress of the reaction.

As the useful base, for example, sodium hydride; alkali metal bicarbonates such as sodium hydrogencarbonate and potassium hydrogencarbonate; alkali metal carbonates such as sodium carbonate and potassium carbonate; tertiary aliphatic amines such as trimethylamine, triethylamine, N,N- diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-diazabicyclo[4.3.0]non-5-ene (DBN); and aromatic amines such as pyridine, 4-dimethylaminopyridine, picoline, lutidine, quinoline and isoquinoline may be named. Of these, sodium hydride is preferred.

The use rate of the base can range from the catalytic amount to 5 moles, preferably the catalytic amount, per mole of the carboxylic acid of the general formula 1 or its reactive derivative.

In the above reaction, when the reactant(s) contain amino or imino group(s) not participating in the reaction, preferably said amino or imino group(s) are suitably protected with amino- or imino-protective groups before the reaction, and removed after the reaction.

As the amino- or imino-protective groups, those protective groups described in above production process 3 can be used.

After termination of the reaction, ordinary treatments are conducted to provide a crude product of a compound of the general formula 3. Thus obtained compound 3 is optionally purified by a means known per se and optionally subjected to a deprotection reaction of the amino or imino group(s), to provide a compound of the general formula (II).

As the method for removing the protective group(s), those described in the foregoing production process can be applied in the identical manner.

Compounds represented by the general formula (II) can also be prepared by the steps of producing, in the manner similar to the above production process, a compound of the general formula (II) in which $R^5$, $R^{20}$ or $R^{40}$ in the group $A^P$ is(are) hydrogen, and introducing into said compound a lower alkyl optionally having substituent(s) selected from the group consisting of phenyl and cycloalkyl.

The reaction for introducing said lower alkyl can be conducted by subjecting the compound of the general formula (II) in which $R^5$, $R^{20}$ or $R^{40}$ in the group $A^P$ is(are) hydrogen and (a) an aldehyde or ketone expressed as a general formula 5,

$$R^{44}=O \qquad 5$$

[in which $R^{44}$ signifies a lower alkylidene optionally having substituent(s) selected from the group consisting of phenyl and cycloalkyl] to reducing amination reaction, or (b) after removing the protective group(s) of said amino or imino group(s), reacting said compound with a compound expressed as a general formula 6,

$$R^{45}-L^4 \qquad 6$$

[in which $L^4$ signifies a leaving group, and $R^{45}$ signifies a lower alkyl optionally having substituent(s) selected from the group consisting of phenyl and cycloalkyl] in the presence of a base, to provide a compound within the scope of the general formula (II), in which $R^{20}$, $R^{40}$ or $R^5$ are, independently of each other, lower alkyl optionally having substituent(s) selected from the group consisting of phenyl and cycloalkyl.

$R^{44}$ which is "a lower alkylidene optionally having substituent(s) selected from the group consisting of phenyl and cycloalkyl" signifies the one which can be converted to the corresponding "lower alkyl optionally having substituent(s) selected from the group consisting of phenyl and cycloalkyl" after termination of the above reaction.

As the "leaving group" expressed as $L^4$, for example, halogen such as chlorine, bromine and iodine; alkylsulfonyloxy such as methylsulfonyloxy; and arysulfonyloxy such as p-toluenesulfonyloxy may be named.

The reducing amination reaction with the ketone or aldehyde in above step (a) is normally conducted in an inert solvent not detrimental to the reaction.

Examples of useful inert solvent include alcohols such as methanol and ethanol; ethers such as diethyl ether, tetrahydrofuran and dioxane; aromatic hydrocarbons such as benzene and toluene; and solvent mixtures thereof. In particular, methanol, ethanol, tetrahydrofuran and toluene are preferred.

The reaction temperature can normally be in the range of from about −30° C. to about 200° C., preferably from about 0° C. to about 100° C. Also the reaction time can normally be in the range of from 10 minutes to 7 days, preferably from 10 minutes to 24 hours.

Futhermore, the above reducing amination reaction can be conducted by using a reducing agent such as a metal hydride complex, e.g., sodium borohybride, sodium cyanoborohydride, lithium aluminum hydride, sodium triacetoxyborohydride or a mixture of sodium cyanoborohydride with zinc chloride; or by catalytic reduction using a palladium-on-carbon catalyst, a Raney nickel catalyst or the like.

Where a metal hydride complex is used as the reducing agent, the use rate of the reducing agent is normally in a range of 1 mole–molar excess, preferably 1–10 moles, per mole of the starting compound.

The reaction with a compound which is expressed as the general formula 6 in the step (b) is normally conducted in the presence of a base, in an inert solvent not detrimental to the reaction.

As suitable base, for example, alkali metal bicarbonates such as sodium hydrogencarbonate and potassium hydrogencarbonate; alkali metal carbonates such as sodium carbonate and potassium carbonate; tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-diazabicyclo[4.3.0]non-5-ene (DBN); and aromatic amines such as pyridine, 4-dimethylaminopyridine, picoline, lutidine, quinoline and isoquinoline may be named. In particular, N,N-diisopropylethylamine and potassium carbonate are preferred.

The use rate of the base can normally range 1 mole–molar excess, preferably 1–10 moles, per mole of the starting compound.

As examples of the inert solvent, ethers such as diethyl ether, tetrahydrofuran and dioxane; aromatic hydrocarbons such as benzene, toluene, chlorobenzene and xylene; aprotic polar solvents such as dimethylsulfoxide, N,N-dimethylformamide, acetonitrile and hexamethylphosphoric acid triamide; or their mixtures can be named.

The reaction temperature can normally range from about 0° C. to boiling point of the solvent used, and the reaction time can range from 10 minutes to 48 hours. Where necessary, however, more or less of these ranges can be used.

Introduction or removal of protective groups of amino or imino groups can be effected by methods known per se, for example, by those methods described in the literature identified in above production processes or methods analogous thereto.

Production process B

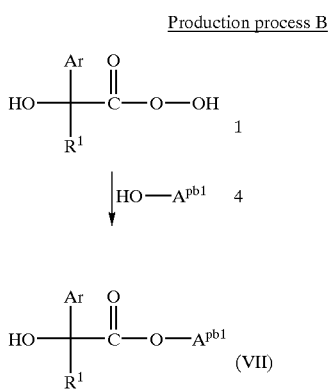

[in which $A^{pb1}$, Ar and $R^1$ have the earlier given significations].

This production process is that for producing the compounds represented by the general formula (VII). According to this production process, a compound represented by the general formula (VII) can be prepared by having a compound represented by the general formula 4 act on a carboxylic acid represented by the general formula 1 or a reactive derivative thereof.

The reaction between a carboxylic acid of general formula 1 or a reactive derivative thereof with a compound of the general formula 4 can be carried out in the manner similar to the reaction between a carboxylic acid of general formula 1 or a reactive derivative thereof with a compound of the general formula 2 in above production process A.

After termination of the reaction, conventional treatments are conducted to provide a compound represented by the general formula (VII).

As these compounds represented by the general formulae 1, 2, 4, 5 or 6, commercial products may be utilized, or they can be prepared by known methods, methods taught in literature [cf. International Publication Nos. WO 98/05641, WO 99/40070 and WO 00/31078, and JP Hei 1 (1989)-128970A], or methods analogous thereto, or those described in Examples and Referential Examples in this application, in suitable combination where necessary.

Utility of the compounds of the present invention is demonstrated by the following tests of their inhibition of binding to muscarinic receptors and of their antagonism to various muscarinic receptors.

Tests on Inhibition of Binding to Muscarinic Receptors

The following tests were performed according to an improvement of the method of Hargreaves, et al. (Br. J. Pharmacol. 107: 494–501, 1992). CHO cells expressing $m_2$ and $m_3$ muscarinic acetylcholine receptor (Receptor Biology, Inc.), 0.2 nM [$^3$H]-N-methylscopolamine (84 Ci/mmol, New England Nuclear Co.) and each of the compounds to be tested, were incubated in 0.5 ml of 50 mM tris-HCl-10 mM $MgCl_2$-1 mM EDTA solution (pH 7.4) at room temperature (about 20–25° C.) for 120 minutes, suction filtered over a glass filter (Packard, Unifilter Plate GF/C) and washed 4 times with 1 ml of ice-cold tris-HCl buffer. The filter was dried at 50° C. for an hour, then a scintillator (Packard, Microscinti 0) was added, and the radioactivity of [$^3$H]-N-methylscopolamine adsorbed onto the filter was counted with a microplate scintillation counter (Packard, TopCount). Receptor non-specific binding of [$^3$H]-N-methylscopolamine was determined by adding 1 μM N-methylscopolamine. The binding affinity of each compound of the present invention to muscarinic receptors is expressed as dissociation constant (Ki) calculated from the concentration of tested compound which achieves 50% inhibition ($IC_{50}$ value) of binding of labeled ligand, [$^3$H]-N-methylscopolamine, following the method of Cheng and Prusoff [Biochem Pharmacol., Vol. 22, pp. 3099–3108 (1973)]

TABLE 1

Inhibition Action on Binding to Muscarinic $m_2$ and $m_3$ Receptors

| | Ki(nM) | | |
|---|---|---|---|
| | $m_2$ | $m_3$ | $m_2/m_3$ |
| Compound of Example 6 | 29.1 | 0.425 | 68.5 |
| Compound of Example 54 | 4.76 | 0.079 | 60.2 |

As is clear from the results indicated in above Table 1, compounds of the present invention exhibited far higher binding-inhibitory activity to $m_3$ receptor, than that to $m_2$ receptor.

Test of Antagonism to Muscarinic Receptors (in vitro)

1) Test for Antagonism to $M_2$ Receptor in an Isolated Rat Right Atrium

These tests were performed according to a conventional method. A male SD strain rat (weighing 300–500 g) was killed by exsanguination, and the right atrium was isolated. This preparation was isometrically suspended in Magnus tube filled with 20 ml of Krebs Henseleit solution (gassed with 95% $O_2$–5% $CO_2$, 32° C.) with an initial tension of 0.5 g. The heart rate was recorded with a heart rate counter. After the preparation was equilibrated for 30 minutes, carbachol (1.7 nM–36 mM) was cumulatively administered in threefold increasing doses. Thus, a decrease in heart rate was measured to obtain a dose-response curve for the control experiment. After the preparation was washed with fresh solution to restore the heart rate, a test compound was administered thereto. Twenty minutes later, carbachol was cumulatively administered again. Responses to carbachol were expressed as percentages based on the heart rate before administration of carbachol as 100%. The antagonistic potency ($K_B$ value) of the test compound was determined from the degree of shift of the dose-response curve obtained by treatment with individual test compound of the present invention.

2) Tests for Antagonism to the Airway $M_3$ Receptor in an Isolated Rat Tranchea These tests were performed according to a conventional method. A male SD strain rat (weighing 300–500 g) was killed by exsanguination, and the trachea was isolated. Annular segments (2 mm wide) were cut out from the trachea and cut transversely at the anterior cartilage part to make open ring preparation. The preparation was suspended in a Magnus tube filled with 5 ml of Krebs-Henseleit solution (gassed with 95% $O_2$–5% $CO_2$, 32° C.) with an initial tension of 1.0 g and a resting tension of 0.6 g. The tension of the preparation was recorded isometrically. After being equilibrated for an hour, the preparation was made to contract twice by treatment with $10^{-4}$ M carbachol, and the second contraction induced by carbachol was used as the reference contraction. After the preparation was washed with fresh solution to be restored to the base line, a vehicle or one of the test compounds was administered to another preparation prepared from the same individual. Twenty minutes later, carbachol (1.7 nM–36 mM) was cumulatively administered in three-fold increasing doses to obtain a dose-response curve. The dose-response curve was plotted by expressing responses as percentages based on the reference contraction of the preparation as 100%. The antagonistic potency ($K_B$ value) of the test compound was determined from the degree of shift of the dose-response curve obtained by treatment with the test compound.

TABLE 2

Antagonism to Muscarinic Receptors (in vitro)

| | KB (nM) | | |
|---|---|---|---|
| | Right atrium $M_2$ | Trachea $M_3$ | $M_2/M_3$ |
| Compound of Example 6 | 9.6 | 0.044 | 218 |
| Compound of Example 54 | 10.6 | 0.21 | 50 |

As is clear from the results indicated in above Table 2, the compounds of the present invention exhibited far more powerful antagonism to the trachea $M_3$ receptor than to the right atrium $M_2$ receptor. Therefore, the compounds of the present invention are more selective for trachea $M_3$ receptor.

Test for Antagonism Against Muscarinic $M_3$ Receptor (in vivo)

1) Tests for Bronchodilation in Anesthetized Dogs (Inhalation Administration)

Bronchodilating action after administering each of the tested compound by inhalation was evaluated by measuring the inhibitory effect on airway resistance-increasing reaction in methacholine provocation test. In the experiments, 12–36 months old male beagle dogs (weighing 10–15 kg) were used, which were anesthetized with pentobarbital (30 mg/kg, i.v.) and intubated in their bronchus. After their respiration was stabilized, they were connected to Astograph (TCK-6100H, Chest Co.) and methacholine provocation test was conducted by 3 Hz oscillation method. Methacholine which is an inhalation-inducing agent was diluted with physiologic salt solution to ten concentration levels starting from 40,000 µg/ml, successively as 20,000, 10,000, 5,000, 2,500, 1,250, 625, 312.5, 156 and 78 µg/ml. Using the nebulizer in the Astograph, the test animals were made to inhale the methacholine solutions starting from that of the lowest concentration, each for one minute per solution, and changes in their respiration resistance was continuously recorded. The concentration level at which the respiration resistance reached twice the initial value was recorded as the methacholine reaction threshold value. Before evaluating the tested medicines, methacholine reaction threshold values[1]) of the dogs not treated with any of the tested medicines were measured at least twice at a week or longer interval(s) to select the dogs which showed reproducible reactions.

The inhaling administration of each of the tested medicines (1 mg/ml) was carried out for 10 minutes under anesthesis with pentobarbital (30 mg/kg, i.v.) using the nebulizer in the Astograph. In 5 minutes and 4 hours from the inhaling administration, methacholine provocation tests were conducted to measure the methacholine reaction threshold values[2]) after administration of the tested medicines. Same measurements after 24 hours were conducted after those conducted after the dogs recovered from the 4$^{th}$ hour measurements.

The bronchodilator activity of the test compound (shift value) was determined according to the following equation. The result was shown in Table 3.

$$\text{Shift value} = \frac{\text{methacholine reaction threshold values}^{2)} \text{ after tested medicine administration}}{\text{methacholine reaction threshold values}^{1)} \text{ without treatment with tested medicine}}$$

TABLE 3

Bronchodilation Action in Dogs

| | Shift Value | | |
|---|---|---|---|
| | 5 minutes after | 4 hours after | 24 hours after |
| Compound of Example 6 | >30 | >30 | 5.8 |
| Compound of Example 54 | >30 | >30 | 3.9 |

As is clear from the results shown in above Table 3, the compounds of the present invention exhibited powerful bronchodilation action.

As above, the compounds of formula [I] of the present invention exhibit potent and selective antagonism to muscarinic $M_3$ receptors and exhibit excellent pharmacological activity and long duration of action also when administered by inhalation. Hence, they can be administered to patients orally or parenterally, preferably by inhalation, as safe pharmaceutics exhibiting little side effects, in the treatment of, in particular, such respiratory diseases as chronic obstructive pulmonary diseases, chronic bronchitis, asthma, chronic airway obstruction, fibroid lung, pulmonary emphysema and rhinitis.

In clinically applying the compounds of the present invention for the treatment or prophylaxis of such diseases, they may be combined with pharmaceutically acceptable adjuvants in the usual manner to formulate pharmaceutical preparation forms suitable for administration. As the adjuvants, various additives conventionally used in the field of pharmaceutics can be used. For example, gelatin, lactose, sucrose, titanium oxide, starch, crystalline cellulose, hydroxypropylmethylcellulose, carboxymethylcellulose, corn starch, microcrystalline wax, white petrolatum, magnesium aluminate metasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light anhydrous silicic acid, talc, vegetable oil, benzyl alcohol, acacia, propylene glycol, polyalkylene glycol, cyclodextrin and hydroxypropylcyclodextrin can be named.

As the dosage forms of pharmaceutical compositions prepared by using these adjuvants, solid preparations such as tablets, capsules, granules, powders and suppositories; and liquid preparations such as syrups, elixirs and injections can be named. These preparations may be formulated according to conventional techniques in the field of pharmaceutics. Liquid preparations may be in a form which is dissolved or suspended in water or other suitable medium prior to use. In particular, injections may be in the form advancedly dissolved or suspended in physiological saline solution or a glucose solution, or in powder form for reconstitution by dissolution or suspension in physiological saline or a glucose solution prior to use. If desired, such injections may contain buffer agents and/or preservatives.

Also as preparations for non-oral administration such as inhalant, they may be formulated into aerosol, inhaling powder or inhaling liquid. The inhaling liquid can take a form to be used as dissolved or suspended in water or other suitable medium at the application time.

In these pharmaceutical preparations, a compound of the present invention may be present at a ratio of from 1.0 to 100% by weight, preferably 1.0 to 60% by weight, based on the total weight of the preparation. These pharmaceutical preparations may additionally contain other therapeutically effective compounds.

When the compounds of the present invention are used as medicines, their dosage level and dosage schedule may vary according to sex, age and body weight of individual patient, severity of symptoms, type and range of the desired therapeutic effect, and the like. Generally for oral administration, they can be administered in a daily dose of 0.1 to 100 mg/kg for an adult at one time or in several divided doses. For parenteral administration, they can be administered in a daily dose of 0.001 to 10 mg/kg for an adult, at one time or in several divided doses.

BEST MODE FOR CARRYING OUT THE INVENTION

Hereinafter the present invention is more specifically explained with reference to working examples, it being understood that the examples are in no way limitative of the scope of the invention.

EXAMPLE 1

4-(((2R)-2-((1R)-3,3-difluorocyclopentyl)-2-hydroxy-2-phenyl-ethanoyl)oxy)-1,1-dimethylpiperidinium bromide (Step 1)

Synthesis of 1-methylpiperidin-4-yl(2R)-2-((1R)-3,3-difluorocyclopentyl)-2-hydroxy-2-phenylethanoate To a solution of 17 mg of piperidin-4-yl(2R)-((1R)-3,3-difluorocyclopentyl)-2-hydroxy-2-phenylethanoate and 0.03 ml of formaldehyde (35% aqueous solution) in 1 ml of methanol, 0.3 ml of advancedly prepared 0.3 M methanol solution of sodium cyanoborohydride and zinc chloride (1:0.5) was added at room temperature, followed by 30 minutes' stirring at the same temperature. The reaction liquid was diluted with ethyl acetate, washed successively with a saturated sodium hydrogencarbonate solution and with saturated brine, and dried over anhydrous sodium sulfate. Distilling the solvent off under reduced pressure, 19 mg of the title compound was obtained.

(Step 2)

Synthesis of 4-(((2R)-2-((1R)-3,3-difluorocyclopentyl)-2-hydroxy-2-phenylethanolyl)oxy)-1,1-dimethylpiperidinium bromide To 18 mg of 1-methylpiperidin-4-yl(2R)-2-((1R)-3,3-difluorocyclopentyl)-2-hydroxy-2-phenylethanoate, 0.5 ml of 10% methyl bromide-acetonitrile solution was added at room temperature, followed by standing for 15 hours at the same temperature. The solvent was condensed under reduced pressure, the residue obtained was purified with reversed phase medium pressure liquid chromatography [ODS-AQ 120-S50 (YMC Co.)] (eluent: tetrahydrofuran/water=1/1) to provide 17 mg of the title compound as a colorless solid.

$^1$H-NMR (D$_2$O, δ PPM): 1.78–2.36 (10H, m), 2.72–2.86 (1H, m), 3.02 (3H, s), 3.04 (3H, s), 3.18–3.61 (4H, m), 5.04–5.17 (1H, m), 7.40–7.60 (3H, m), 7.60–7.72 (2H, m)

ESI-MS (m/e, as (C$_{20}$H$_{28}$F$_2$NO$_3$)$^+$): 368

EXAMPLE 2

4-(((2R)-2-((1R)-3,3-difluorocyclopentyl)-2-hydroxy-2-(4-methylphenyl)ethanoyl)oxy)-1,1-dimethylpiperidinium bromide The title compound was prepared by the treating procedures similar to the method of Example 1, using piperidin-4-yl(2R)-2-((1R)-3,3-difluorocyclopentyl)-2-hydroxy-2-(4-methylphenyl)ethanoate. The product was obtained as a colorless, oily substance.

$^1$H-NMR (CD$_3$OD, δ PPM): 1.68–2.25 (10H, m), 2.32 (3H, s), 3.12 (6H, s), 3.13–3.46 (5H, m), 4.97–5.08 (1H, m), 7.21 (2H, d, J=8.4 Hz), 7.49 (2H, d, J=8.4 Hz)

ESI-MS (m/e, as (C$_{21}$H$_{30}$F$_2$NO$_3$)$^+$): 382

EXAMPLE 3

4-(((2R)-2-((1R)-3,3-difluorocyclopentyl)-2-hydroxy-2-(4-vinylphenyl)ethanoyl)oxy)-1,1-dimethylpiperidinium bromide The title compound was prepared by the treating procedures similar to the method of Example 1, using piperidin-4-yl(2R)-2-((1R)-3,3-difluorocyclopentyl)-2-hydroxy-2-(4-vinylphenyl)ethanoate. The product was obtained as a colorless, oily substance.

$^1$H-NMR (CD$_3$OD, δ PPM): 1.67–2.33 (10H, m), 3.14 (6H, s), 3.16–3.46 (5H, m), 5.02–5.10 (1H, m), 5.25 (1H, dd, J=1.8 Hz, 11.7 Hz), 5.80 (1H, dd, J=1.8 Hz, 17.7 Hz), 6.73 (1H, dd, J=11.7 Hz, 17.7 Hz), 7.46 (2H, d, J=8.4 Hz), 7.60 (2H, d, J=8.4 Hz)

ESI-MS (m/e, as (C$_{22}$H$_{30}$F$_2$NO$_3$)$^+$): 380

EXAMPLE 4

4-(((2R)-2-((1R)-3,3-difluorocyclopentyl)-2-hydroxy-2-(4-ethylphenyl)ethanoyl)oxy)-1,1-dimethylpiperidinium bromide The title compound was prepared by the treating procedures similar to the method of Example 1, using piperidin-4-yl(2R)-2-((1R)-3,3-difluorocyclopentyl)-2-hydroxy-2-(4-ethylphenyl)ethanoate. The product was obtained as a colorless, oily substance.

$^1$H-NMR (CD$_3$OD, δ PPM): 1.22 (3H, t, J=7.7 Hz), 1.60–2.30 (10H, m), 2.64 (2H, q, J=7.7 Hz), 3.12 (6H, s), 3.09–3.43 (5H, m), 5.02–5.10 (1H, m), 7.24 (2H, d, J=8.5 Hz), 7.53 (2H, d, J=8.55 Hz).

ESI-MS (m/e, as (C$_{22}$H$_{32}$F$_2$NO$_3$)$^+$): 396

EXAMPLE 5

4-(((2R)-2-((1R)-3,3-difluorocyclopentyl)-2-hydroxy-2-(4-fluorophenyl)ethanoyl)oxy)-1,1-dimethylpiperidinium bromide The title compound was prepared by the treating procedures similar to the method of Example 1, using piperidin-4-yl(2R)-2-((1R)-3,3-difluorocyclopentyl)-2-hydroxy-2-(4-fluorophenyl)ethanoate. The product was obtained as a colorless solid.

$^1$H-NMR (CD$_3$OD, δ PPM): 0.80–2.35 (10H, m), 3.05–3.20 (1H, m), 3.30 (3H, s), 3.44–3.75 (2H, m), 3.62 (3H, s), 3.95–4.30 (2H, s), 5.15–5.25 (1H, m), 7.03 (2H, t, J=8.8 Hz), 7.68 (2H, dd, J=5.4, 8.8 Hz)

ESI-MS (m/e, as (C$_{20}$H$_{27}$F$_3$NO$_3$)$^+$): 386

EXAMPLE 6

4-(((2R)-2-((1R)-3,3-difluorocyclopentyl)-2-hydroxy-2-(4-chlorophenyl)ethanoyl)oxy)-11-dimethylpiperidinium bromide The title compound was prepared by the treating procedures similar to the method of Example 1, using piperidin-4-yl(2R)-2-((1R)-3,3-difluorocyclopentyl)-2-hydroxy-2-(4-chlorophenyl)ethanoate. The product was obtained as a colorless solid.

$^1$H-NMR (CD$_3$OD, δ PPM): 1.60–2.32 (10H, m), 3.15 (3H, s), 3.18 (3H, s), 3.20–3.50 (5H, m), 5.03–5.12 (1H, m), 7.39 (2H, d, J=8.4 Hz), 7.63 (2H, d, J=8.4 Hz).

ESI-MS (m/e, as (C$_{20}$H$_{27}$ClF$_2$NO$_3$)$^+$): 402

EXAMPLE 7

4-(((2R)-2-((1R)-3,3-difluorocyclopentyl)-2-hydroxy-2-(4-bromophenyl)ethanoyl)oxy)-1,1-dimethylpiperidinium bromide The title compound was prepared by the treating procedures similar to the method of Example 1, using piperidin-4-yl(2R)-2-((1R)-3,3-difluorocyclopentyl)-2-hydroxy-2-(4-bromophenyl)ethanoate. The product was obtained as a colorless solid.

$^1$H-NMR (CD$_3$OD, δ PPM): 1.69–2.33 (10H, m), 3.15 (3H, s), 3.18 (3H, s), 3.22–3.45 (5H, m), 5.04–5.11 (1H, m), 7.52–7.62 (4H, m).

ESI-MS (m/e, as (C$_{20}$H$_{27}$BrF$_2$NO$_3$)$^+$): 446

EXAMPLE 8

4-(((2R)-2-((1R)-3,3-difluorocyclopentyl)-2-hydroxy-2-(2-chlorophenyl)ethanoyl)oxy)-1,1-dimethylpiperidinium bromide The title compound was prepared by the treating procedures similar to the method of Example 1, using piperidin-4-yl(2R)-2-((1R)-3,3-difluorocyclopentyl)-2-hydroxy-2-(2-chlorophenyl)ethanoate. The product was obtained as a colorless solid.

$^1$H-NMR (CD$_3$OD, δ PPM): 1.52–2.32 (10H, m), 3.04 (3H, s), 3.09–3.45 (5H, m), 3.13 (3H, s), 5.05–5.13 (1H, m), 7.29–7.43 (3H, m), 7.76–7.80 (1H, m)

ESI-MS (m/e, as (C$_{20}$H$_{27}$ClF$_2$NO$_3$)$^+$): 402

EXAMPLE 9

4-(((2R)-2-((1R)-3,3-difluorocyclopentyl)-2-hydroxy-2-(2,4-difluorophenyl)ethanoyl)oxy)-1,1-dimethylpiperidinium bromide The title compound was prepared by the treating procedures similar to the method of Example 1, using piperidin-4-yl(2R)-2-((1R)-3,3-difluorocyclopentyl)-2-hydroxy-2-(2,4-difluorophenyl)ethanoate. The product was obtained as a colorless solid.

$^1$H-NMR (CD$_3$OD, δ PPM): 1.70–2.34 (10H, m), 3.16 (3H, s), 3.17 (3H, s), 3.20–3.52 (5H, m), 5.06–5.17 (1H, m), 6.93–7.09 (2H, m), 7.68–7.80 (1H, m)

ESI-MS (m/e, as (C$_{20}$H$_{26}$F$_4$NO$_3$)$^+$): 404

EXAMPLE 10

4-(((2R)-2-((1R)-3,3-difluorocyclopentyl)-2-hydroxy-2-(1,3-benzodioxol-5-yl)ethanoyl)oxy)-1,1-dimethylpiperidinium bromide The title compound was prepared by the treating procedures similar to the method of Example 1, using piperidin-4-yl(2R)-2-((1R)-3,3-difluorocyclopentyl)-2-hydroxy-2-(1,3-benzodioxol-5-yl) ethanoate. The product was obtained as a colorless oily substance.

$^1$H-NMR (CD$_3$OD, δ PPM): 1.67–2.33 (10H, m), 2.95–3.50 (5H, m), 3.15 (3H, s), 3.18 (3H, s), 5.01–5.11 (1H, m), 5.95 (1H, q, J=1.1 Hz), 6.84 (2H, dd, J=0.8 Hz, 7.8 Hz), 7.11 (1H, d, J=7.8 Hz), 7.13 (1H, s)

ESI-MS (m/e, as (C$_{21}$H$_{28}$F$_2$NO$_5$)$^+$): 412

EXAMPLE 11

4-((((2R)-2-((1R)-3,3-difluorocyclopentyl)-2-hydroxy-2-phenylethanoyl)oxy)methyl)-1,1-dimethylpiperidinium bromide The title compound was prepared by the treating procedures similar to the method of Example 1, using piperidin-4-ylmethyl(2R)-2-((1R)-3,3-difluorocyclopentyl)-2-hydroxy-2-phenylethanoate. The product was obtained as a colorless oily substance.

$^1$H-NMR (D$_2$O, δ PPM): 1.52–2.26 (11H, m), 2.99 (3H, s), 3.15 (3H, s), 3.20–3.51 (5H, m), 4.02–4.22 (2H, m), 7.23–7.42 (3H, m), 7.58–7.68 (2H, m)

ESI-MS (m/e, as (C$_{21}$H$_{30}$F$_2$NO$_3$)$^+$): 382

EXAMPLE 12

4-((((2R)-2-((1R)-3,3-difluorocyclopentyl)-2-hydroxy-2-(4-methylphenyl)ethanoyl)oxy)methyl)-1,1-dimethylpiperidinium bromide The title compound was prepared by the treating procedures similar to the method of Example 1, using piperidin-4-ylmethyl(2R)-2-((1R)-3,3-difluorocyclopentyl)-2-hydroxy-2-(4-methylphenyl)ethanoate. The product was obtained as a colorless oily substance.

$^1$H-NMR (CD$_3$OD, δ PPM): 1.59–2.30 (11H, m), 2.37 (3H, s), 3.03 (3H, s), 3.20 (3H, s), 3.23–3.55 (5H, s), 4.15 (1H, dd, J=5.7 Hz, 10.8 Hz), 4.23 (1H, dd, J=6.0 Hz, 10.8 Hz), 7.23 (2H, d, J=8.2 Hz), 7.53 (2H, d, J=8.2 Hz).

ESI-MS (m/e, as (C$_{22}$H$_{32}$F$_2$NO$_3$)$^+$): 396

EXAMPLE 13

4-((((2R)-2-((1R)-3,3-difluorocyclopentyl)-2-hydroxy-2-(4-ethylphenyl)ethanoyl)oxy)methyl)-1,1-dimethylpiperidinium bromide The title compound was prepared by the treating procedures similar to the method of Example 1, using piperidin-4-ylmethyl(2R)-2-((1R)-3,3-difluorocyclopentyl)-2-hydroxy-2-(4-ethylphenyl)ethanoate. The product was obtained as a colorless oily substance.

$^1$H-NMR (CD$_3$OD, δ PPM): 1.21 (3H, t, J=7.5 Hz), 1.52–2.24 (11H, m), 2.62 (2H, q, J=7.5 Hz), 2.90–3.49 (5H, m), 2.97 (3H, s), 3.13 (3H, s), 4.09 (1H, dd, J=6.3 Hz, 11.4 Hz), 4.16 (1H, dd, J=5.7 Hz, 11.4 Hz), 7.20 (2H, d, J=8.4 Hz), 7.50 (2H, d, J=8.4 Hz)

ESI-MS (m/e, as (C$_{23}$H$_{34}$F$_2$NO$_3$)$^+$): 410

EXAMPLE 14

3-Endo-(((2R)-2-((1R)-3,3-difluorocyclopentyl)-2-hydroxy-2-(4-chlorophenyl)ethanoyl)oxy)-8,8-dimethyl-8-azoniabicyclo[3.2.1]octane bromide The title compound was prepared by the treating procedures similar to the method of Example 1, using 3-endo-8-azabicyclo[3.2.1]oct-3-yl(2R)-2-((1R)-3,3-difluorocyclopentyl)-2-hydroxy-2-(4-chlorophenyl)ethanoate. The product was obtained as a colorless solid.

¹H-NMR (CD₃OD, δ PPM): 1.57–2.32 (12H, m), 2.56–2.72 (2H, m), 3.06 (3H, s), 3.14 (3H, s), 3.21–3.34 (1H, m), 3.72–3.82 (2H, m), 5.06 (1H, t, J=5.9 Hz), 7.40 (2H, d, J=8.8 Hz), 7.60 (2H, d, J=8.8 Hz)

ESI-MS (m/e, as $(C_{22}H_{29}ClF_2NO_3)^+$): 428

EXAMPLE 15

3-Endo-(((2R)-2-((1R)-3,3-difluorocyclopentyl)-2-hydroxy-2-(4-bromophenyl)ethanoyl)oxy)-8.8-dimethyl-8-azoniabicyclo[3.2.1]octane bromide The title compound was prepared by the treating procedures similar to the method of Example 1, using 3-endo-8-azabicyclo[3.2.1]oct-3-yl(2R)-2-((1R)-3,3-difluorocyclopentyl)-2-hydroxy-2-(4-bromophenyl)ethanoate. The product was obtained as a colorless solid.

¹H-NMR (CD₃OD, δ PPM): 1.75–2.30 (12H, m), 2.57–2.72 (2H, m), 3.05 (3H, s), 3.14 (3H, s), 3.20–3.34 (1H, m), 3.72–3.80 (2H, m), 5.07 (1H, t, J=5.7 Hz), 7.55 (4H, s)

ESI-MS (m/e, as $(C_{22}H_{29}BrF_2NO_3)^+$): 472, 474

EXAMPLE 16

(3R)-3-(((2R)-2-((1R)-3,3-difluorocyclopentyl)-2-hydroxy-2-(4-methylphenyl)ethanoyl)oxy)-1,1-dimethylpyrrolidinium bromide The title compound was prepared by the treating procedures similar to the method of Example 1, using (3R)-pyrrolidin-3-yl(2R)-2-((1R)-3,3-difluorocyclopentyl)-2-hydroxy-2-(4-methylphenyl)ethanoate. The product was obtained as a colorless oily substance.

¹H-NMR (CD₃OD, δ PPM): 1.65–2.30 (7H, m), 2.31 (3H, s), 2.67–2.82 (1H, m), 3.03 (3H, s), 3.19 (3H, s), 3.20–3.34 (1H, m), 3.53–3.88 (4H, m), 5.44–5.53 (1H, m), 7.20 (2H, d, J=8.6 Hz), 7.46 (2H, d, J=8.6 Hz)

ESI-MS (m/e, as $(C_{20}H_{28}F_2NO_3)^+$): 386

EXAMPLE 17

(3R)-3-(((2R)-2-((1R)-3,3-difluorocyclopentyl)-2-hydroxy-2-(4-fluorophenyl)ethanoyl)oxy)-1,1-dimethylpyrrolidinium bromide The title compound was prepared by the treating procedures similar to the method of Example 1, using (3R)-pyrrolidin-3-yl(2R)-2-((1R)-3,3-difluorocyclopentyl)-2-hydroxy-2-(4-fluorophenyl)ethanoate. The product was obtained as a colorless solid.

¹H-NMR (CD₃OD, δ PPM): 1.52–2.36 (7H, m), 2.69–2.87 (1H, m), 3.10 (3H, s), 3.21 (3H, s), 3.04–3.37 (1H, m), 3.54–3.91 (4H, m), 5.47–5.57 (1H, br), 7.02–7.17 (2H, m), 7.57–7.69 (2H, m)

ESI-MS (m/e, as $(C_{19}H_{25}F_3NO_3)^+$): 372

EXAMPLE 18

(3R)-3-(((2R)-2-((1R)-3,3-difluorocyclopentyl)-2-hydroxy-2-(4-chlorophenyl)ethanoyl)oxy)-1,1-dimethylpyrrolidinium bromide The title compound was prepared by the treating procedures similar to the method of Example 1, using (3R)-pyrrolidin-3-yl(2R)-2-((1R)-3,3-difluorocyclopentyl)-2-hydroxy-2-(4-chlorophenyl)ethanoate. The product was obtained as a colorless solid.

¹H-NMR (CD₃OD, δ PPM): 1.62–2.35 (7H, m), 2.70–2.85 (1H, m), 3.12 (3H, s), 3.18–3.28 (11H, m), 3.22 (3H, s), 3.56–3.69 (2H, m), 3.70–3.82 (1H, m), 3.84–3.93 (1H, m), 5.52 (1H, brs), 7.39 (2H, d, J=8.7 Hz), 7.61 (2H, d, J=8.7 Hz)

ESI-MS (m/e, as $(C_{19}H_{25}ClF_2NO_3)^+$): 388

EXAMPLE 19

(3R)-3-(((2R)-2-((1R)-3,3-difluorocyclopentyl)-2-hydroxy-2-(4-bromophenyl)ethanoyl)oxy)-1,1-dimethylpyrrolidinium bromide The title compound was prepared by the treating procedures similar to the method of Example 1, using (3R)-pyrrolidin-3-yl(2R)-2-((1R)-3,3-difluorocyclopentyl)-2-hydroxy-2-(4-bromophenyl)ethanoate. The product was obtained as a colorless solid.

¹H-NMR (CD₃OD, δ PPM): 1.64–2.35 (7H, m), 2.70–2.85 (1H, m), 3.11 (3H, s), 3.17–3.26 (1H, m), 3.21 (3H, s), 3.57–3.68 (2H, m), 3.88 (1H, dd, J=6.3 Hz, 13.8 Hz), 5.48–5.56 (1H, m), 7.54 (4H, s)

ESI-MS (m/e, as $(C_{19}H_{25}BrF_2NO_3)^+$): 432, 434

EXAMPLE 20

(3S)-3-(((2R)-2-((1R)-3,3-difluorocyclopentyl)-2-hydroxy-2-(4-fluorophenyl)ethanoyl)oxy)-1,1-dimethylpyrrolidinium bromide The title compound was prepared by the treating procedures similar to the method of Example 1, using (3S)-pyrrolidin-3-yl(2R)-2-((1R)-3,3-difluorocyclopentyl)-2-hydroxy-2-(4-fluorophenyl)ethanoate. The product was obtained as a colorless solid.

¹H-NMR (CD₃OD, δ PPM): 1.57–2.30 (7H, m), 2.68–2.86 (1H, m), 3.11 (3H, s), 3.22 (3H, s), 3.13–3.39 (1H, m), 3.51–3.94 (4H, m), 5.47–5.67 (1H, br), 7.03–7.17 (2H, m), 7.57–7.70 (2H, m)

ESI-MS (m/e, as $(C_{19}H_{25}F_3NO_3)^+$): 372

EXAMPLE 21

(3S)-3-(((2R)-2-((1R)-3,3-difluorocyclopentyl)-2-hydroxy-2-(4-chlorophenyl)ethanoyl)oxy)-1,1-dimethylpyrrolidinium bromide The title compound was prepared by the treating procedures similar to the method of Example 1, using (3S)-pyrrolidin-3-yl(2R)-2-((1R)-3,3-difluorocyclopentyl)-2-hydroxy-2-(4-chlorophenyl)ethanoate. The product was obtained as a colorless solid.

¹H-NMR (CD₃OD, δ PPM): 1.62–2.30 (7H, m), 2.67–2.83 (1H, m), 3.11 (3H, s), 3.07–3.27 (1H, m), 3.22 (3H, s), 3.53–3.93 (4H, m), 5.46–5.57 (1H, m), 7.39 (2H, d, J=8.7 Hz), 7.60 (2H, d, J=8.7 Hz)

ESI-MS (m/e, as $(C_{19}H_{25}ClF_2NO_3)^+$): 388

EXAMPLE 22

(3S)-3-(((2R)-2-((1R)-3,3-difluoroxyclopentyl)-2-hydroxy-2-(4-bromophenyl)ethanoyl)oxy)-1,1-dimethylpyrrolidinium bromide The title compound was prepared by the treating procedures similar to the method of Example 1, using (3S)-pyrrolidin-3-yl(2R)-2-((1R)-3,3-difluorocyclopentyl)-2-hydroxy-2-(4-bromophenyl)ethanoate. The product was obtained as a colorless solid.

¹H-NMR (CD₃OD, δ PPM): 1.61–2.31 (7H, m), 2.70–2.85 (1H, m), 3.11 (3H, s), 3.16–3.26 (1H, m), 3.23 (3H, s), 3.56–3.89 (3H, m), 3.90 (1H, dd, J=6.3 Hz, 13.6 Hz), 5.47–5.57 (1H, m), 7.54 (4H, s)

ESI-MS (m/e, as $(C_{19}H_{25}BrF_2NO_3)^+$): 432, 434

EXAMPLE 23

4-((((2R)-2-((1R)-3,3-difluorocyclopentyl)-2-hydroxy-2-phenylethanoyl)oxy)methyl)-1,1-dimethyl-1,2,3,6-tetrahydropyridinium bromide The title compound was prepared by the treating procedures similar to the method of Example 1, using 1,2,3,6-tetrahydropyridin-4-ylmethyl(2R)-2-((1R)-3,3-difluorocyclopentyl)-2-hydroxy-2-phenylethanoate. The product was obtained as a colorless oily substance.

$^1$H-NMR (CD$_3$OD, δ PPM): 1.58–2.45 (m, 8H), 3.06 (s, 3H), 3.07 (s, 13H), 3.19–3.48 (m, 2H), 3.45 (t, J=6.3 Hz, 2H), 3.89 (brs, 2H), 4.66 (ABq, J=13.1 Hz, 1H), 4.71 (ABq, J=13.1 Hz, 1H), 5.62 (brs, 1H), 7.22–7.43 (m, 3H), 7.55–7.68 (m, 2H)

ESI-MS (m/e, as (C$_{21}$H$_{28}$F$_2$NO$_3$)$^+$): 380

EXAMPLE 24

4-(2-(((2R)-2-((1R)-3,3-difluorocyclopentyl)-2-hydroxy-2-phenylethanoyl)oxy)ethyl)-1,1-dimethyl-1,2,3,6-tetrahydropyridinium bromide The title compound was prepared by the treating procedures similar to the method of Example 1, using 2-(1,2,3,6-tetrahydropyridin-4-yl)ethyl(2R)-2-((1R)-3,3-difluorocyclopentyl)-2-hydroxy-2-phenylethanoate. The product was obtained as a colorless oily substance.

$^1$H-NMR (CD$_3$OD, δ PPM): 1.50–2.53 (10H, m), 2.98 (3H, s), 3.02 (3H, s), 3.10–3.68 (5H, m), 4.21–4.47 (2H, m), 5.04 (1H, brs), 7.23–7.50 (3H, m), 7.50–7.77 (2H, m)

ESI-MS (m/e, as (C$_{22}$H$_{30}$F$_2$NO$_3$)$^+$): 394

EXAMPLE 25

9-((2R)-2-((1R)-3,3-difluorocyclopentyl)-2-hydroxy-2-phenylethanoyl)oxy-3,3-dimethyl-3-azoniabicyclo[3.3.1]nonane iodide (Step 1)

Synthesis of 3-methyl-3-azabicyclo[3.3.1]non-9-yl(2R)-2-((1R)-3,3-difluorocyclopentyl)-2-hydroxy-2-phenylethanoate Using 3-azabicyclo[3.3.1]non-9-yl(2R)-2-((1R)-3,3-difluorocyclopentyl)-2-hydroxy-2-phenylethanoate, the treatments similar to Example 1, (Step 1) were repeated. The resulting two kinds of diastereomers were separated with a preparative thin layer chromatography (Kieselgel™60F$_{254}$, Art5744 (Merck), chloroform/methanol=10/1), and as the low polar substance the title compound, which was named (9endo*)-body for expediency, and as the high polar substance the title compound, which was named (9exo*)-body for expediency, were obtained.

(Step 2)

Synthesis of 9-((2R)-2-((1R)-3,3-difluorocyclopentyl)-2-hydroxy-2-phenylethanoyl)oxy-3,3-dimethyl-3-azoniabicyclo[3.3.1]nonane iodide Each of the diastereomers of 3-methyl-3-azabicyclo[3.3.1]non-9-yl(2R)-2-((1R)-3,3-difluorocyclopentyl)-2-hydroxy-2-phenylethanoate was dissolved in 0.5 ml of methyl iodide and heated under reflux for 12 hours. Thereafter the excessive reagent was distilled off under reduced pressure. The residue was purified on a preparative thin layer chromatography (Aluminiumoxide™60F$_{254}$, Art5713 (Merck), chloroform/methanol=20/1) to provide the title compound whose (9endo**)-body was obtained from the (9endo*)-body, and (9exo**)-body, from the (9exo*)-body, both as colorless, oily substances.

(9endo**)-body $^1$H-NMR (CDCl$_3$, δ PPM): 1.21–2.37 (12H, m), 2.37–2.56 (1H, br), 2.56–2.74 (1H, br), 3.17–3.33 (1H, m), 3.57–3.83 (2H, m), 3.70 (3H, s), 3.72 (3H, s), 3.92 (1H, d, J=3.3 Hz), 4.27 (1H, dd, J=9.4, 13.9 Hz), 4.35–4.50 (1H, m), 5.42–5.53 (1H, m), 7.20–7.42 (3H, m), 7.50–7.66 (2H, d, J=7.0 Hz)

ESI-MS (m/e, as (C$_{23}$H$_{32}$F$_2$NO$_3$)$^+$): 408

(9exo**)-body $^1$H-NMR (CDCl$_3$, δ PPM): 1.41–2.43 (13H, m), 2.60–2.71 (1H, br), 3.10–3.42 (2H, m), 3.31 (3H, s), 3.42–3.65 (2H, m), 3.60 (3H, s), 3.90–4.02 (1H, m), 4.54 (1H, s), 4.92–5.00 (1H, m), 7.22–7.45 (3H, m), 7.53–7.64 (2H, m)

ESI-MS (m/e, as (C$_{23}$H$_{32}$F$_2$NO$_3$)$^+$): 408

EXAMPLE 26

3-Exo-((((2R)-2-((1R)-3,3-difluorocyclopentyl)-2-hydroxy-2-phenylethanoyl)oxy)methyl)-8,8-dimethyl-8-azoniabicyclo[3.2.1]octane bromide The title compound was prepared by the procedures similar to the method of Example 1, using 3-exo-8-azabicyclo[3.2.1]oct-3-ylmethyl(2R)-2-((1R)-3,3-difluorocyclopentyl)-2-hydroxy-2-phenylethanoate. The product was obtained as a colorless solid.

$^1$H-NMR (CDCl$_3$, δ PPM): 1.50–2.55 (15H, m), 3.10–3.40 (1H, m), 3.24 (3H, s), 3.31 (3H, s), 4.14–4.35 (4H, m), 7.20–7.42 (3H, m), 7.50–7.65 (2H, m)

ESI-MS (m/e, as (C$_{23}$H$_{32}$F$_2$NO$_3$)$^+$): 408

EXAMPLE 27

(3S)-3-(((2R)-2-((1R)-3,3-difluorocyclopentyl)-2-hydroxy-2-phenylethanoyl)oxy)methyl)-1,1-dimethylpyrrolidinium bromide The title compound was prepared by the procedures similar to the method of Example 1, using (3S)-pyrrolidin-3-ylmethyl(2R)-2-((1R)-3,3-difluorocyclopentyl)-2-hydroxy-2-phenylethanoate. The product was obtained as a colorless solid.

$^1$H-NMR (CD$_3$OD, δ PPM): 1.60–2.41 (9H, m), 2.92–3.44 (3H, m), 3.11 (6H, s), 4.22–4.28 (2H, m), 7.27–7.45 (3H, m), 7.57–7.67 (2H, m)

ESI-MS (m/e, as (C$_{20}$H$_{28}$F$_2$NO$_3$)$^+$): 368

EXAMPLE 28

(3R)-3-(2-((2R)-2-((1R)-3,3-difluorocyclopentyl)-2-hydroxy-2-phenylethanoyl)oxy)ethyl)-1,1-dimethylpyrrolidinium bromide The title compound was prepared by the procedures similar to the method of Example 1, using 2-((3R)-pyrrolidin-3-yl)ethyl(2R)-2-((1R)-3,3-difluorocyclopentyl)-2-hydroxy-2-phenylethanoate. The product was obtained as a colorless oily substance.

$^1$H-NMR (CD$_3$OD, δ PPM): 1.60–2.30 (10H, m), 2.38–2.52 (1H, m), 2.99 (3H, s), 3.13 (3H, s), 3.20–3.38 (2H, m), 3.48–3.56 (3H, m), 4.14–4.25 (2H, m), 7.28–7.42 (3H, m), 7.57–7.64 (2H, m)

ESI-MS (m/e, as (C$_{21}$H$_{30}$F$_2$NO$_3$)$^+$): 382

EXAMPLE 29

(3S)-3-(2-((2R)-2-((1R)-3,3-difluorocyclopentyl)-2-hydroxy-2-phenylethanoyl)oxy)ethyl)-1,1-dimethylpyrrolidinium bromide The title compound was prepared by the procedures similar to the method of Example 1, using 2-((3S)-pyrrolidin-3-yl)ethyl(2R)-2-((1R)-3,3-difluorocyclopentyl)-

2-hydroxy-2-phenylethanoate. The product was obtained as a colorless oily substance.

$^1$H-NMR (CD$_3$OD, δ PPM): 1.60–2.30 (10H, m), 2.38–2.52 (1H, m), 3.03 (3H, s), 3.14 (3H, s), 3.20–3.38 (2H, m), 3.48–3.56 (3H, m), 4.14–4.25 (2H, m), 7.28–7.42 (3H, m), 7.57–7.64 (2H, m)

ESI-MS (m/e, as (C$_{21}$H$_{30}$F$_2$NO$_3$)$^+$): 382

EXAMPLE 30

(3aR,6aS)-5-endo-5-(((2R)-2-((1R)-3,3-difluorocyclopentyl)-2-hydroxy-2-phenylethanoyl)oxy)-2,2-dimethyloctahydrocyclopenta(c)-pyrrolium bromide The title compound was prepared by the procedures similar to the method of Example 1, using (3aR,6aS)-octahydrocyclopenta(c)pyrrol-5-yl(2R)-2-((1R)-3,3-difluorocyclopentyl)-2-hydroxy-2-phenylethanoate. The product was obtained as a colorless solid.

$^1$H-NMR (CD$_3$OD, δ PPM): 1.50–2.20 (12H, m), 2.68 (1H, t, J=10.6 Hz), 2.98 (3H, s), 3.02 (3H, s), 3.03–3.45 (3H, m), 3.46–3.58 (1H, m), 5.41 (1H, t, J=4.5 Hz), 7.30–7.49 (3H, m), 7.49–7.62 (2H, m)

ESI-MS (m/e, as (C$_{22}$H$_{30}$F$_2$NO$_3$)$^+$): 394

EXAMPLE 31

2,4-Cis-4-(((2R)-2-((1R)-3,3-difluorocyclopentyl)-2-hydroxy-2-phenylethanoyl)oxy)-1,1-dimethyl-2-vinylpiperidinium bromide The title compound was prepared by the procedures similar to the method of Example 1, using 2,4-cis-2-vinylpiperidin-4-yl(2R)-2-((1R)-3,3-difluorocyclopentyl)-2-hydroxy-2-phenylethanoate. The product was obtained as a colorless oily substance.

$^1$H-NMR (CD$_3$OD, δ PPM): 1.53–1.71 (1H, m), 1.79–2.29 (9H, m), 3.05 (3H, s), 3.10 (3H, s), 3.14–3.34 (1H, m), 3.46–3.70 (2H, m), 4.06–4.19 (1H, m), 4.99–5.12 (1H, m), 5.59–5.70 (2H, m), 5.83–6.00 (1H, m), 7.22–7.41 (3H, m), 7.56–7.66 (2H, m)

ESI-MS (m/e, as (C$_{22}$H$_{30}$F$_2$NO$_3$)$^+$): 394

EXAMPLE 32

2-(((2R)-2-((1R)-3,3-difluorocyclopentyl)-2-hydroxy-2-phenylethanoyl)oxy)ethyltrimethylammonium bromide The title compound was prepared by the procedures similar to the method of Example 1, using 2-aminoethyl (2R)-2-((1R)-3,3-difluorocyclopentyl)-2-hydroxy-2-phenylethanoate. The product was obtained as a colorless oily substance.

$^1$H-NMR (CD$_3$OD, δ PPM): 1.60–2.30 (6H, m), 3.03 (9H, s), 3.18–3.49 (1H, m), 3.60–3.80 (2H, m), 4.50–4.70 (2H, m), 7.22–7.50 (3H, m), 7.55–7.68 (2H, m)

ESI-MS (m/e, as (C$_{18}$H$_{26}$F$_2$NO$_3$)$^+$): 342

EXAMPLE 33

3-(((2R)-2-((1R)-3,3-difluorocyclopentyl)-2-hydroxy-2-phenylethanoyl)oxy)propyltrimethylammonium bromide The title compound was prepared by the procedures similar to the method of Example 1, using 3-aminopropyl (2R)-2-((1R)-3,3-difluorocyclopentyl)-2-hydroxy-2-phenylethanoate. The product was obtained as a colorless oily substance.

$^1$H-NMR (CDCl$_3$, δ PPM): 1.50–2.38 (8H, m), 3.08–3.35 (1H, m), 3.23 (9H, s), 3.55–3.82 (2H, m), 4.10–4.24 (1H, m), 4.30–4.45 (1H, m), 4.82 (1H, brs), 7.22–7.42 (3H, m), 7.58–7.70 (2H, m)

ESI-MS (m/e, as (C$_{19}$H$_{28}$F$_2$NO$_3$)$^+$): 356

EXAMPLE 34

1,3-Trans-3-(((2R)-2-((1R)-3,3-difluorocyclopentyl)-2-hydroxy-2-phenylethanoyl)oxy)cyclobutyltrimethylammonium bromide The title compound was prepared by the procedures similar to the method of Example 1, using 1,3-trans-3-aminocyclobutyl(2R)-2-((1R)-3,3-difluorocyclopentyl)-2-hydroxy-2-phenylethanoate. The product was obtained as a colorless solid.

$^1$H-NMR (CD$_3$OD, δ PPM) 1.54–1.71 (1H, m), 1.80–2.29 (5H, m), 2.32–2.52 (2H, m), 2.81–3.00 (2H, m), 3.07 (9H, s), 3.19–3.40 (1H, m), 4.28–4.41 (1H, m), 5.06–5.16 (1H, m), 7.23–7.41 (3H, m), 7.58–7.66 (2H, m)

ESI-MS (m/e, as (C$_{20}$H$_{28}$F$_2$NO$_3$)$^+$): 368

EXAMPLE 35

1,3-Cis-3-(((2R)-2-((1R)-3,3-difluorocyclopentyl)-2-hydroxy-2-phenylethanoyl)oxy)cyclobutyltrimethylammonium bromide The title compound was prepared by the procedures similar to the method of Example 1, using 1,3-cis-3-aminocyclobutyl(2R)-2-((1R)-3,3-difluorocyclopentyl)-2-hydroxy-2-phenylethanoate. The product was obtained as a colorless oily substance.

$^1$H-NMR (CD$_3$OD, δ PPM): 1.54–2.24 (6H, m), 2.32–2.54 (2H, m), 2.72–2.90 (2H, m), 3.04 (9H, s), 3.12–3.35 (1H, m), 3.78–4.00 (11H, m), 4.72–4.92 (1H, m), 7.24–7.45 (3H, m), 7.56–7.68 (2H, m)

ESI-MS (m/e, as (C$_{20}$H$_{28}$F$_2$NO$_3$)$^+$): 368

EXAMPLE 36

(1S,4S)-4-(((2R)-2-((1R)-3,3-difluorocyclopentyl)-2-hydroxy-2-phenylethanoyl)oxy)-2-cyclopentenyltrimethylammonium bromide The title compound was prepared by the procedures similar to the method of Example 1, using (1S,4S)-4-amino-2-cyclopentenyl(2R)-2-((1R)-3,3-difluorocyclopentyl)-2-hydroxy-2-phenylethanoate. The product was obtained as a colorless oily substance.

$^1$H-NMR (CD$_3$OD, δ PPM): 1.52–2.28 (7H, m), 2.63–2.78 (1H, m), 3.07 (9H, s), 3.08–3.30 (1H, m), 4.75–4.92 (1H, m), 5.82–5.91 (1H, m), 6.30–6.50 (2H, m), 7.22–7.40 (3H, m), 7.52–7.62 (2H, m)

ESI-MS (m/e, as (C$_{21}$H$_{28}$F$_2$NO$_3$)$^+$): 380

EXAMPLE 37

(1R,3R)-3-(((2R)-2-((1R)-3,3-difluorocyclopentyl)-2-hydroxy-2-phenylethanoyl)oxy)cyclopentyltrimethylammonium bromide The title compound was prepared by the procedures similar to the method of Example 1, using (1S,3S)-3-aminocyclopentyl(2R)-2-((1R)-3,3-difluorocyclopentyl)-2-hydroxy-2-phenylethanoate. The product was obtained as a colorless oily substance.

$^1$H-NMR (CD$_3$OD, δ PPM): 1.55–2.30 (12H, m), 3.07 (9H, s), 3.18–3.35 (1H, m), 3.91–4.09 (1H, m), 5.25–5.33 (1H, m), 7.25–7.42 (3H, m), 7.54–7.66 (2H, m)

ESI-MS (m/e, as (C$_{21}$H$_{30}$F$_2$NO$_3$)$^+$): 382

EXAMPLE 38

4-(((2R)-2-((1R)-3,3-difluorocyclopentyl)-2-hydroxy-2-(4-chlorophenyl)ethanoyl)oxy)-1,1-diethylpiperidinium iodide (Step 1)

Synthesis of 1-ethylpiperidin-4-yl(2R)-((1R)-3,3-difluorocyclopentyl)-2-hydroxy-2-(4-chlorophenyl)ethanoate To a solution of 25 mg of piperidin-4-yl(2R)-((1R)-3,3-difluorocyclopentyl)-2-hydroxy-2-(4-chlorophenyl)ethanoate in 1 ml of methanol, 50 mg of acetaldehyde and 10 mg of sodium cyanoborohydride were added at room temperature, followed by two hours' stirring at the same temperature. The reaction liquid was diluted with chloroform, washed successively with saturated sodium hydrogencarbonate solution and with saturated brine, and dried over anhydrous sodium sulfate. Distilling the solvent off under reduced pressure, the residue was purified on preparative thin layer chromatography (Kieselgel™60F$_{254}$, Art5744 (Merck), chloroform/methanol=10/1) to provide the title compound.

(Step 2)

Synthesis of 4-(((2R)-2-((1R)-3,3-difluorocyclopentyl)-2-hydroxy-2-(4-chlorophenyl)ethanoyl)oxy)-1,1-diethylpiperidinium iodide A solution formed by dissolving 1-ethylpiperidin-4-yl (2R)-((1R)-3,3-difluorocyclopentyl)-2-hydroxy-2-(4-chlorophenyl)ethanoate in 1 ml of ethyl iodide at room temperature was stirred for 12 hours at 70° C. Excessive reagent was distilled off under reduced pressure, and the residue was purified on preparative thin layer chromatography (Aluminiumoxide™60F$_{254}$, Art5713 (Merck), chloroform/methanol=3/1) to provide 14 mg of the title compound as a colorless solid.

$^1$H-NMR (CD$_3$OD, δ PPM): 1.23–1.34 (6H, m), 1.50–2.30 (10H, m), 3.09–3.57 (9H, m), 5.04–5.12 (1H, m), 7.30–7.43 (2H, m), 7.57–7.67 (2H, m) ESI-MS (m/e, as (C$_{22}$H$_{31}$ClF$_2$NO$_3$)$^+$): 430

EXAMPLE 39

1-Cycloheptylmethyl-4-(((2R)-2-((1R)-3,3-difluorocyclopentyl)-2-hydroxy-2-phenylethanoyl)oxy)-1-methylpiperidinium iodide (Step 1)

Synthesis of 1-(cycloheptylmethyl)piperidin-4-yl(2R)-((1R)-3,3-difluorocyclopentyl)-2-hydroxy-2-phenylethanoate To a solution of 9.3 mg of piperidin-4-yl(2R)-((1R)-3,3-difluorocyclopentyl)-2-hydroxy-2-phenylethanoate in 1 ml of methanol, 10 mg of cycloheptanecarbaldehyde and then 0.5 ml of advancedly prepared 0.3 M methanol solution of sodium cyanoborohydride and zinc chloride (1:0.5) were added at room temperature, followed by 30 minutes' stirring at the same temperature. The reaction liquid was diluted with ethyl acetate, washed successively with saturated sodium hydrogencarbonate solution and with saturated brine, and dried over anhydrous sodium sulfate. Distilling the solvent off under reduced pressure, the residue was purified on preparative thin layer chromatography (Kieselgel™60F$_{254}$, Art5744 (Merck), chloroform/methanol=10/1) to provide the title compound.

(Step 2)

Synthesis of 1-cycloheptylmethyl-4-(((2R)-2-((1R)-3,3-difluorocyclopentyl)-2-hydroxy-2-phenylethanoyl)oxy)-1-methylpiperidinium iodide A solution formed by dissolving 1-(cycloheptylmethyl) piperidin-4-yl(2R)-((1R)-3,3-difluorocyclopentyl)-2-hydroxy-2-phenylethanoate in 0.3 ml of methyl iodide at room temperature was allowed to stand for 12 hours at the same temperature, and excessive reagent was distilled off under reduced pressure. The diastereomers in the residue were separated on preparative thin layer chromatography (Kieselgel™60F$_{254}$ Art5744 (Merck), chloroform/methanol=5/1) to provide the title compound respectively as 3.8 mg (low polar substance) and 2.8 mg (high polar substance) of colorless oily substances.

(Low Polar Substance)

$^1$H-NMR (CD$_3$OD, δ PPM): 0.75–2.31 (23H, m), 2.98–3.67 (7H, m), 3.09 (3H, s), 4.52–5.01 (1H, m), 7.25–7.45 (3H, m), 7.59–7.69 (2H, m)

ESI-MS (m/e, as (C$_{27}$H$_{40}$F$_2$NO$_3$)$^+$): 464

(High Polar Substance)

$^1$H-NMR (CD$_3$OD, δ PPM): 1.00–2.35 (23H, m), 2.95–3.43 (7H, m), 3.06 (3H×6/7, s), 3.08 (3H×1/7, s), 5.00–5.10 (1H, m), 7.30–7.48 (3H, m), 7.57–7.68 (2H, m)

ESI-MS (m/e, as (C$_{27}$H$_{40}$F$_2$NO$_3$)$^+$): 464

EXAMPLE 40

(3R)-1-cycloheptylmethyl-3-(((2R)-2-((1R)-3,3-difluorocyclopentyl)-2-hydroxy-2-phenylethanoyl)oxy)-1-methylpyrrolidinium bromide Using (3R)-pyrrolidin-3-yl(2R)-2-((1R)-3,3-difluorocyclopentyl)-2-hydroxy-2-phenylethanoate, two diastereomers of the title compound were prepared through the treatments similar to those in the method of Example 39, both as colorless oily substances.

(Low Polar Substance)

$^1$H-NMR (CD$_3$OD, δ PPM): 1.10–2.30 (21H, m), 2.80–3.03 (1H, m), 3.03 (3H, s), 3.03–3.22 (1H, m), 3.48–3.62 (2H, m), 3.73–3.86 (1H, m), 3.95–4.10 (2H, m), 4.28–4.40 (1H, m), 5.02–5.65 (1H, m), 7.22–7.40 (3H, m), 7.50–7.60 (2H, m)

ESI-MS (m/e, as (C$_{26}$H$_{38}$F$_2$NO$_3$)$^+$): 450

(High Polar Substance)

$^1$H-NMR (CD$_3$OD, δ PPM): 1.18–2.30 (21H, m), 2.88–3.08 (1H, m), 3.38 (3H, s), 3.08–3.42 (2H, m), 3.70–3.92 (2H, m), 4.00–4.15 (1H, m), 4.41–4.60 (1H, m), 5.01–5.14 (1H, m), 7.21–7.40 (3H, m), 7.50–7.60 (2H, m)

ESI-MS (m/e, as (C$_{26}$H$_{38}$F$_2$NO$_3$)$^+$): 450

EXAMPLE 41

3-Endo-(((2R)-2-((1R)-3,3-difluorocyclopentyl)-2-hydroxy-2-phenylethanoyl)oxy)-8-isopropyl-8-methyl-azoniabicyclo[3.2.1]octane bromide (Step 1)

Synthesis of 3-endo-8-isopropyl-8-azabicyclo[3.2.1]oct-3-yl(2R)-2-((1R)-3,3-difluorocyclopentyl)-2-hydroxy-2-phenylethanoate To a solution of 2.13 g of 3-endo-8-azabicyclo[3.2.1]oct-3-yl(2R)-2-((1R)-3,3-difluorocyclopentyl)-2-hydroxy-2-phenylethanoate in 50 ml of methanol, 1 ml of acetone, and then 30 ml of advancedly prepared 0.3 M methanol solution of sodium cyanoborohydride and zinc chloride (1:0.5) were added at room temperature, followed by 3 days stirring at the same temperature. The reaction liquid was diluted with ethyl acetate, washed successively with saturated sodium hydrogencarbonate solution and with saturated brine, and dried over anhydrous sodium sulfate. Distilling the solvent off under reduced pressure, the residue was purified on preparative thin layer chromatography (Kieselgel™60F$_{254}$, Art5744 (Merck), chloroform/methanol=10/1) to provide 2.25 g of the title compound.

(Step 2)

Synthesis of 3-endo-(((2R)-2-((1R)-3,3-difluorocyclopentyl)-2-hydroxy-2-phenylethanoyl)oxy)-8-isopropyl-8-methyl-azoniabicyclo[3.2.1]octane bromide To 2.25 g of 3-endo-8-isopropyl-8-azabicyclo[3.2.1]oct-3-yl(2R)-2-((1R)-3,3-difluorocyclopentyl)-2-hydroxy-2-phenylethanoate, 10 ml of 10% methyl bromide-acetonitrile solution was added at room temperature, followed by 15 hours' standing at the same temperature. Recovering the precipitated solid by filtration, 963 mg of the title compound was prepared as colorless crystals.

$^1$H-NMR (CD$_3$OD, δ PPM): 1.34 (3H, d, J=6.3 Hz), 1.35 (3H, d, J=6.3 Hz), 1.67–2.28 (12H, m), 2.50–2.73 (2H, m), 2.81 (3H, s), 3.21–3.42 (1H, m), 3.80–3.98 (2H, m), 4.00–4.19 (1H, m), 5.05–5.19 (1H, m), 7.28–7.50 (3H, m), 7.55–7.68 (2H, m)

ESI-MS (m/e, as (C$_{24}$H$_{34}$F$_2$NO$_3$)$^+$): 422

EXAMPLE 42

3-Endo-(((2R)-2-((1R)-3,3-difluorocyclopentyl)-2-hydroxy-2-(2,4-difluorophenyl)ethanoyl)oxy)-8-isopropyl-8-methyl-azoniabicyclo[3.2.1]octane bromide Using 3-endo-8-azabicyclo[3.2.1]oct-3-yl(2R)-2-((1R)-3,3-difluorocyclopentyl)-2-hydroxy-2-(2,4-difluorophenyl)ethanoate, the title compound was prepared through the treatments as in the method of Example 41. The product was obtained as colorless crystals.

$^1$H-NMR (CD$_3$OD, δ PPM): 1.36 (6H, d, J=6.3 Hz), 1.70–2.30 (12H, m), 2.54–2.74 (2H, m), 2.82 (3H, s), 3.12–3.35 (1H, m), 3.84–3.98 (2H, m), 4.01–4.20 (1H, m), 5.10–5.21 (1H, m), 6.92–7.10 (2H, m), 7.68–7.80 (1H, m)

ESI-MS (m/e, as (C$_{24}$H$_{32}$F$_4$NO$_3$)$^+$): 458

EXAMPLE 43

3-(((2R)-2-((1R)-3,3-difluorocyclopentyl)-2-hydroxy-2-phenylethanoyl)oxy)propyl(benzyl)dimethylammonium bromide Using 3-(benzylamino)propyl(2R)-2-((1R)-3,3-difluorocyclopentyl)-2-hydroxy-2-phenylethanoate, the title compound was prepared through the treatments as in the method of Example 1. The product was obtained as colorless oily substance.

$^1$H-NMR (CDCl$_3$, δ PPM): 1.52–2.30 (8H, m), 2.98–3.22 (1H, m), 3.08 (3H, s), 3.09 (3H, s), 3.60–3.90 (2H, m), 4.09–4.22 (1H, m), 4.28–4.41 (1H, m), 4.84 (2H, s), 7.18–7.65 (10H, m)

ESI-MS (m/e, as (C$_{25}$H$_{32}$F$_2$NO$_3$)$^+$): 432

EXAMPLE 44

4-(((2R)-2-((1R,3R)-3-fluorocyclopentyl)-2-hydroxy-2-(4-chlorophenyl)ethanoyl)oxy)-1,1-dimethylpiperidinium bromide Using piperidin-4-yl(2R)-2-(4-chlorophenyl)-2-((1R)-3-fluorocyclopentyl)-2-hydroxyethanoate, the title compound was prepared through the treatments as in the method of Example 1. The product was obtained as colorless solid.

$^1$H-NMR (CD$_3$OD, δ PPM): 1.45–2.10 (8H, m), 2.10–2.35 (2H, m), 3.06–3.49 (5H, m), 3.15 (3H, s), 3.19 (3H, s), 4.70–5.18 (2H, m), 7.38 (2H, d, J=8.6 Hz), 7.65 (2H, d, J=8.6 Hz)

ESI-MS (m/e, as (C$_{20}$H$_{28}$ClFNO$_3$)$^+$): 384

EXAMPLE 45

(2R)-2-(((2R)-2-((1R)-3,3-difluorocyclopentyl)-2-hydroxy-2-phenylethanoyl)oxy)-8-oxa-5-azoniaspiro[4.5]decane chloride To an acetonitrile solution containing 11 mg of (3R)-pyrrolidin-3-yl(2R)-2-((1R)-3,3-difluorocyclopentyl)-2-hydroxy-2-phenylethanoate, 30 mg of 1-chloro-2-(2-chloroethoxy)ethane was added at room temperature, followed by 12 hours' heating under reflux. Distilling the solvent off under reduced pressure, the residue was purified on preparative thin layer chromatography (Aluminiumoxide™60F$_{254}$ Art5713 (Merck), chloroform/methanol=10/1) to provide 2.8 mg of the title compound as a colorless oily substance.

$^1$H-NMR (CD$_3$OD, δ PPM): 1.50–2.80 (8H, m), 3.00–4.03 (13H, m), 5.45–5.60 (1H, m), 7.24–7.70 (5H, m)

ESI-MS (m/e, as (C$_{21}$H$_{28}$F$_2$NO$_4$)$^+$): 396

EXAMPLE 46

(2R)-2-(((2R)-2-((1R)-3,3-difluorocyclopentyl)-2-hydroxy-2-phenylethanoyl)oxy)-5-azoniaspiro[4.5]decane bromide Using 1,5-dibromopentane, the title compound was prepared through the treatments as in the method of Example 45. The product was obtained as a colorless oily substance.

$^1$H-NMR (CDCl$_3$, δ PPM): 1.48–2.40 (13H, m), 2.83–3.35 (4H, m), 3.66–4.40 (6H, m), 5.50–5.68 (1H, m), 7.20–7.41 (3H, m), 7.48–7.65 (2H, m)

ESI-MS (m/e, as (C$_{22}$H$_{30}$F$_2$NO$_3$)$^+$): 394

EXAMPLE 47

(2R)-2-(((2R)-2-((1R)-3,3-difluorocyclopentyl)-2-hydroxy-2-phenylethanoyl)oxy)-5-azoniaspiro[4.4]nonane bromide Using 1,4-dibromobutane, the title compound was prepared through the treatments as in the method of Example 45. The product was obtained as a colorless oily substance.

$^1$H-NMR (CDCl$_3$, δ PPM): 1.50–2.40 (11H, m), 2.75–2.94 (1H, m), 3.10–3.25 (1H, m), 3.35–4.03 (7H, m), 4.32–4.45 (1H, m), 4.75–5.05 (1H, m), 5.50–5.62 (1H, m), 7.22–7.40 (3H, m), 7.50–7.64 (2H, m)

ESI-MS (m/e, as (C$_{21}$H$_{28}$F$_2$NO$_3$)$^+$): 380

EXAMPLE 48

1-(Iminomethyl)piperidin-4-yl(2R)-2-((1R)-3,3-difluorocyclopentyl)-2-hydroxy-2-(4-bromophenyl)-ethanoate monohydrochloride To a solution of 13 mg of piperidin-4-yl(2R)-2-((1R)-3,3-difluorocyclopentyl)-2-hydroxy-2-(4-bromophenyl)ethanoate in 1 ml of anhydrous ethanol, 4 mg of ethyl formimidate hydrochloride was added, followed by 13 hours' stirring at room temperature. The reaction liquid was condensed to dry solid. Purifying the crude product on silica gel column chromatography (eluent: chloroform/methanol=10/1), 9 mg of the title compound was obtained as a colorless solid.

$^1$H-NMR (CD$_3$OD, δ ppm): 1.63–2.25 (10H, m), 3.20–3.77 (5H, m), 5.09–5.17 (1H, m), 7.49–7.60 (4H, m), 7.86 (1H, s)

ESI-MS (m/e, as (C$_{19}$H$_{23}$BrF$_2$N$_2$O$_3$)$^+$): 445, 447

EXAMPLE 49

(1-(Iminomethyl)piperidin-4-yl)methyl(2R)-2-((1R)-3,3-difluorocyclopentyl)-2-hydroxy-2-phenylethanoate monohydrochloride Using piperidin-4-ylmethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.05–2.27 (1H, m), 3.00–3.45 (3H, m), 3.66–3.82 (1H, m), 3.89–4.18 (3H, m), 7.21–7.44 (3H, m), 7.53–7.64 (2H, m), 7.81 (1H, s)

ESI-MS (m/e, as (C$_{20}$H$_{26}$F$_2$N$_2$O$_3$+H)$^+$): 381

EXAMPLE 50

(1-(Iminomethyl)piperidin-4-yl)methyl(2R)-2-((1R)-3,3-difluorocyclopentyl)-2-hydroxy-2-(4-ethylphenyl)ethanoate monohydrochloride Using piperidin-4-ylmethyl(2R)-2-((1R)-3,3-difluorocyclopentyl)-2-hydroxy-2-(4-ethylphenyl)ethanoate, the title compound was prepared through the treatments as in the method of Example 48. The product was obtained as a colorless oily substance.

$^1$H-NMR (CD$_3$OD, δ ppm): 1.16–1.42 (2H, m), 1.22 (3H, t, J=7.5 Hz), 1.66–2.2 (9H, m), 2.63 (2H, q, J=7.5 Hz), 3.002–3.44 (3H, m), 3.73–3.83 (1H, m), 3.89–4.14 (3H, m), 7.19 (2H, d, J=8.4 Hz), 7.49 (2H, d, J-8.4 Hz), 7.83 (1H, s)

ESI-MS (m/e, as (C$_{22}$H$_{30}$F$_2$N$_2$O$_3$+H)$^+$): 409

EXAMPLE 51

(1-(Iminomethyl)piperidin-4-yl)methyl(2R)-2-((1R)-3,3-difluorocyclopentyl)-2-hydroxy-2-(4-vinylphenyl)ethanoate monohydrochloride Using piperidin-4-ylmethyl(2R)-2-((1R)-3,3-difluorocyclopentyl)-2-hydroxy-2-(4-vinylphenyl)ethanoate, the title compound was prepared through the treatments as in the method of Example 48. The product was obtained as a colorless oily substance.

$^1$H-NMR (CD$_3$OD, δ ppm): 1.16–1.42 (2H, m), 1.22 (3H, t, J=7.5 Hz), 1.66–2.2 (9H, m), 2.63 (2H, q, J=7.5 Hz), 3.002–3.44 (3H, m), 3.73–3.83 (1H, m), 3.89–4.14 (3H, m), 7.19 (2H, d, J=8.4 Hz), 7.49 (2H, d, J=8.4 Hz), 7.83 (1H, s)

ESI-MS (m/e, as (C$_{20}$H$_{26}$F$_2$N$_2$O$_3$+H)$^+$): 409

EXAMPLE 52

(1-(Iminomethyl)piperidin-4-yl)methyl(2R)-2-((1R)-3,3-difluorocyclopentyl)-2-hydroxy-2-(4-chlorophenyl)ethanoate monohydrochloride Using piperidin-4-ylmethyl(2R)-2-((1R)-3,3-difluorocyclopentyl)-2-hydroxy-2-(4-chlorophenyl)ethanoate, the title compound was prepared through the treatments as in the method of Example 48. The product was obtained as a colorless solid.

$^1$H-NMR (CD$_3$OD, δ ppm): 0.80–2.22 (11H, m), 2.89–3.49 (3H, m), 3.70–4.17 (4H, m), 7.36 (2H, d, J=8.6 Hz), 7.60 (2H, d, J=8.6 Hz), 7.84 (1H, s)

ESI-MS (m/e, as (C$_{20}$H$_{25}$ClF$_2$N$_2$O$_3$+H)$^+$): 415

EXAMPLE 53

(1-(Iminomethyl)piperidin-4-yl)methyl(2R)-2-((1R)-3,3-difluorocyclopentyl)-2-hydroxy-2-(4-bromophenyl)ethanoate monohydrochloride Using piperidin-4-ylmethyl(2R)-2-((1R)-3,3-difluorocyclopentyl)-2-hydroxy-2-(4-bromophenyl)ethanoate, the title compound was prepared through the treatments as in the method of Example 48. The product was obtained as a colorless solid.

$^1$H-NMR (CD$_3$OD, δ ppm): 1.18–1.43 (2H, m), 1.62–2.25 (9H, m), 3.03–3.46 (3H, m), 3.74–3.84 (1H, m), 3.92–4.14 (3H, m), 7.47–7.62 (4H, m), 7.83 (1H, s)

ESI-MS (m/e, as (C$_{20}$H$_{25}$BrF$_2$N$_2$O$_3$+H)$^+$): 459, 461

EXAMPLE 54-1

2-(1-(Iminomethyl)piperidin-4-yl)ethyl(2R)-2-((1R)-3,3-difluorocyclopentyl)-2-hydroxy-2-phenylethanoate monohydrochloride Using 2-(piperidin-4-yl)ethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.00–2.25 (13H, m), 2.82–3.02 (1H, m), 3.10–3.40 (2H, m), 3.65–3.80 (1H, m), 3.85–4.00 (1H, m), 4.10–4.30 (2H, m), 7.25–7.45 (3H, m), 7.58–7.70 (2H, m), 7.80 (1H, s)

ESI-MS (m/e, as (C$_{21}$H$_{28}$F$_2$N$_2$O$_3$+H)$^+$): 395

EXAMPLE 54-2

(Salt Exchange)

2-(1-(Iminomethyl)piperidin-4-yl)ethyl(2R)-2-((1R)-3,3-difluorocyclopentyl)-2-hydroxy-2-phenylethanoate monohydrobromide A solution of 50 mg of 2-(1-(iminomethyl)piperidin-4-yl)ethyl(2R)-2-((1R)-3,3-difluorocyclopentyl)-2-hydroxy-2-phenylethanoate monohydrochloride in 2 ml of ultrapure water was developed on reversed phase medium pressure liquid chromatography [ODS-AQ 120-S50 (YMC Co.)], and 60 ml of 0.2 M aqueous sodium bromide solution was flowed. After washing with 100 ml of ultrapure water, the title compound was eluted from tetrahydrofuran/water=1/5, and 35 mg thereof was obtained as a colorless solid upon condensation to dry solid.

EXAMPLE 54-3

(Salt Exchange)

2-(1-(Iminomethyl)piperidin-4-yl)ethyl(2R)-2-((1R)-3,3-difluorocyclopentyl)-2-hydroxy-2-phenylethanoate monophosphate A solution of 7.0 g of 2-(1-(iminomethyl)piperidin-4-yl)ethyl(2R)-2-((1R)-3,3-difluorocyclopentyl)-2-hydroxy-2-phenylethanoate monohydrochloride in 50 ml of ultrapure water was developed on reversed phase medium pressure liquid chromatography [ODS-AQ 120-S50 (YMC Co.)], and 300 ml of 1.0 M aqueous sodium dihydrogenephosphate solution, 300 ml of 0.2 M phosphoric acid and 300 ml of ultrapure water were flowed by the order stated, followed by elution with tetrahydrofuran/water=1/9. Distilling the solvent off under reduced pressure, the residue was crystallized in ethanol and recovered by filtration, to provide 6.5 g of the title compound as a colorless solid.

EXAMPLE 54-4

(Salt Exchange)

2-(1-(Iminomethyl)piperidin-4-yl)ethyl(2R)-2-((1R)-3,3-difluorocyclopentyl)-2-hydroxy-2-phenylethanoate fumarate A solution of 75 mg g of 2-(1-(iminomethyl)piperidin-4-yl)ethyl(2R)-2-((1R)-3,3-difluorocyclopentyl)-2-hydroxy-2-phenylethanoate monohydrochloride in 2 ml of ultrapure water was developed on reversed phase medium pressure liquid chromatography [ODS-AQ 120-S50 (YMC Co.)], and 60 ml of 0.2 M aqueous sodium monofumarate solution, 60 ml of aqueous fumaric acid solution and 100 ml of ultrapure water were flowed by the order stated. The title compound was eluted from tetrahydrofuran/water=1/4. Condensing the same to dry solid, 41 mg of a colorless solid was obtained.

EXAMPLE 55

2-(1-(Iminomethyl)piperidin-4-yl)ethyl(2R)-2-((1R)-3,3-difluorocyclopentyl)-2-hydroxy-2-(4-chlorophenyl)ethanoate monohydrochloride Using 2-(piperidin-4-yl)ethyl(2R)-2-((1R)-3,3-difluorocyclopentyl)-2-hydroxy-2-(4-chlorophenyl)ethanoate, the title compound was prepared through the treatments as in the method of Example 48. The product was obtained as a colorless oily substance.

$^1$H-NMR (CD$_3$OD, δ ppm): 1.10–2.23 (13H, m), 2.89–3.30 (3H, m), 3.70–3.80 (1H, m), 3.90–4.00 (1H, m), 4.16–4.30 (2H, m), 7.35–7.40 (2H, m), 7.58–7.63 (2H, m), 7.81 (1H, brs)

ESI-MS (m/e, as (C$_2$H$_{27}$ClF$_2$N$_2$O$_3$+H)$^+$): 429

EXAMPLE 56

2-(1-(Iminomethyl)piperidin-4-yl)ethyl(2R)-2-((1R)-3,3-difluorocyclopentyl-2-hydroxy-2-(4-bromophenyl)ethanoate monohydrochloride Using 2-(piperidin-4-yl)ethyl(2R)-2-((1R)-3,3-difluorocyclopentyl)-2-hydroxy-2-(4-bromophenyl)ethanoate, the title compound was prepared through the treatments as in the method of Example 48. The product was obtained as a colorless oily substance.

$^1$H-NMR (CD$_3$OD, δ ppm): 1.12–2.24 (13H, m), 2.90–3.03 (1H, m), 3.16–3.28 (2H, m), 3.70–3.81 (1H, m), 3.90–4.01 (1H, m), 4.16–4.30 (2H, m), 7.54 (4H, brs), 7.81 (1H, s)

ESI-MS (m/e, as (C$_2$H$_{27}$BrF$_2$N$_2$O$_3$+H)$^+$): 473, 475

EXAMPLE 57

3-(1-(Iminomethyl)piperidin-4-yl)propyl(2R)-2-((1R)-3,3-difluorocyclopentyl)-2-hydroxy-2-phenylethanoate monohydrochloride Using 3-(piperidin-4-yl)propyl(2R)-2-((1R)-3,3-difluorocyclopentyl)-2-hydroxy-2-phenylethanoate, the title compound was prepared through the treatments as in the method of Example 48. The product was obtained as a colorless solid.

$^1$H-NMR (CD$_3$OD, δ PPM): 0.85–2.30 (15H, m), 2.99–3.44 (3H, m), 3.71–4.01 (2H, m), 4.16 (2H, t, J=6.3 Hz), 7.23–7.65 (5H, m), 7.83 (1H, s)

ESI-MS (m/e, as (C$_{22}$H$_{30}$F$_2$N$_2$O$_3$+H)$^+$): 409

EXAMPLE 58

(1-Iminomethyl-1,2,3,6-tetrahydropyridin-4-yl)methyl(2R)-2-((1R)-3,3-difluorocyclopentyl)-2-hydroxy-2-phenylethanoate monohydrochloride Using 1,2,3,6-tetrahydropyridin-4-yl-methyl(2R)-2-((1R)-3,3-difluorocyclopentyl)-2-hydroxy-2-phenylethanoate, the title compound was prepared through the treatments as in the method of Example 48. The product was obtained as a colorless solid.

$^1$H-NMR (CD$_3$OD, δ ppm): 1.50–2.26 (8H, m), 3.15–3.39 (1H, m), 3.64 (2H, t, J=6.0 Hz), 3.95 (2H×5/7, brs), 4.12 (2H×2/7, brs), 4.54–4.71 (2H, m), 5.65 (1H×5/7, brs), 5.68–5.73 (1H×2/7, m), 7.23–7.47 (3H, m), 7.54–7.73 (2H, m), 7.59 (1H×5/7,s ), 7.97 (1H×2/7,s )

ESI-MS (m/e, as (C$_{20}$H$_{24}$F$_2$N$_2$O$_3$+H)$^+$): 379

EXAMPLE 59

(4-Hydroxy-1-(iminomethyl)piperidin-4-yl)methyl(2R)-2-((1R)-3,3-difluorocyclopentyl)-2-hydroxy-2-phenylethanoate monohydrochloride Using (4-hydroxypiperidin-4-yl)methyl(2R)-2-((1R)-3,3-difluorocyclopentyl)-2-hydroxy-2-phenylethanoate, the title compound was prepared through the treatments as in the method of Example 48. The product was obtained as a colorless solid.

$^1$H-NMR (CD$_3$OD, δ ppm): 1.10–2.30 (10H, m), 3.00–3.50 (3H, m), 3.50–3.3.90 (3H, m), 3.90–4.11 (2H, m), 7.23–7.46 (3H, m), 7.58–7.76 (2H, m), 7.85 (1H, d, J=4.6 Hz)

ESI-MS (m/e, as (C$_{20}$H$_{26}$F$_2$N$_2$O$_4$+H)$^+$): 397

EXAMPLE 60

(1R)-1-(1-(Iminomethyl)piperidin-4-yl)ethyl(2R)-2-((1R)-3,3-difluorocyclopentyl)-2-hydroxy-2-phenylethanoate monohydrochloride Using (1R)-1-(piperidin-4-yl)ethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 0.80–1.40 (6H, m), 1.54–2.30 (10H, m), 2.90–3.15 (1H, m), 3.60–4.02 (2H, m), 4.70–5.05 (1H, m), 7.22–7.46 (3H, m), 7.50–7.70 (2H, m), 7.72–7.85 (11H, m)

ESI-MS (m/e, as (C$_{21}$H$_{28}$F$_2$N$_2$O$_3$+H)$^+$): 395

EXAMPLE 61

2-(1-(iminomethyl)-4-piperidinilidene)ethyl(2R)-2-((1R)-3,3-difluorocyclopentyl)-2-hydroxy-2-phenylethanoate monohydrochloride Using 2-(4-piperidinilidene)ethyl(2R)-2-((1R)-3,3-difluorocyclopentyl)-2-hydroxy-2-phenylethanoate, the title compound was prepared through the treatments as in the method of Example 48. The product was obtained as a colorless solid.

$^1$H-NMR (CD$_3$OD, δ ppm): 1.50–2.53 (12H, m), 3.00–3.65 (5H, m), 4.62–4.77 (2H, m), 5.49–5.60 (1H, m), 7.22–7.42 (3H, m), 7.54–7.66 (2H, m), 7.92 (1H, d, J=5.5 Hz)

ESI-MS (m/e, as (C$_{21}$H$_{26}$F$_2$N$_2$O$_3$+H)$^+$): 393

EXAMPLE 62

2-(1-Iminomethyl-1,2,3,6-tetrahydropiridin-4-yl)ethyl (2R)-2-((1R)-3,3-difluorocyclopentyl)-2-hydroxy-2-phenylethanoate monohydrochloride Using 2-(1,2,3,6-tetrahydropiridin-4-yl)ethyl(2R)-2-((1R)-3,3-difluorocyclopentyl)-2-hydroxy-2-phenylethanoate, the title compound was prepared through the treatments as in the method of Example 48. The product was obtained as a colorless solid.

$^1$H-NMR (CD$_3$OD, δ ppm): 1.52–2.48 (10H, m), 3.10–3.29 (1H, m), 3.46–3.92 (4H, m), 4.19–4.40 (2H, m), 5.20 (1H, brs), 7.23–7.42 (3H, m), 7.54–7.64 (2H, m), 7.85–8.00 (1H, m)

ESI-MS (m/e, as (C$_{21}$H$_{26}$F$_2$N$_2$O$_3$+H)$^+$): 393

EXAMPLE 63

2-(4-(Iminomethyl)piperadino)ethyl(2R)-2-((1R)-3,3-difluorocyclopentyl)-2-hydroxy-2-phenylethanoate monohydrochloride Using 2-piperadinoethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.54–2.30 (6H, m), 2.38–2.60 (4H, m), 2.65 (2H, t, J=6.0 Hz), 3.14–3.50 (5H, m), 4.20–4.42 (2H, m), 7.22–7.42 (3H, m), 7.58–7.70 (2H, m) 7.83 (1H, s)

ESI-MS (m/e, as (C$_{20}$H$_{27}$F$_2$N$_3$O$_3$+H)$^+$): 396

EXAMPLE 64

((3R)-1-(iminomethyl)piperidin-3-yl)methyl(2R)-2-((1R)-3,3-difluorocyclopentyl)-2-hydroxy-2-phenylethanoate monohydrochloride Using (3R)-piperidin-3-ylmethyl(2R)-2-((1R)-3,3-difluorocyclopentyl)-2-hydroxy-2-phenylethanoate, the title compound was prepared through the treatments as in the method of Example 48. The product was obtained as a colorless solid.

$^1$H-NMR (CD$_3$OD, δ ppm): 1.20–2.28 (11H, m), 2.80–3.38 (3H, m), 3.60–3.80 (1H, m), 3.80–4.24 (3H, m), 7.24–7.45 (3H, m), 7.55–7.65 (2H, m), 7.65–7.94 (1H, m)

ESI-MS (m/e, as (C$_{20}$H$_{26}$F$_2$N$_2$O$_3$+H)$^+$): 381

EXAMPLE 65

2-((3S)-1-(iminomethyl)piperidin-3-yl)ethyl(2R)-2-((1R)-3,3-difluorocyclopentyl)-2-hydroxy-2-phenylethanoate monohydrochloride Using 2-((3S)-piperidin-3-yl)ethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 0.80–2.25 (13H, m), 2.70–3.12 (2H, m), 3.18–3.40 (1H, m), 3.50–3.92 (2H, m), 4.13–4.35 (2H, m), 7.22–7.40 (3H, m), 7.54–7.90 (3H, m)

ESI-MS (m/e, as (C$_{21}$H$_{28}$F$_2$N$_2$O$_3$+H)$^+$): 395

EXAMPLE 66

2-((3R)-1-(iminomethyl)piperidin-3-yl)ethyl(2R)-2-((1R)-3,3-difluorocyclopentyl)-2-hydroxy-2-phenylethanoate monohydrochloride Using 2-((3R)-piperidin-3-yl)ethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.10–2.25 (13H, m), 2.70–3.12 (2H, m), 3.18–3.40 (1H, m), 3.51–3.90 (2H, m), 4.15–4.32 (2H, m), 7.22–7.40 (3H, m), 7.56–7.90 (3H, m)

ESI-MS (m/e, as (C$_{20}$H$_{26}$F$_2$N$_2$O$_3$+H)$^+$): 381

EXAMPLE 67

(3S)-1-(iminomethyl)pyrrolidin-3-yl(2R)-2-((1R)-3,3-difluorocyclopentyl)-2-hydroxy-2-phenylethanoate monohydrochloride Using (3S)-pyrrolidin-3-yl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.05–2.27 (11H, m), 3.00–3.45 (3H, m), 3.66–3.82 (1H, m), 3.89–4.18 (3H, m), 7.21–7.44 (3H, m), 7.53–7.64 (2H, m), 7.81 (1H, s)

ESI-MS (m/e, as (C$_{21}$H$_{28}$F$_2$N$_2$O$_3$+H)$^+$): 395

EXAMPLE 68

(3R)-1-(iminomethyl)pyrrolidin-3-yl(2R)-2-((1R)-3,3-difluorocyclopentyl)-2-hydroxy-2-phenylethanoate monohydrochloride Using (3R)-pyrrolidin-3-yl(2R)-2-((1R)-3,3-difluorocyclopentyl)-2-hyroxy-2-phenylethanoate, the title compound was prepared through the treatments as in the method of Example 48. The product was obtained as a colorless oily substance.

$^1$H-NMR (CD$_3$OD, δ ppm): 1.58–2.43 (8H, m), 3.15–3.96 (5H, m), 5.35–5.55 (1H, m), 7.24–7.42 (3H, m), 7.55–7.62 (2H, m), 7.93, 8.06 (1H, 2*s)

ESI-MS (m/e, as (C$_{18}$H$_{23}$F$_2$N$_2$O$_3$+H)$^+$): 353

EXAMPLE 69

((3R)-1-(iminomethyl)pyrrolidin-3-yl)methyl(2R)-2-((1R)-3,3-difluorocyclopentyl)-2-hydroxy-2-phenylethanoate monohydrochloride Using ((3R)-pyrrolidin-3-yl)methyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.50–2.26 (8H, m), 2.57–2.84 (1H, m), 3.01–3.85 (5H, m), 4.08–4.36 (2H, m), 7.24–7.40 (3H, m), 7.56–7.63 (2H, m), 7.92–8.03 (1H, m)

ESI-MS (m/e, as (C$_{91}$H$_{25}$F$_2$N$_2$O$_3$+H)$^+$): 367

EXAMPLE 70

((3S)-1-(iminomethyl)pyrrolidin-3-yl)methyl(2R)-2-((1R)-3,3-difluorocyclopentyl)-2-hydroxy-2-phenylethanoate monohydrochloride Using ((3S)-pyrrolidin-3-yl)methyl(2R)-2-((1R)-3,3-difluorocyclopentyl)-2-hydroxy-2-phenylethanoate, the title compound was prepared through the treatments as in the method of Example 48. The product was obtained as a colorless solid.

$^1$H-NMR (CD$_3$OD, δ ppm): 1.59–2.28 (8H, m), 2.62–2.86 (1H, m), 3.08–3.90 (5H, m), 4.13–4.35 (2H, m), 7.26–7.45 (3H, m), 7.57–7.66 (2H, m), 7.93–8.07 (1H, m)

ESI-MS (m/e, as (C$_{20}$H$_{26}$F$_2$N$_2$O$_3$+H)$^+$): 367

EXAMPLE 71

2-((3S)-1-(iminomethyl)pyrrolidin-3-yl)ethyl(2R)-2-((1R)-3,3-difluorocyclopentyl)-2-hydroxy-2-phenylethanoate monohydrochloride Using 2-((3S)-pyrrolidin-3-yl)ethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.50–2.27 (11H, m), 2.89–3.30 (3H, m), 3.40–3.83 (2H, m), 4.17–4.25 (2H, m), 7.25–7.40 (3H, m), 7.57–7.66 (2H, m), 7.92, 7.98 (1H, 2*s)

ESI-MS (m/e, as (C$_{20}$H$_{26}$F$_2$N$_2$O$_3$+H)$^+$): 381

EXAMPLE 72

2-((3R)-1-(iminomethyl)pyrrolidin-3-yl)ethyl(2R)-2-((1R)-3,3-difluorocyclopentyl)-2-hydroxy-2-phenylethanoate monohydrochloride Using 2-((3R)-pyrrolidin-3-yl)ethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.50–2.28 (11H, m), 2.88–3.84 (5H, m), 4.13–4.28 (2H, m), 7.24–7.41 (3H, m), 7.57–7.64 (2H, m), 7.88, 7.97 (1H, 2*s)

ESI-MS (m/e, as (C$_{20}$H$_{26}$F$_2$N$_2$O$_3$+H)$^+$): 381

EXAMPLE 73

((2R)-1-(iminomethyl)pyrrolidin-2-yl)methyl(2R)-2-((1R)-3,3-difluorocyclopentyl)-2-hydroxy-2-phenylethanoate monohydrochloride Using ((2R)-pyrrolidin-2-yl)methyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.57–2.23 (10H, m), 3.14–3.43 (3H, m), 4.15–4.26 (2H, m), 4.31–4.39 (11H, m), 7.28–7.42 (3H, m), 7.54–7.59 (2H, m), 7.93 (1H, s)

ESI-MS (m/e, as (C$_{19}$H$_{25}$F$_2$N$_2$O$_3$+H)$^+$): 367

EXAMPLE 74

1-(Iminomethyl)azetidin-3-yl(2R)-2-((1R)-3,3-difluorocyclopentyl)-2-hydroxy-2-phenylethanoate monohydrochloride Using azetidin-3-yl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.55–2.25 (6H, m), 3.17–3.29 (1H, m), 4.10–4.20 (1H, m), 4.33–4.40 (1H, m), 4.55–4.65 (1H, m), 4.72–4.81 (1H, m), 5.32–5.40 (1H, m), 7.26–7.41 (3H, m), 7.58–7.64 (2H, m), 7.89 (1H, s)

ESI-MS (m/e, as (C$_{17}$H$_{20}$F$_2$N$_2$O$_3$+H)$^+$): 339

EXAMPLE 75

(1-(Iminomethyl)azetidin-3-yl)methyl(2R)-2-((1R)-3,3-difluorocyclopentyl)-2-hydroxy-2-phenylethanoate monohydrochloride Using azetidin-3-ylmethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ ppm): 1.60–2.26 (6H, m), 3.10–3.36 (2H, m), 3.77–3.96 (1H, m), 3.99–4.16 (1H, m), 4.17–4.48 (4H, m), 7.25–7.43 (3H, m), 7.55–7.66 (2H, m), 7.69, 7.72 (1H, 2*s)

ESI-MS (m/e, as (C$_{18}$H$_{23}$F$_2$N$_2$O$_3$+H)$^+$): 353

EXAMPLE 76

2-(1-(Iminomethyl)azetidin-3-yl)ethyl(2R)-2-((1R)-3,3-difluorocyclopentyl)-2-hydroxy-2-phenylethanoate monohydrochloride Using 2-(azetidin-3-yl)ethyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ PPM): 1.55–2.25 (8H, m), 2.71–2.87 (11H, m), 3.14–3.30 (1H, m), 3.84–3.92 (1H, m), 3.97–4.07 (1H, m), 4.13–4.28 (3H, m), 4.32–4.42 (1H, m), 7.26–7.39 (3H, m), 7.56–7.63 (2H, m), 7.74 (1H, brs)

ESI-MS (m/e, as (C$_{19}$H$_{24}$F$_2$N$_2$O$_3$+H)$^+$): 367

EXAMPLE 77

(3aR,6aS)-2-(iminomethyl)octahydrocyclopenta(c)pyrrol-5-yl(2R)-2-((1R)-3,3-difluorocyclopentyl)-2-hydroxy-2-phenylethanoate monohydrochloride Using (3aR,6aS)-octahydrocyclopenta(c)pyrrol-5-yl(2R)-2-((1R)-3,3-difluorocyclopentyl)-2-hydroxy-2-phenylethanoate, the title compound was prepared through the treatments as in the method of Example 48. The product was obtained as a colorless solid.

$^1$H-NMR (CD$_3$OD, δ ppm): 1.50–2.40 (10H, m), 2.78–3.40 (5H, m), 3.58–3.73 (1H, m), 3.79–3.90 (1H, m), 5.16–5.38 (1H, m), 7.24–7.40 (3H, m), 7.50–7.63 (2H, m), 7.80 (1H, d, J=18.9 Hz)

ESI-MS (m/e, as (C$_{21}$H$_{26}$F$_2$N$_2$O$_3$+H)$^+$): 393

EXAMPLE 78

1,3-Trans-3-((iminomethyl)amino)cyclobutyl(2R)-2-((1R)-3,3-difluorocyclopentyl)-2-hydroxy-2-phenylethanoate monohydrochloride Using 1,3-trans-3-aminocyclobutyl(2R)-2-((1R)-3,3-difluorocyclopentyl)-2-hydroxy-2-phenylethanoate, the title compound was prepared through the treatments as in the method of Example 48. The product was obtained as a colorless oily substance.

$^1$H-NMR (CD$_3$OD, δ PPM): 1.51–2.22 (6H, m), 2.35–2.62 (4H, m), 3.10–3.40 (1H, m), 4.13–4.35 (1H, m), 5.00–5.21 (1H, m), 7.20–7.40 (3H, m), 7.50–7.65 (2H, m), 7.70–7.88 (1H, m)

ESI-MS (m/e, as (C$_{18}$H$_{22}$F$_2$N$_2$O$_3$+H)$^+$): 353

EXAMPLE 79

1,4-Trans-4-((iminomethyl)amino)cyclohexyl(2R)-2-((1R)-3,3-difluorocyclopentyl)-2-hydroxy-2-phenylethanoate monohydrochloride Using 1,4-trans-4-aminocyclohexyl(2R)-2-((1R)-3,3-difluorocyclopentyl)-2-hydroxy-2-phenylethanoate, the title compound was prepared through the treatments as in the method of Example 48. The product was obtained as a colorless solid.

¹H-NMR (CD₃OD, δ ppm): 1.00–2.28 (m, 15H), 3.00–3.70 (m, 3H), 4.66–5.07 (m, 1H), 7.22–7.43 (m, 3H), 7.55–7.68 (m, 2H), 7.74 (d, J=0.8 Hz, 1H×7/10), 7.92 (s, 1H×1/7), 8.02 (s, 1H×2/10)

ESI-MS (m/e, as $(C_{20}H_{26}F_2N_2O_3+H)^+$): 381

EXAMPLE 80

1,4-Cis-4-((iminomethyl)amino)cyclohexyl(2R)-2-((1R)-3,3-difluorocyclopentyl)-2-hydroxy-2-phenylethanoate monohydrochloride Using 1,4-cis-4-aminocyclohexyl(2R)-2-((1R)-3,3-difluorocyclopentyl)-2-hydroxy-2-phenylethanoate, the title compound was prepared through the treatments as in the method of Example 48. The product was obtained as a colorless oily substance.

¹H-NMR (CD₃OD, δ ppm): 1.21–2.36 (15H, m), 3.20–3.40 (1H, m), 3.40–3.70 (1H, br), 5.01 (1H, brs), 7.23–7.48 (3H, m), 7.50–7.60 (2H, m), 7.60–8.36 (1H, m)

ESI-MS (m/e, as $(C_{20}H_{26}F_2N_2O_3+H)^+$): 381

EXAMPLE 81

3-((Iminomethyl)amino)propyl(2R)-2-((1R)-3,3-difluorocyclopentyl)-2-hydroxy-2-phenylethanoate monohydrochloride Using 3-aminopropyl(2R)-2-((1R)-3,3-difluorocyclopentyl)-2-hydroxy-2-phenylethanoate, the title compound was prepared through the treatments as in the method of Example 48. The product was obtained as a colorless oily substance.

¹H-NMR (CD₃OD, δ ppm): 1.50–2.26 (8H, m), 3.10–3.42 (3H, m), 4.23 (2H, d, J=6.2 Hz), 7.22–7.48 (3H, m), 7.54–7.90 (3H, m)

ESI-MS (m/e, as $(C_{17}H_{22}F_2N_2O_3+H)^+$): 341

EXAMPLE 82

3-((Iminomethyl)(methyl)amino)propyl(2R)-2-((1R)-3,3-difluorocyclopentyl)-2-hydroxy-2-phenylethanoate monohydrochloride Using 3-(methylamino)propyl(2R)-2-((1R)-3,3-difluorocyclopentyl)-2-hydroxy-2-phenylethanoate, the title compound was prepared through the treatments as in the method of Example 48. The product was obtained as a colorless oily substance.

¹H-NMR (CD₃OD, δ ppm): 1.55–2.30 (8H, m), 2.95 (9/4H, s), 3.07 (3/4H, s), 3.15–3.50 (3H, m), 4.10–4.34 (2H, m), 7.25–7.48 (3H, m), 7.56–7.80 (3H, m)

ESI-MS (m/e, as $(C_{18}H_{24}F_2N_2O_3+H)^+$): 355

EXAMPLE 83

4-((Iminomethyl)amino)butyl(2R)-2-((1R)-3,3-difluorocyclopentyl)-2-hydroxy-2-phenylethanoate monohydrochloride Using 4-aminobutyl(2R)-2-((1R)-3,3-difluorocyclopentyl)-2-hydroxy-2-phenylethanoate, the title compound was prepared through the treatments as in the method of Example 48. The product was obtained as a colorless oily substance.

¹H-NMR (CD₃OD, δ ppm): 1.17–2.30 (10H, m), 3.14–3.40 (3H, m), 4.12–4.26 (2H, m), 7.22–7.40 (3H, m), 7.55–7.66 (2H, m), 7.75–7.86 (1H, m)

ESI-MS (m/e, as $(C_{18}H_{24}F_2N_2O_3+H)^+$): 355

EXAMPLE 84

(1-(Iminomethyl)piperidin-4-yl)methyl(2R)-2-((1R)-3,3-difluoro-4-hydroxycyclopentyl)-2-hydroxy-2-phenylethanoate monohydrochloride Using piperidin-4-ylmethyl(2R)-2-((1R)-3,3-difluoro-4-hydroxycyclopentyl)-2-hydroxy-2-phenylethanoate, the title compound was prepared through the treatments as in the method of Example 48. The product was obtained as a colorless oily substance ¹H-NMR (CD₃OD, δ ppm): 1.10–1.42 (3H, m), 1.68–1.92 (4H, m), 1.92–2.10 (2H, m), 2.99–3.13 (2H, m), 3.22–3.48 (1H, m), 3.70–3.82 (1H, m), 3.89–4.22 (4H, m), 7.25–7.41 (3H, m), 7.56–7.65 (2H, m), 7.75–7.91 (1H, m)

ESI-MS (m/e, as $(C_{20}H_{26}F_2N_2O_4+H)^+$): 397

EXAMPLE 85

(1-Amidinopiperidin-4-yl)methyl(2R)-2-((1R)-3,3-difluorocyclopentyl)-2-hydroxy-2-phenylethanoate monohydrochloride To a solution of 14 mg of piperidin-4-ylmethyl(2R)-2-((1R)-3,3-difluorocyclopentyl)-2-hydroxy-2-phenylethanoate in 0.020 ml of anhydrous dimethylformamide, 6.3 mg of 1H-pyrazole-1-carboxamidine hydrochloride and 0.008 ml of diisopropylethylamine were added, followed by stirring at room temperature for 12 hours. The reaction liquid was condensed and dried to solid. Thus obtained crude product was purified on silica gel column chromatography (eluent: chloroform/methanol=10/1), to provide 11 mg of the title compound in the form of a colorless solid.

¹H-NMR (CD₃OD, δ ppm): 1.08–2.22 (1H, m), 3.01 (2H, t, J=13.57 Hz), 3.24 (1H, m), 3.82 (2H, m), 4.02 (1H, dd, J=6.12, 10.95 Hz), 4.10 (1H, dd, J=6.12, 10.95 Hz), 7.31 (3H, m), 7.60 (2H, d, J=7.10 Hz)

ESI-MS (m/e, as $(C_{20}H_{27}F_2N_3O_3+H)^+$): 396

EXAMPLE 86

1-Amidinopiperidin-4-yl(2R)-2-((1R)-3,3-difluorocyclopentyl)-2-hydroxy-2-phenylethanoate hydrochloride Using piperidin-4-yl(2R)-2-((1R)-3,3-difluorocyclopentyl)-2-hydroxy-2-phenylethanoate, the title compound was prepared through the treatments as in the method of Example 85. The product was obtained as a colorless solid.

¹H-NMR (CD₃OD, δ ppm): 1.61–1.82 (3H, m), 1.82–2.23 (7H, m), 3.22–3.52 (6H, m), 5.08 (1H, m), 7.35 (3H, m), 7.63 (2H, dd, J=1.56, 7.05 Hz)

ESI-MS (m/e, as $(C_{19}H_{25}F_2N_3O_3+H)^+$): 382

EXAMPLE 87

1,4,5,6-Tetrahydropyrimidin-5-yl(2R)-2-((1R)-3,3-difluorocyclopentyl)-2-hydroxy-2-phenylethanoate monohydrochloride To a solution of 18.6 mg of 2-thioxohexahydropyrimidin-5-yl(2R)-2-((1R)-3,3-difluorocyclopentyl)-2-hydroxy-2-phenylethanoate in 1 ml of ethanol, Raney-nickel was added, followed by 6 hours' stirring at ambient temperature and pressure in hydrogen atmosphere. The reaction liquid was filtered with Celite. After adding 10% hydrochloric acid-methanol to the filtrate, the solvent was distilled off under reduced pressure to provide 15.4 mg of the title compound in the form of a white solid.

¹H-NMR (CD₃OD, δ ppm): 1.55–2.20 (9H, m), 2.69 (1H, s), 3.20–3.40 (2H, m), 3.80 (1H, s), 4.23 (1H, dd, J=4.29, 11.8 Hz), 4.39 (1H, dd, J=4.29, 11.8 Hz), 7.36 (3H, m), 7.59 (2H, d, J=7.10 Hz), 7.97 (1H, s)

ESI-MS (m/e, as $(C_{18}H_{22}F_2N_2O_3+H)^+$): 353

EXAMPLE 88

(4S)-1,4,5,6-tetrahydropyrimidin-4-ylmetyl(2R)-2-((1R)-3,3-difluorocyclopentyl)-2-hydroxy-2-phenylethanoate monohydrochloride Using ((4S)-2-thioxohexahydropyrimidin-4-yl)methyl (2R)-2-((1R)-3,3-difluorocyclopentyl)-2-hydroxy-2-phenylethanoate, the title compound was prepared through the treatments as in the method of Example 87. The product was obtained as a colorless oily substance.

¹H-NMR (CD₃OD, δ ppm): 1.50–2.22 (9H, m), 3.20–3.40 (2H, m), 4.11–4.47 (2H, m), 7.33 (3H, m), 7.61 (2H, d, J=7.1 Hz), 7.98 (1H, s)

ESI-MS (m/e, as $(C_{18}H_{22}F_2N_2O_3+H)^+$): 353

EXAMPLE 89

(4R)-1,4,5,6-tetrahydropyrimidin-4-ylmethyl(2R)-2-((1R)-3,3-difluorocyclopentyl)-2-hydroxy-2-phenylethanoate monohydrochloride Using ((4R)-2-thioxohexahydropyrimidin-4-yl)methyl (2R)-2-((1R)-3,3-difluorocyclopentyl)-2-hydroxy-2-phenylethanoate, the title compound was prepared through the treatments as in the method of Example 87. The product was obtained as a colorless solid.

¹H-NMR (CD₃OD, δ ppm): 1.54–2.26 (6H, m), 3.05–3.75 (5H, m), 5.39–5.48 (1H, m), 7.20–7.47 (3H, m), 7.53–7.69 (2H, m), 7.93–8.18 (1H, m)

ESI-MS (m/e, as $(C_{17}H_{20}F_2N_2O_3+H)^+$): 339

Referential Example 1

(2R)-2-((1R)-3,3-difluorocyclopentyl)-2-hydroxy-2-phenylacetic acid (Step 1)

Synthesis of (2R,5R)-2-(t-butyl)-5-((1R)-3-oxocyclopentyl)-5-phenyl-1,3-dioxolan-4-one and (2R,5R)-2-(t-butyl)-5-((1S)-3-oxocyclopentyl)-5-phenyl-1,3-dioxolan-4-one Following the method of D. Seebach, et al. [Tetrahedron, Vol. 40, pp. 1313–1324 (1984)], (2R,5R)-2-(t-butyl)-5-phenyl-1,3-dioxolan-4-one was synthesized. To a liquid mixture of 20 ml of a tetrahydrofuran solution containing 510 mg of the synthesized compound with 1 ml of hexamethyl-phosphoric triamide, 1.7 ml of 1.5M hexane solution of lithium diisopropylamide was added dropwise at −78° C., stirred for 30 minutes, then 1.5 ml of tetrahydrofuran solution containing 285 mg of cyclopentenone was added, and the system was further stirred for 1.5 hours. The reaction liquid was diluted with ethyl acetate, washed successively with a saturated aqueous ammonium chloride solution, water and saturated brine, and thereafter dried over anhydrous magnesium sulfate. The solvent was distilled off under reduced pressure, and the resultant residue was purified on medium pressure silica gel column chromatography (eluent: hexane/ethyl acetate=15/1–10/1), to provide 150 mg and 254 mg of the title compounds, respectively, as oily substances. Configuration of each of said compounds was determined from NOE of NMR.

(Step 2)

Synthesis of (2R,5R)-2-(t-butyl)-5-((1R)-3,3-difluorocyclopentyl)-5-phenyl-1,3-dioxolan-4-one To a solution of 2.8 g of (2R,5R)-2-(t-butyl)-5-((1R)-3-oxocyclopentyl)-5-phenyl-1,3-dioxolan-4-one in 30 ml of chloroform, 4.89 ml of trifluorodiethylaminosulfuric acid was added under cooling with ice, followed by 20 hours' stirring at room temperature. The reaction liquid was diluted with chloroform, washed successively with water and with saturated brine, and dried over anhydrous magnesium sulfate. Distilling the solvent off under reduced pressure, the resulting residue was purified on silica gel column chromatography (eluent: hexane/ethyl acetate=20/1) to provide 2.4 g of the title compound.

(Step 3)

Synthesis of (2R)-2-((1R)-3,3-difluorocyclopentyl)-2-hydroxy-2-phenylacetic acid To a solution of 2.4 g of (2R,5R)-2-(t-butyl)-5-((1R)-3,3-difluorocyclopentyl)-5-phenyl-1,3-dioxolan-4-one in 30 ml of methanol, 10 ml of 1N aqueous sodium hydroxide solution was added, followed by 3 hours' stirring at room temperature. Distilling the methanol off under reduced pressure, the reaction liquid was diluted with water and washed with diethyl ether. The aqueous layer was acidified with 1N hydrochloric acid and extracted from diethyl ether, and the organic layer was dried over anhydrous magnesium sulfate. Distilling the solvent off under reduced pressure, 1.66 g of the title compound was obtained.

Referential Example 2

(2R)-2-((1R)-3,3-difluorocyclopentyl)-2-hydroxy-2-(4-chlorophenyl)acetic acid (Step 1)

Synthesis of (2R,5R)-2-(t-butyl)-5-(4-chlorophenyl)-1,3-dioxolan-4-one

To a solution of 16 g of (2R)-2-(4-chlorophenyl)-2-hydroxyacetic acid (cf. JP-Hei 6 (1994)-165695A) in 440 ml of hexane/toluene (10:1), 23 ml of pivalaldehyde and 326 mg of p-toluenesulfonic acid monohydrate were added by the order stated, followed by 12 hours' heating under reflux while removing the generated water with Dean-Stark trap. The reaction liquid was diluted with ethyl acetate, washed with saturated aqueous sodium hydrogencarbonate solution and saturated brine, and dried over anhydrous sodium sulfate. Distilling the solvent off under reduced pressure, 14 g of the title compound was obtained.

(Step 2)

(2R)-2-((1R)-3,3-difluorocyclopentyl)-2-hydroxy-2-(4-chlorophenyl)acetic acid

Using (2R,5R)-2-(t-butyl)-5-(4-chlorophenyl)-1,3-dioxolan-4-one, the title compound was prepared by a method similar to Referential Example 1.

Referential Example 3

(2R)-2-((1R)-3,3-difluorocyclopentyl)-2-hydroxy-2-(4-fluorophenyl)acetic acid

Using (2R)-2-(4-fluorophenyl)-2-hydroxyacetic acid (cf. JP-Hei 6 (1994)-165695A), the title compound was prepared by a method similar to Referential Example 2.

Referential Example 4

(2R)-2-((1R)-3,3-difluorocyclopentyl)-2-hydroxy-2-(4-bromophenyl)acetic acid

Using (2R)-2-(bromophenyl)-2-hydroxyacetic acid (cf. JP-Hei 6-165695A), the title compound was prepared by a method similar to Referential Example 2.

Referential Example 5

(2R)-2-((1R)-3,3-difluorocyclopentyl)-2-hydroxy-2-(4-methoxyphenyl)acetic acid (Step 1)

Synthesis of (2R)-2-methoxyphenyl-2-hydroxyacetic acid

To a solution of 19 g of methyl(2R)-2-(methoxyphenyl)-2-hydroxyethanoate (cf. Journal of Chemical Society, Parkintrans 1, 2253–2255 (1992)) in 50 ml of methanol, 50 ml of 3N aqueous sodium hydroxide solution was added, followed by 12 hours' stirring at room temperature. Distilling the methanol off under reduced pressure, the reaction liquid was acidified with 1N hydrochloric acid and extracted with chloroform. The organic layer was dried over anhydrous sodium sulfate and the solvent was distilled off under reduced pressure, to provide 11 g of the title compound.

(Step 2)

Synthesis of (2R)-2-((1R)-3,3-difluorocyclopentyl)-2-hydroxy-2-(4-methoxyphenyl)acetic acid Using (2R)-2-(methoxyphenyl)-2-hydroxyacetic acid, the title compound was prepared by a method similar to Referential Example 2.

Referential Example 6

(2R)-2-((1R)-3,3-difluorocyclopentyl)-2-hydroxy-2-(2-chlorophenyl)acetic acid

Using (2R)-2-((1R)-3,3-difluorocyclopentyl)-2-hydroxy-2-(2-chlorophenyl)acetic acid (cf. JP-Hei 6–165695A), the title compound was prepared by a method similar to Referential Example 2.

Referential Example 7

(2R)-2-((1R)-3,3-difluorocyclopentyl)-2-hydroxy-2-(2,4-difluorophenyl)acetic acid (Step 1)

Synthesis of methyl(2R)-2-(2,4-difluorophenyl)-2-hydroxyethanoate

T. Miyazawa, et al.'s method [Journal of Chemical Society, Parkin trans 1, 2253–2255 (1992)] was used. To a solution of 3.9 g of 2-(2,4-difluorophenyl)-2-hydroxyacetec acid in 20 ml of diisopropyl ether, 20 ml of vinyl acetate and 2 g of Lipase AK were added, followed by 13 days' stirring at room temperature. The precipitate was removed by filtration with Celite, and the solvent was distilled off from the filtrate under reduced pressure. The residue was purified on silica gel column chromatography (eluent: hexane-hexane/ethyl acetate=2/1) to provide 2.4 g of the title compound.

(Step 2)

Synthesis of (2R)-2-((1R)-3,3-difluorocyclopentyl)-2-hydroxy-2-(2,4-difluorophenyl)acetic acid Using (2R)-2-(2,4-difluorophenyl)-2-hydroxyacetic acid, the title compound was prepared by a method similar to Referential Example 5.

Referential Example 8

(2R)-2-((1R)-3,3-difluorocyclopentyl)-2-hydroxy-2-(1,3-benzodioxol-5-yl)acetic acid Using (2R)-2-(1,3-benzodioxol-5-yl)-2-hydroxyacetic acid (cf. JP-Hei 6–165695A), the title compound was prepared by a method similar to Referential Example 2.

Referential Example 9

(2R)-2-((1R)-3-fluorocyclopentyl)-2-hydroxy-2-phenylacetic acid (Step 1)

Synthesis of (2R,5R)-2-(t-butyl)-5-((1R)-3-hydroxycyclopentyl)-5-phenyl-1,3-dioxolan-4-one To a solution of 169 mg of the (2R,5R)-2-(t-butyl)-5-((1R)-3-oxocyclopentyl)-5-phenyl-1,3-dioxolan-4-one, as obtained in Step 1 of Referential Example 1, in 2 ml of methanol, 71 mg of sodium borohydride was added under cooling with ice, followed by 30 minutes' stirring at the same temperature. The reaction liquid was diluted with diethyl ether, washed with water and with saturated brine, and dried over anhydrous magnesium sulfate. Distilling the solvent off under reduced pressure, 157 mg of the title compound was obtained as a colorless oily substance.

(Step 2)

Synthesis of (2R)-2-((1R)-3-fluorocyclopentyl)-2-hydroxy-2-phenylacetic acid

Using (2R,5R)-2-(t-butyl)-5-((1R)-3-hydroxycyclopentyl)-5-phenyl-1,3-dioxolan-4-one, the title compound was prepared by a method similar to Steps 2 and 3 of Referential Example 1.

Referential Example 10

(2R)-2-((1S)-3-fluorocyclopentyl)-2-hydroxy-2-(4-chlorophenyl)-acetic acid

Using the (2R,5R)-2-(t-butyl)-5-((1S)-3-oxocyclopentyl)-5-(4-chlorophenyl)-1,3-dioxolan-4-one as obtained in Referential Example 2, the title compound was prepared by a method similar to Referential Example 9.

Referential Example 11

(2R)-2-((1R,4R)-3,3-difluoro-4-hydroxycyclopentyl)-2-hydroxy-2-phenylacetic acid (Step 1)

Synthesis of (4R)-4-((2R,4R)-2-(t-butyl)-5-oxo-4-phenyl-1,3-dioxolan-4-yl)-1-cyclopentenyl acetate and (3R)-3-((2R,4R)-2-(t-butyl)-5-oxo-4-phenyl-1,3-dioxolan-4-yl)-1-cyclopentenyl Acetate To a solution of 185 mg of (2R,5R)-2-(t-butyl)-5-((1R)-3-oxocyclopentyl)-5-phenyl-1,3-dioxolan-4-one in 1 ml of vinyl acetate, 10 mg of p-toluenesulfonic acid monohydrate was added, followed by 12 hours' heating under reflux. Distilling the solvent off under reduced pressure, the residue obtained was purified on silica gel column chromatography (eluent: hexane–hexane/ethyl acetate=15/1) to provide 184 mg of the title compounds as a mixture of the two compounds.

(Step 2)

Synthesis of (2R,5R)-2-(t-butyl)-5-((1R,3R)-3-hydroxy-4-oxocyclopentyl)-5-phenyl-1,3-dioxolan-4-one To a solution of 169 mg of (4R)-4-((2R,4R)-2-(t-butyl)-5-oxo-4-phenyl-1,3-dioxolan-4-yl)-1-cyclopentenyl acetate in 7.5 ml of acetonitrile and water (2:1), 80 mg of N-methyl morpholine-oxide and 0.2 ml of 2% aqueous osmium tetraoxide solution were successively added at 0° C. by the order stated, followed by 3 hours' stirring at the same temperature. Sodium sulfite was added to the reaction liquid and stirred for further 30 minutes. The reaction liquid was then diluted with ethyl acetate, washed successively with water and saturated brine, and dried over anhydrous sodium sulfate. Distilling the solvent off under reduced pressure, the residue obtained was purified on silica gel column chromatography (eluent: hexane–hexane/ethyl acetate=2/1) to provide 32 mg of the title compound as a colorless solid.

(Step 3)

Synthesis of (1R,4R)-4-((2R,4R)-2-(t-butyl)-5-oxo-4-phenyl-1,3-dioxolan-4-yl)-2-oxocyclopentyl acetate To a solution of 32 mg of (2R,5R)-2-(t-butyl)-5-((1R,3R)-3-hydroxy-4-oxocyclopentyl)-5-phenyl-1,3-dioxolan-4-one in 1 ml of pyridine, 0.5 ml of acetic anhydride was added, followed by 1 hour's stirring at room temperature. The reaction liquid was diluted with ethyl acetate, washed successively with water, 1N hydrochloric acid and saturated brine, and dried over anhydrous sodium sulfate. Distilling the solvent off under reduced pressure, the residue obtained was purified on preparative thin layer chromatography (Kieselgel™ 60F$_{254}$, Art 5744 (Merck), chloroform/acetone=20/1) to provide 27 mg of the title compound as a colorless oily substance.

(Step 4)

Synthesis of (2R)-2-((1R,4R)-3,3-difluoro-4-hydroxycyclopentyl)-2-hydroxy-2-phenylacetic acid Using the (1R,4R)-4-((2R,4R)-2-(t-butyl)-5-oxo-4-phenyl-1,3-dioxolan-4-yl)-2-oxocyclopentyl acetate as obtained in Step 3, the title compound was prepared by treating it by a method similar to Steps 2 and 3 of Example 1.

Referential Example 12

Piperidin-4-yl(2R)-((1R)-3,3-difluorocyclopentyl)-2-hydroxy-2-phenylethanoate (Step 1)

Synthesis of 4-hydroxy-1-t-butoxycarbonylpiperidine

To a solution of 10 g of 4-hydroxypiperidine in 300 ml of chloroform, 20 g of di-t-butylcarbonate was added under cooling with ice, followed by 2 hours' stirring at room temperature. The reaction liquid was diluted with ethyl acetate, washed successively with water and saturated brine, and dried over anhydrous sodium sulfate. Distilling the solvent off under reduced pressure, 18 g of the title compound was obtained.

(Step 2)

Synthesis of t-butyl 4-((2R)-2-((1R)-3,3-difluorocyclopentyl)-2-hydroxy-2-phenylethanoyloxy)tetrahydropyridine-1(2H)-carboxylate To a solution of 128 mg of (2R)-2-((1R)-3,3-difluorocyclopentyl)-2-hydroxy-2-phenylacetic acid in 3 ml of dimethylformamide, 81 mg of carbonyldiimidazole was added and stirred for 30 minutes. Then 121 mg of 4-hydroxy-1-t-butoxycarbonylpiperidine and 10 mg of sodium hydride were added successively, followed by another 30 minutes' stirring. The reaction liquid was diluted with ethyl acetate, washed successively with water and saturated brine, and dried over anhydrous sodium sulfate. Distilling the solvent off under reduced pressure, the residue obtained was purified on silica gel column chromatography (eluent: hexane/ethyl acetate=3/1) to provide 121 mg of the title compound.

(Step 3)

Synthesis of piperidin-4-yl(2R)-((1R)-3,3-difluorocyclopentyl)-2-hydroxy-2-phenylethanoate 162 Milligrams of t-butyl 4-((2R)-2-((1R)-3,3-difluorocyclopentyl)-2-hydroxy-2-phenylethanoyloxy)tetrahydropyridine-1(2H)-carboxylate was dissolved in 5 ml of 10% hydrochloric acid-methanol, stirred for 12 hours, and the solvent was distilled off under reduced pressure. The residue was diluted with water, washed with diethyl ether and a saturated aqueous sodium hydrogencarbonate solution was added to the aqueous layer to render it alkaline. Following an extraction with ethyl acetate, the organic layer was washed with saturated brine and dried over anhydrous sodium sulfate. Distilling the solvent off under reduced pressure, 104 mg of the title compound was obtained as a colorless, foamy substance.

Referential Example 13

Piperidin-4-ylmethyl(2R)-((1R)-3,3-difluorocyclopentyl)-2-hydroxy-2-phenylethanoate (Step 1)

Synthesis of ethyl N-t-butoxycarbonyl-isonipecotate

Using ethyl isonipecotate, the title compound was prepared by a method similar to Step 1 of Referential Example 12.

(Step 2)

Synthesis of N-t-butoxycarbonyl-4-piperidinemethanol

To a solution of 516 mg of ethyl N-t-butoxycarbonyl-isonipecotate in 30 ml of tetrahydrofuran, 200 mg of lithium-aluminum hydride was added under cooling with ice, followed by 20 minutes' stirring at the same temperature. Sodium sulfate decahydrate was added to the reaction liquid, stirred for 30 minutes and filtered with Celite. Distilling the solvent off under reduced pressure, 414 mg of the title compound was obtained.

(Step 3)

Synthesis of piperidin-4-ylmethyl(2R)-((1R)-3,3-difluorocyclopentyl)-2-hydroxy-2-phenylethanoate Using N-t-butoxycarbonyl-4-piperidinemethanol, the title compound was prepared by a method similar to Steps 2 and 3 of Referential Example 12.

Referential Example 14

2-(Piperidin-4-yl)ethyl(2R)-((1R)-3,3-difluorocyclopentyl)-2-hydroxy-2-phenylethanoate (Step 1)

Synthesis of t-butyl 4-(2-ethoxy-2-oxoethylidene)tetrahydropyridine-1(2H)-carboxylate To a solution of 9.1 g of 60% oily sodium hydride in 200 ml of tetrahydrofuran, 38.0 ml of ethyl diethylphosphonoacetate was added dropwise under cooling with ice, stirred for 20 minutes, and thereafter a solution of 31.4 g of 1-t-butoxycarbonyl-4-piperidone in 500 ml of tetrahydrofuran was added dropwise, followed by 40 minutes' stirring at the same temperature. The reaction liquid was diluted with ethyl acetate, washed successively with aqueous ammonium chloride solution, water and saturated brine, and dried over anhydrous sodium sulfate. Distilling the solvent off under reduced pressure, the residue was recrystallized from methanol to provide 33.5 g of the title compound.

(Step 2)

Synthesis of t-butyl 4-(2-ethoxy-2-oxoethyl)tetrahydropyridine-1(2H)-carboxylate To a solution of 355 mg of t-butyl 4-(2-ethoxy-2-oxoethylidene)tetrahydropyridine-1(2H)-carboxylate in 10 ml of methanol, 50 mg of 10% palladium-on-carbon catalyst was added and stirred for 13 hours in 3 atmospheres' hydrogen pressure. Filtering the catalyst off, the solvent was distilled off under reduced pressure to provide 334 mg of the title compound.

(Step 3)

Synthesis of t-butyl 4-(2-hydroxyethyl)tetrahydropyridine-1(2H)-carboxylate

To a solution of 263 mg of t-butyl 4-(2-ethoxy-2-oxoethyl)-tetrahydropyridine-1(2H)-carboxylate in 15 ml of tetrahydrofuran, 100 mg of lithiumaluminum hydride was added under cooling with ice, followed by 20 minutes' stirring at the same temperature. To the reaction liquid sodium sulfate decahydrate was added, stirred for 30 minutes and filtered with Celite. Distilling the solvent off under reduced pressure, 207 mg of the title compound was obtained.

(Step 4)

Synthesis of 2-(piperidin-4-yl)ethyl(2R)-((1R)-3,3-difluorocyclopentyl)-2-hydroxy-2-phenylethanoate Using t-butyl 4-(2-hydroxyethyl)tetrahydropyridine-1 (2H)-carboxylate, the title compound was prepared by a method similar to Steps 2 and 3 of Referential Example 12.

Referential Example 15

3-(Piperidin-4-yl)propyl(2R)-2-((1R)-3,3-difluorocyclopentyl)-2-hydroxy-2-phenylethanoate
(Step 1)
Synthesis of t-butyl 4-(3-ethoxy-3-oxopropyl)tetrahydropyridine-1(2H)-carboxylate To a solution of 1.0 g of t-butyl 4-(3-ethoxy-3-oxoprop-1-enyl)-tetrahydropyridine-1(2H)-carboxylate (cf. WO9501336) in 20 ml of ethanol, 300 mg of 10% palladium-on-carbon catalyst, and stirred for 3 hours in a hydrogen atmosphere, at ambient temperature and pressure. After filtering the catalyst off, the solvent was distilled off under reduced pressure to provide 700 mg of the title compound.
(Step 2)
Synthesis of t-butyl 4-(3-hydroxypropyl)tetrahydropyridine-1(2H)-carboxylate Using t-butyl 4-(3-ethoxy-3-oxopropyl)tetrahydropyridine-1(2H)-carboxylate, the title compound was prepared by a method similar to Step 3 of Referential Example 14.
(Step 3)

Using t-butyl 4-(3-hydroxypropyl)tetrahydropyridine-1(2H)-carboxylate, the title compound was prepared by a method similar to Steps 2 and 3 of Referential Example 12.

Referential Example 16

1,2,3,6-Tetrahydropiridin-4-ylmethyl(2R)-2-((1R)-3,3-difluorocyclopentyl)-2-hydroxy-2-phenylethanoate Using t-butyl 4-(hydroxymethyl)-3,6-dihydropyridine-1(2H)-carboxylate (cf. WO9806720), the title compound was prepared by a method similar to Steps 2 and 3 of Referential Example 12.

Referential Example 17

2-(4-Piperidinylidene)ethyl(2R)-2-((1R)-3,3-difluorocyclopentyl)-2-hydroxy-2-phenylethanoate Using t-butyl 4-(2-hydroxyethylidene)tetrahydropyridine-1(2H)-carboxylate (cf. WO9940070), the title compound was prepared by a method similar to Steps 2 and 3 of Referential Example 12.

Referential Example 18

2-(1,2,3,6-Tetrahydropyridin-4-yl)ethyl(2R)-2-((1R)-3,3-difluorocyclopentyl)-2-hydroxy-2-phenylethanoate Using t-butyl 4-(2-hydroxyethyl)-3,6-dihydropyridine-1(2H)-carboxylate (cf. WO9806720), the title compound was prepared by a method similar to Steps 2 and 3 of Referential Example 12.

Referential Example 19

(3R)-piperidin-3-ylmethyl(2R)-2-((1R)-3,3-difluorocyclopentyl)-2-hydroxy-2-phenylethanoate Using t-butyl(3R)-3-(hydroxymethyl)tetrahydropyridine-1(2H)-carboxylate (cf. *Tetrahedron Asymmetry*, Vol.3, p.1049 (1992)), the title compound was prepared by a method similar to Steps 2 and 3 of Referential Example 12.

Referential Example 20

2-((3R)-piperidin-3-yl)ethyl(2R)-2-((1R)-3,3-difluorocyclopentyl)-2-hydroxy-2-phenylethanoate
(Step 1)
Synthesis of t-butyl(3R)-3-(2-ethoxy-2-oxoethyl)tetrahydropyridine-1(2H)-carboxylate To a solution of 1.15 g of ethyl 2-((3R)-piperidin-3-yl)acetate L-(+)-mandelate (cf. JP-Hei 10 (1998)-508321A) in 20 ml of dioxane, 780 mg of di-t-butyl-dicarbonate and 10 ml of 10% aqueous potassium carbonate solution were added, followed by 30 minutes' stirring at room tempereture. The reaction liquid was diluted with diethyl ether, washed with saturated brine and dried over anhydrous magnesium sulfate. Distilling the solvent off under reduced pressure, 985 mg of the title compound was obtained.
(Step 2)
Synthesis of t-butyl(3R)-3-(2-hydroxyethyl)tetrahydropyridine-1(2H)-carboxylate To a solution of 143 mg of t-butyl(3R)-3-(2-ethoxy-2-oxoethyl)tetrahydropyridine-1(2H)-carboxylate in 5 ml of tetrahydrofuran, 30 mg of litiumaluminum hydride was added under cooling with ice, followed by 20 minutes' stirring at the same temperature. To the reaction liquid sodium sulfate decahydrate was added, stirred for 12 hours and filtered with Celite. Distilling the solvent off under reduced pressure, 118 mg of the title compound was obtained.
(Step 3)
Synthesis of 2-((3R)-piperidin-3-yl)ethyl(2R)-2-((1R)-3,3-difluorocyclopentyl)-2-hydroxy-2-phenylethanoate Using t-butyl(3R)-3-(2-hydroxyethyl)tetrahydropyridine-1(2H)-carboxylate, the title compound was prepared by a method similar to Steps 2 and 3 of Referential Example 12.

Referential Example 21

2-((3S)-piperidin-3-yl)ethyl(2R)-2-((1R)-3,3-difluorocyclopentyl)-2-hydroxy-2-phenylethanoate Using ethyl 2-((3S)-piperidin-3-yl)acetate D-(−)-mandelate (cf. JP-Hei 10 (1998)-508321A), the title compound was prepared by a method similar to Referential Example 20.

Referential Example 22

(3R)-pyrrolidin-3-yl(2R)-2-((1R)-3,3-difluorocyclopentyl)-2-hydroxy-2-phenylethanoate Using t-butyl(3R)-3-hydroxypyrrolidine-1-carboxylate (cf. *Syn. Commun.*, Vol.15, p.587 (1985)), the title compound was prepared by a method similar to Steps 2 and 3 of Referential Example 12.

Referential Example 23

(3S)-pyrrolidin-3-yl(2R)-2-((1R)-3,3-difluorocyclopentyl)-2-hydroxy-2-phenylethanoate Using t-butyl(3S)-3-hydroxypyrrolidine-1-carboxylate (cf. *Syn. Commun.*, Vol.15, p.587 (1985)), the title compound was prepared by a method similar to Steps 2 and 3 of Referential Example 12.

Referential Example 24

(3R)-pyrrolidin-3-ylmethyl(2R)-2-((1R)-3,3-difluorocyclopentyl)-2-hydroxy-2-phenylethanoate Using t-butyl(3R)-3-(hydroxymethyl)pyrrolidine-1-carboxylate (cf. JP96-107364), the title compound was prepared by a method similar to Steps 2 and 3 of Referential Example 12.

Referential Example 25

(3S)-pyrrolidin-3-ylmethyl(2R)-2-((1R)-3,3-difluorocyclopentyl)-2-hydroxy-2-phenylethanoate Using t-butyl(3S)-3-(hydroxymethyl)pyrrolidine-1-carboxylate (cf. JP96-107364), the title compound was prepared by a method similar to Steps 2 and 3 of Referential Example 12.

Referential Example 26

2-((3S)-pyrrolidin-3-yl)ethyl(2R)-2-((1R)-3,3-difluorocyclopentyl)-2-hydroxy-2-phenylethanoate (Step 1)

Synthesis of methyl 2-(3S)-5-oxo-1-((1R)-1-phenylethyl)pyrrolidin-3-yl acetate

To a solution of 100 mg of (4R)-4-(hydroxymethyl)-1-((1R)-1-phenylethyl)pyrrolidin-2-one (cf. *Heterocycles*, Vol.51, 2463–2470 (1999)) in 2 ml of chloroform, 0.075 ml of triethylamine and 0.041 ml of methanesulfonyl chloride were added, followed by 2 hours' stirring at room temperature. The reaction liquid was diluted with chloroform, washed successively with saturated aqueous sodium hydrogencarbonate solution and saturated brine, and dried over anhydrous sodium sulfate. Distilling the solvent off under reduced pressure, 49 mg of sodium cyanide was added to the residue as dissolved in 2 ml of dimethyl sulfoxide, and stirred for 3 hours at 80° C. The reaction liquid was diluted with chloroform, washed with saturated brine, and dried over anhydrous sodium sulfate. The solvent was distilled off under reduced pressure, and the residue was dissolved in 2 ml of conc. hydrochloric acid, heated under reflux for 20 hours, and water was removed under reduced pressure. Adding 5 ml of 10% hydrochloric acid-methanol to the residue, heating under reflux was continued for further 12 hours, and the solvent was distilled off under reduced pressure. The residue was rendered alkaline by addition of aqueous sodium hydrogencarbonate solution, and then extracted with chloroform. The organic layer was dried over anhydrous sodium sulfate. Distilling the solvent off under reduced pressure, 90 mg of the title compound was obtained.

(Step 2)

Synthesis of 2-((3S)-1-((1R)-1-phenylethyl)pyrrolidin-3-yl)ethyl acetate

To a solution of 90 mg of methyl 2-(3S)-5-oxo-1-((1R)-1-phenylethyl)pyrrolidin-3-ylacetate in 2 ml of tetrahydrofuran, 25 mg of lithiumaluminum hydride was added under cooling with ice, followed by 2 hours' heating under reflux. To the reaction liquid sodium sulfate decahydrate was added, stirred for 45 minutes, filtered with Celite and the solvent was distilled off under reduced pressure. To 1 ml of chloroform solution of the resulting residue, 0.060 ml of triethylamine and 0.040 ml of acetic anhydride were added, followed by 5 hours' standing at room temperature. The reaction liquid was diluted with ethyl acetate, washed successively with saturated aqueous sodium hydrogencarbonate solution and saturated brine, and dried over anhydrous sodium sulfate. Distilling the solvent off under reduced pressure, the residue was purified on silica gel column chromatography (eluent: chloroform/methanol=10/1) to provide 64 mg of the title compound.

(Step 3)

Synthesis of t-butyl(3S)-3-(2-(acetyloxy)ethyl)pyrrolidine-1-carboxylate

To a solution of 64 mg of 2-((3S)-1-((1R)-1-phenylethyl)-pyrrolidin-3-yl)ethyl acetate in 5 ml of methanol, 64 mg of palladium hydroxide-carbon was added, and stirred for 21 hours at ambient temperature under 3 atmospheres of hydrogen pressure. The reaction liquid was filtered with Celite, the solvent was distilled off under reduced pressure, and the residue was dissolved in 1 ml of chloroform. To the solution 78 mg of di-t-butyl-dicarbonate and 0.035 ml of triethylamine were added and stirred for 3 hours at room temperature. The reaction liquid was diluted with chloroform, washed successively with water and saturated brine, and dried over anhydrous sodium sulfate. Distilling the solvent off under reduced pressure, the resulting residue was purified on silica gel column chromatography (eluent: ethyl acetate/hexane=2/1) to provide 34 mg of the title compound.

(Step 4)

Synthesis of t-butyl(3S)-3-(2-hydroxyethyl)pyrrolidine-1-carboxylate

To a solution of 34 mg of t-butyl(3S)-3-(2-acetyloxyethyl)pyrrolidine-1-carboxylate in 1 ml of methanol, 54 mg of potassium carbonate was added, and stirred for 2.5 hours at room temperature. The reaction liquid was diluted with chloroform, washed successively with water and saturated brine and dried over anhydrous sodium sulfate. Distilling the solvent off under reduced pressure, 29 mg of the title compound was obtained.

(Step 5)

Synthesis of 2-((3S)-pyrrolidin-3-yl)ethyl(2R)-2-((1R)-3,3-difluorocyclopentyl)-2-hydroxy-2-phenylethanoate Using t-butyl(3S)-3-(2-hydroxyethyl)pyrrolidine-1-carboxylate, the title compound was prepared by a method similar to Steps 2 and 3 of Referential Example 12.

Referential Example 27

2-((3R)-pyrrolidin-3-yl)ethyl(2R)-2-((1R)-3,3-difluorocyclopentyl)-2-hydroxy-2-phenylethanoate Using (4S)-4-(hydroxymethyl)-1-((1R)-1-phenylethyl)pyrrolidin-2-one, the title compound was prepared by a method similar to Referential Example 26.

Referential Example 28

(2R)-pyrrolidin-2-ylmethyl(2R)-2-((1R)-3,3-difluorocyclopentyl)-2-hydroxy-2-phenylethanoate Using t-butyl(2R)-2-(hydroxymethyl)pyrrolidine-1-carboxylate, the title compound was prepared by a method similar to Steps 2 and 3 of Referential Example 12.

Referential Example 29

Azetidin-3-yl(2R)-2-((1R)-3,3-difluorocyclopentyl)-2-hydroxy-2-phenylethanoate

Using t-butyl 3-hydroxyazetidine-1-carboxylate (cf. WO9742189), the title compound was prepared by a method similar to Steps 2 and 3 of Referential Example 12.

Referential Example 30

Azetidin-3-ylmethyl(2R)-2-((1R)-3,3-difluorocyclopentyl)-2-hydroxy-2-phenylethanoate Using t-butyl 3-(hydroxymethyl)azetidine-1-carboxylate (*Eur. J. Med. Chem.*, Vol.34, 363–380 (1999)), the title compound was prepared by a method similar to Steps 2 and 3 of Referential Example 12.

Referential Example 31

2-(Azetidin-3-yl)ethyl(2R)-2-((1R)-3,3-difluorocyclopentyl)-2-hydroxy-2-phenylethanoate Using t-butyl 3-(2-hydroxyethyl)azetidine-1-carboxylate (cf. WO9412181), the title compound was prepared by a method similar to Steps 2 and 3 of Referential Example 12.

Referential Example 32

3-Endo-8-azabicyclo[3.2.1]oct-3-yl(2R)-2-((1R)-3,3-difluorocyclopentyl)-2-hydroxy-2-phenylethanoate Using t-butyl 3-endo-3-hydroxy-8-azabicyclo[3.2.1]octane-8-carboxylate (cf. *Drug Metab. Dispos.*, Vol.20, 596–602 (1992)), the title compound was prepared by a method similar to Steps 2 and 3 of Referential Example 12.

Referential Example 33

3-Azabicyclo[3.3.1]non-9-yl(2R)-2-((1R)-3,3-difluorocyclopentyl)-2-hydroxy-2-phenylethanoate Using t-butyl 9-hydroxy-3-azabicyclo[3.3.1]nonane-3-carboxylate, the title compound was prepared by a method similar to Steps 2 and 3 of Referential Example 12.

Referential Example 34

3-Exo-8-azabicyclo[3.2.1]oct-3-ylmethyl(2R)-2-((1R)-3,3-difluorocyclopentyl)-2-hydroxy-2-phenylethanoate
(Step 1)
Synthesis of 3-exo-8-benzyl-8-azabicyclo[3.2.1]octane-3-carbonitrile To a solution of 332 mg of 8-benzyl-8-azabicyclo[3.2.1]oct-3-one in 9 ml of dimethoxyethane, 550 mg of tosylmethyl isocyanate, 0.25 ml of ethanol and potassium t-butoxide were successively added at 0° C., followed by 5 hours' stirring at 50° C. The reaction liquid was diluted with ethyl acetate, washed with saturated brine and dried over anhydrous sodium sulfate. Distilling the solvent off under reduced pressure, the resulting residue was purified on silica gel column chromatography (eluent: hexane/ethyl acetate= 1/1, to provide 236 mg of the title compound
(Step 2)
Synthesis of methyl 3-exo-8-benzyl-8-azabicyclo[3.2.1]octane-3-carboxylate 236 Milligrams of 8-benzyl-8-azabicyclo[3.2.1]octane-3-carbonitrile was dissolved in 3 ml of conc. hydrochloric acid, and after 12 hours' heating under reflux, water was distilled off under reduced pressure. The resulting residue was dissolved in 10% hydrochloric acid-methanol, and heated under reflux for 2 hours. Distilling the solvent off under reduced pressure, the residue was diluted with ethyl acetate, washed successively with saturated aqueous sodium hydrogencarbonate solution and saturated brine, and dried over anyhydrous sodium sulfate. Distilling the solvent off under reduced pressure, the resulting residue was purified on silica gel column chromatography (eluent: hexane/ethyl acetate=1/1) to provide 225 mg of the title compound.
(Step 3)
Synthesis of (3-exo-8-benzyl-8-azabicyclo[3.2.1]oct-3-yl)methyl(2R)-2-((1R)-3,3-difluorocyclopentyl)-2-hydroxy-2-phenylethanoate Using methyl 3-exo-8-benzyl-8-azabicyclo[3.2.1]octane-3-carboxylate, the title compound was prepared by a method similar to Step 2 of Referential Example 13 and Step 2 of Referential Example 12.
(Step 4)
Synthesis of 3-exo-8-azabicyclo[3.2.1]oct-3-ylmethyl(2R)-2-((1R)-3,3-difluorocyclopentyl)-2-hydroxy-2-phenylethanoate To a solution of 82 mg of (3-exo-8-benzyl-8-azabicyclo-[3.2.1]oct-3-yl)methyl(2R)-2-((1R)-3,3-difluorocyclopentyl)-2-hydroxy-2-phenylethanoate in 5 ml of methanol, 15 mg of palladium hydroxide-carbon catalyst was added, and stirred for 2 hours at ambient temperature and pressure in hydrogen atmosphere. The reaction liquid was filtered with Celite, and the solvent was distilled off under reduced pressure to provide 55 mg of the title compound.

Referential Example 35

(3aR,6aS)-octahydrocyclopenta(c)pyrrol-5-yl(2R)-2-((1R)-3,3-difluorocyclopentyl)-2-hydroxy-2-phenylethanoate Using t-butyl(3aR,6aS)-5-hydroxyhexahydrocyclopenta[c]-pyrrole-2(1H)-carboxylate (cf. WO9806720), the title compound was prepared by a method similar to Steps 2 and 3 of Referential Example 12.

Referential Example 36

2,4-Cis-2-vinylpiperidin-4-yl(2R)-2-((1R)-3,3-difluorocyclopentyl)-2-hydroxy-2-phenylethanoate Using t-butyl 2,4-cis-4-hydroxy-2-vinyltetrahydropyridine-1(2H)-carboxylate, the title compound was prepared by a method similar to Steps 2 and 3 of Referential Example 12.

Referential Example 37

(4-Hydroxypiperidin-4-yl)methyl(2R)-((1R)-3,3-difluorocyclopentyl)-2-hydroxy-2-phenylethanoate
(Step 1)
Synthesis of t-butyl 4-methylenetetrahydropyridine-1 (2H)-carboxylate To a solution of 986 mg of methyltriphenylphosphonium bromide in 20 ml of tetrahydrofuran, 1.87 ml of 1.63 M n-butyl lithium/hexane solution was added dropwise at 0° C., under cooling with ice. The temperature then was immediately raised to room temperature, and the system was stirred for 50 minutes. The reaction liquid was again cooled to 0° C., to which a solution of 500 mg of t-butyl 4-oxotetrahydropyridine-1(2H)-carboxylate in 5 ml of tetrahydrofuran was added dropwise, followed by an hour's stirring at the same temperature. The reaction liquid was diluted with ethyl acetate, washed successively with saturated aqueous ammonium chloride solution and saturated brine, and dried over anhydrous sodium sulfate. Distilling the solvent off under reduced pressure, the resulting residue was purified on silica gel column chromatography (eluent: hexane/ethyl acetate=5/1) to provide 192 mg of the title compound.
(Step 2)
Synthesis of t-butyl 4-hydroxy-4-(hydroxymethyl) tetrahydropyridine-1(2H)-carboxylate To a solution of 98 mg of t-butyl 4-methylenetetrahydropyridine-1(2H)-carboxylate in 2 ml of tetrahydrofuran-water (1:1), 88 mg of N-methyl morpholine-oxide and 0.1 ml of 2% osmium tetraoxide were added at 0° C., followed by 2 hours' stirring at the same temperature. Adding sodium sulfite to the reaction liquid, the reaction liquid was further stirred for 30 minutes, diluted with ethyl acetate, washed successively with water and saturated brine, and dried over anhydrous sodium sulfate. Distilling the solvent off under reduced pressure, 115 mg of the title compound was obtained.
(Step 3)
Synthesis of (4-hydroxypiperidin-4-yl)methyl(2R)-((1R)-3,3-difluorocyclopentyl)-2-hydroxy-2-phenylethanoate Using t-butyl 4-hydroxy-4-(hydroxymethyl) tetrahydropyridine-1(2H)-carboxylate, the title compound was prepared by a method similar to Steps 2 and 3 of Referential Example 12.

Referential Example 38

(1R)-1-piperidin-4-ylethyl(2R)-2-((1R)-3,3-difluorocyclopentyl)-2-hydroxy-2-phenylethanoate
(Step 1)
Synthesis of t-butyl 4-((1S)-1-hydroxyethyl) tetrahydropyridine-1(2H)-carboxylate To a solution of 103 mg of (R)-(+)-α-methyl-4-pyridine-methanol in 6 ml of 2% hydrochloric acid-methanol, 10 mg of platinum oxide was added, followed by 1.5 hours' stirring at room temperature in hydrogen atmosphere of 4 atmospheric pressure. The reaction liquid was filtered with Celite, the solvent was distilled off under reduced pressure, and the resulting residue was dissolved in 6 ml of dioxane. To the solution 78 mg of di-t-butyl-dicarbonate and 4 ml of 1N sodium hydroxide were added, followed by 1 hour's stirring at room temperature. The reaction liquid was diluted with chloroform, washed successively with water and saturated brine, and dried over anhydrous sodium sulfate. Distilling the solvent off under reduced pressure, the resulting residue was purified on silica gel column chromatography (eluent: ethyl acetate/hexane=2/1) to provide 46 mg of the title compound.

(Step 2)

Using t-butyl 4-((1S)-1-hydroxyethyl)tetrahydropyridine-1(2H)-carboxylate, the title compound was prepared by a method similar to Steps 2 and 3 of Referential Example 12.

Referential Example 39

2-Piperadinoethyl(2R)-2-((1R)-3,3-difluorocyclopentyl)-2-hydroxy-2-phenylethanoate Using t-butyl 4-(2-hydroxyethyl)tetrahydropyrazine-1(2H)-carboxylate, the title compound was prepared by a method similar to Steps 2 and 3 of Referential Example 12.

Referential Example 40

2-Aminoethyl(2R)-2-((1R)-3,3-difluorocyclopentyl)-2-hydroxy-2-phenylethanoate

Using t-butyl 2-hydroxyethylcarbamate, the title compound was prepared by a method similar to Steps 2 and 3 of Referential Example 12.

Referential Example 41

3-Aminopropyl(2R)-2-((1R)-3,3-difluorocyclopentyl)-2-hydroxy-2-phenylethanoate

Using t-butyl 3-hydroxypropylcarbamate, the title compound was prepared by a method similar to Steps 2 and 3 of Referential Example 12.

Referential Example 42

3-(Methylamino)propyl(2R)-2-((1R)-difluorocyclopentyl)-2-hydroxy-2-phenylethanoate (Step 1)

Synthesis of 3-(benzylamino)propyl(2R)-2-((1R)-3,3-difluorocyclopentyl)-2-hydroxy-2-phenylethanoate To a methanol solution of 87 mg of 3-aminopropyl(2R)-2-((1R)-3,3-difluorocyclopentyl)-2-hydroxy-2-phenylethanoate, 35 mg of benzaldehyde was added at room temperature, stirred for 30 minutes at the same temperature, sodium borohydride was added, and further stirred for 30 minutes. The reaction liquid was diluted with ethyl acetate, washed successively with saturated aqueous sodium hydrogencarbonate solution and saturated brine, and dried over anhydrous sodium sulfate. Distilling the solvent off under reduced pressure, the resulting residue was purified on silica gel column chromatography (eluent: chloroform/methanol=50/1), to provide the title compound.

(Step 2)

Synthesis of 3-(benzyl(methyl)amino)propyl(2R)-2-((1R)-3,3-difluorocyclopentyl)-2-hydroxy-2-phenylethanoate Using 3-(benzylamino)propyl(2R)-2-((1R)-3,3-difluorocyclopentyl)-2-hydroxy-2-phenylethanoate, the title compound was prepared by a method similar to Step 1 of Example 1.

(Step 3)

Synthesis of 3-(methylamino)propyl(2R)-2-((1R)-3,3-difluorocyclopentyl)-2-hydroxy-2-phenylethanoate To a solution of 41 mg of 3-(benzyl(methyl)amino)propyl (2R)-2-((1R)-3,3-difluorocyclopentyl)-2-hydroxy-2-phenylethanoate in 2 ml of methanol, 10 mg of palladium hydroxide-carbon catalyst was added, followed by 2 hours' stirring at ambient temperature and pressure in hydrogen atmosphere. The reaction liquid was filtered with Celite. Distilling the solvent off from the filtrate under reduced pressure, 32 mg of the title compound was obtained.

Referential Example 43

4-Aminobutyl(2R)-2-((1R)-3,3-difluorocyclopentyl)-2-hydroxy-2-phenylethanoate

Using t-butyl 4-hydroxybutylcarbamate, the title compound was prepared by a method similar to Steps 2 and 3 of Referential Example 12.

Referential Example 44

1,4-Trans-4-aminocyclohexyl(2R)-2-((1R)-3,3-difluorocyclopentyl)-2-hydroxy-2-phenylethanoate
Using t-butyl N-(trans-4-hydroxycyclohexyl)carbamate (cf. WO9424093), the title compound was prepared by a method similar to Steps 2 and 3 of Referential Example 12.

Referential Example 45

1,4-Cis-4-aminocyclohexyl(2R)-2-((1R)-3,3-difluorocyclopentyl)-2-hydroxy-2-phenylethanoate Using t-butyl N-(cis-4-hydroxycyclohexyl)carbamate (cf. WO9424093), the title compound was prepared by a method similar to Steps 2 and 3 of Referential Example 12.

Referential Example 46

1,3-Ttrans-3-aminocyclobutyl(2R)-2-((1R)-3,3-difluorocyclopentyl)-2-hydroxy-2-phenylethanoate Using t-butyl N-(trans-3-hydroxycyclobutyl)carbamate (cf. WO9424093), the title compound was prepared by a method similar to Steps 2 and 3 of Referential Example 12.

Referential Example 47

1,3-Cis-3-aminocyclobutyl(2R)-2-((1R)-3,3-difluorocyclopentyl)-2-hydroxy-2-phenylethanoate Using t-butyl N-(cis-3-hydroxycyclobutyl)carbamate (cf. WO9424093), the title compound was prepared by a method similar to Steps 2 and 3 of Referential Example 12.

Referential Example 48

(1S,4S)-4-amino-2-cyclopentenyl(2R)-2-((1R)-3,3-difluorocyclopentyl)-2-hydroxy-2-phenylethanoate Using t-butyl N-((1S,4S)-4-hydroxy-2-cyclopentenyl)-carbamate (cf. *Journal of Medicinal Chemistry*, Vol.35, 3196 (1992), the title compound was prepared by a method similar to Steps 2 and 3 of Referential Example 12.

Referential Example 49

(1R,3R)-3-aminocyclopentyl(2R)-2-((1R)-3,3-difluorocyclopentyl)-2-hydroxy-2-phenylethanoate (Step 1)

Synthesis of t-butyl (1R,3R)-3-((2R)-2-((1R)-3,3-difluorocyclopentane)-2-hydroxy-2-phenylethanoyloxy) cyclopentyl-1-carboxylate To a solution of 66 mg of the t-butyl (1R,3R)-3-((2R)-2-((1R)-3,3-difluorocyclopentyl)-2-hydroxy-2- phenylethanoyloxy)-2-cyclopentenyl-1-carboxylate as obtained in Referential Example 48 in 2 ml of methanol, 10 mg of palladium-on-carbon catalyst was added, followed by an hour's stirring at ambient temperature and pressure in hydrogen atmosphere. The reaction liquid was filtered with Celite. Distilling the solvent off under reduced pressure, 28 mg of the title compound was obtained.
(Step 2)
Synthesis of (1R,3R)-3-aminocyclopentyl(2R)-2-((1R)-3, 3-difluorocyclopentyl)-2-hydroxy-2-phenylethanoate Using t-butyl (1R,3R)-3-((2R)-2-((1R)-3,3-difluorocyclopentyl)-2-hydroxy-2-phenylethanoyloxy) cyclopentane-1-carboxylate, the title compound was prepared by a method similar to Step 3 of Referential Example 12.

Referential Example 50

Piperidin-4-yl(2R)-((1R)-3,3-difluorocyclopentyl)-2-hydroxy-2-(4-fluorophenyl)ethanoate Using (2R)-2-((1R)-3,3-difluorocyclopentyl)-2-hydroxy-2-(4-fluorophenyl)acetic acid, the title compound was prepared by a method similar to Steps 2 and 3 of Referential Example 12.

Referential Example 51

Piperidin-4-yl(2R)-((1R)-3,3-difluorocyclopentyl)-2-hydroxy-2-(4-chlorophenyl)ethanoate Using (2R)-2-((1R)-3,3-difluorocyclopentyl)-2-hydroxy-2-(4-chlorophenyl)acetic acid, the title compound was prepared by a method similar to Steps 2 and 3 of Referential Example 12.

Referential Example 52

Piperidin-4-yl(2R)-((1R)-3,3-difluorocyclopentyl)-2-hydroxy-2-(4-bromophenyl)ethanoate Using (2R)-2-((1R)-3,3-difluorocyclopentyl)-2-hydroxy-2-(4-bromophenyl)acetic acid, the title compound was prepared by a method similar to Steps 2 and 3 of Referential Example 12.

Referential Example 53

Piperidin-4-yl(2R)-((1R)-3,3-difluorocyclopentyl)-2-hydroxy-2-(2,4-difluorophenyl)ethanoate Using (2R)-2-((1R)-3,3-difluorocyclopentyl)-2-hydroxy-2-(2,4-difluorophenyl)acetic acid, the title compound was prepared by a method similar to Steps 2 and 3 of Referential Example 12.

Referential Example 54

Piperidin-4-yl(2R)-((1R)-3,3-difluorocyclopentyl)-2-hydroxy-2-(2-chlorophenyl)ethanoate Using (2R)-2-((1R)-3,3-difluorocyclopentyl)-2-hydroxy-2-(2-chlorophenyl)acetic acid, the title compound was prepared by a method similar to Steps 2 and 3 of Referential Example 12.

Referential Example 55

Piperidin-4-yl(2R)-((1R)-3,3-difluorocyclopentyl)-2-hydroxy-2-(1,3-benzodioxol-5-yl)ethanoate Using (2R)-2-((1R)-3,3-difluorocyclopentyl)-2-hydroxy-2-(1,3-benzodioxol-5-yl)acetic acid, the title compound was prepared by a method similar to Steps 2 and 3 of Referential Example 12.

Referential Example 56

Piperidin-4-yl(2R)-((1R)-3,3-difluorocyclopentyl)-2-hydroxy-2-(4-vinylphenyl)ethanoate
(Step 1)
Synthesis of t-butyl 4-((2R)-2-((1R)-3,3-difluorocyclopentyl)-2-hydroxy-2-(4-vinylphenyl) ethanoyloxy)tetrahydropyridine-1(2H)-carboxylate To a solution of 125 mg of the t-butyl 4-((2R)-2-((1R)-3,3-difluorocyclopentyl)-2-hydroxy-2-(4-bromophenyl) ethanoyloxy)-tetrahydropyridine-1(2H)-carboxylate as obtained in Referential Example 52 in 4 ml of dioxane, 0.10 ml of vinyl tri-n-butyltin and 20 mg of tetrakistriphenylpalladium were added at room temperature, followed by 24 hours' heating under reflux at 110° C. in nitrogen atmosphere. Distilling the solvent off under reduced pressure, the resulting residue was diluted with ethyl acetate, washed successively with water and saturated brine, and dried over anhydrous sodium sulfate. Distilling the solvent off under reduced pressure, the residue was purified on silica gel column chromatography (eluent: hexane/ethyl acetate=4/1) to provide 90 mg of the title compound.
(Step 2)
Using t-butyl 4-((2R)-2-((1R)-3,3-difluorocyclopentyl)-2-hydroxy-2-(4-vinylphenyl)ethanoyloxy) tetrahydropyridine-1(2H)-carboxylate, the title compound was prepared by a method similar to Step 3 of Referential Example 12.

Referential Example 57

Piperidin-4-yl(2R)-((1R)-3,3-difluorocyclopentyl)-2-hydroxy-2-(4-ethylphenyl)ethanoate
(Step 1)
Synthesis of t-butyl 4-((2R)-2-((1R)-3,3-difluorocyclopentyl)-2-hydroxy-2-(4-ethylphenyl) ethanoyloxy)tetrahydropyridine-1(2H)-carboxylate To a solution of 50 mg of the t-butyl 4-((2R)-2-((1R)-3, 3-difluorocyclopentyl)-2-hydroxy-2-(4-vinylphenyl) ethanoyloxy)-tetrahydropyridine-1(2H)-carboxylate as obtained in Referential Example 56 in 3 ml of methanol, 10 mg of palladium-on-carbon catalyst was added, followed by 6 hours' stirring at ambient temperature and pressure in hydrogen atmosphere. The reaction liquid was filtered with Celite, and the solvent was distilled off under reduced pressure to provide the title compound.
(Step 2)
Using t-butyl 4-((2R)-2-((1R)-3,3-difluorocyclopentyl)-2-hydroxy-2-(4-ethylphenyl)ethanoyloxy) tetrahydropyridine-1(2H)-carboxylate, the title compound was obtained by a method similar to Step 3 of Referential Example 12.

Referential Example 58

Piperidin-4-yl(2R)-((1R)-3,3-difluorocyclopentyl)-2-hydroxy-2-(4-methylphenyl)ethanoate
(Step 1)
Synthesis of t-butyl 4-((2R)-2-((1R)-3,3-difluorocyclopentyl)-2-hydroxy-2-(4-(hydroxymethyl) phenyl)ethanoyloxy)tetrahydropyridine-1(2H)-carboxylate To a solution of 69 mg of the t-butyl 4-((2R)-2-((1R)-3, 3-difluorocyclopentyl)-2-hydroxy-2-(4-vinylphenyl) ethanoyloxy)-tetrahydropyridine-1(2H)-carboxylate as obtained in Referential Example 56 in 2 ml of tetrahydrofuran-water (1:1), 85 mg of sodium periodide and 0.1 ml of 2% osmium tetraoxide were added at 0° C., followed by an hour's stirring at the same temperature. Adding sodium sulfite to the reaction liquid, stirring was continued for further 30 minutes. The reaction liquid was diluted with ethyl acetate, washed successively with water and saturated brine, and dried over anhydrous sodium sulfate. Distilling the solvent off under reduced pressure, the residue was dissolved in 1 ml of methanol. To the solution 10 mg of sodium borohydride was added, stirred for 10 minutes and acetone was added. The reaction liquid was diluted with ethyl acetate, washed successively with water and saturated brine, and dried over anhydrous sodium sulfate. Distilling the solvent off under reduced pressure, the resulting residue was purified on preparative thin layer chromatography (Kieselgel™60F$_{254}$, Art 5744 (Merck), hexane/ethyl acetate=1/1) to provide 42 mg of the title compound as a colorless oily substance.

(Step 2)

Synthesis of t-butyl 4-((2R)-2-((1R)-3,3-difluorocyclopentyl)-2-hydroxy-2-(4-((acetyloxy)methyl)phenyl)ethanoyloxy)tetrahydropyridine-1(2H)-carboxylate To a solution of 42 mg of t-butyl 4-((2R)-2-((1R)-3,3-difluorocyclopentyl)-2-hydroxy-2-(4-(hydroxymethyl)phenyl)-ethanoyloxy)tetrahydropyridine-1(2H)-carboxylate in 2 ml of chloroform, 0.015 ml of triethylamine, 0.01 ml of acetic anhydride and 2 mg of dimethylaminopyridine were added successively, followed by an hour's stirring at room temperature. The reaction liquid was diluted with ethyl acetate, washed successively with water and saturated brine, and dried over anhydrous sodium sulfate. Distilling the solvent off under reduced pressure, the resulting residue was purified on preparative thin layer chromatography (Kieselgel™ 60F$_{254}$, Art 5744 (Merck), hexane/ethyl acetate=2/1) to provide 42 mg of the title compound as a colorless oily substance.

(Step 3)

Synthesis of t-butyl 4-((2R)-2-((1R)-3,3-difluorocyclopentyl)-2-hydroxy-2-(4-methylphenyl)ethanoyloxy)tetrahydropyridine-1(2H)-carboxylate To a solution of 42 mg of t-butyl 4-((2R)-2-((1R)-3,3-difluorocyclopentyl)-2-hydroxy-2-(4-((acetyloxy)methyl)phenyl)-ethanoyloxy)tetrahydropyridine-1(2H)-carboxylate in 1 ml of methanol, 20 mg of palladium hydroxide-carbon catalyst was added, followed by 16 hours' stirring at ambient temperature and pressure in hydrogen atmosphere. The reaction liquid was filtered with Celite and the solvent was distilled off under reduced pressure to provide 37 mg of the title compound.

(Step 4)

Synthesis of piperidin-4-yl(2R)-((1R)-3,3-difluorocyclopentyl)-2-hydroxy-2-(4-methylphenyl)ethanoate Using t-butyl 4-((2R)-2-((1R)-3,3-difluorocyclopentyl)-2-hydroxy-2-(4-methylphenyl)ethanoyloxy)tetrahydropyridine-1(2H)-carboxylate, the title compound was obtained by a method similar to Step 3 of Referential Example 12.

Referential Example 59

Piperidin-4-ylmethyl(2R)-2-((1R)-3,3-difluorocyclopentyl)-2-hydroxy-2-(4-chlorophenyl)ethanoate Using (2R)-2-((1R)-3,3-difluorocyclopentyl)-2-hydroxy-2-(4-chlorophenyl)acetic acid and N-t-butoxycarbonyl-4-piperidine-methanol, the title compound was prepared by a method similar to Steps 2 and 3 of Referential Example 12.

Referential Example 60

Piperidin-4-ylmethyl(2R)-2-((1R)-3,3-difluorocyclopentyl)-2-hydroxy-2-(4-bromophenyl)ethanoate Using (2R)-2-((1R)-3,3-difluorocyclopentyl)-2-hydroxy-2-(4-bromophenyl)acetic acid and N-t-butoxycarbonyl-4-piperidine-methanol, the title compound was prepared by a method similar to Steps 2 and 3 of Referential Example 12.

Referential Example 61

Piperidin-4-ylmethyl(2R)-2-((1R)-3,3-difluorocyclopentyl)-2-hydroxy-2-(4-vinylphenyl)ethanoate Using the t-butyl 4-(((2R)-2-((1R)-3,3-difluorocyclopentyl)-2-hydroxy-2-(4-bromophenyl)ethanoyloxy)methyl)tetrahydropyridine-1-(2H)-carboxylate as obtained in Referential Example 60, the title compound was prepared by a method similar to Referential Example 56.

Referential Example 62

Piperidin-4-ylmethyl(2R)-2-((1R)-3,3-difluorocyclopentyl)-2-hydroxy-2-(4-methylphenyl)ethanoate Using the t-butyl 4-(((2R)-2-((1R)-3,3-difluorocyclopentyl)-2-hydroxy-2-(4-vinylphenyl)ethanoyloxy)methyl)tetrahydropyridine-1-(2H)-carboxylate as obtained in Referential Example 61, the title compound was prepared by a method similar to Referential Example 58.

Referential Example 63

Piperidin-4-ylmethyl(2R)-2-((1R)-3,3-difluorocyclopentyl)-2-hydroxy-2-(4-ethylphenyl)ethanoate Using the t-butyl 4-(((2R)-2-((1R)-3,3-difluorocyclopentyl)-2-hydroxy-2-(4-vinylphenyl)ethanoyloxy)methyl)tetrahydropyridine-1-(2H)-carboxylate as obtained in Referential Example 61, the title compound was prepared by a method similar to Referential Example 57.

Referential Example 64

Piperidin-4-ylmethyl(2R)-2-((1R,4R)-3,3-difluoro-4-hydroxycyclopentyl)-2-hydroxy-2-phenylethanoate Using (2R)-2-((1R,4R)-3,3-difluoro-4-hydroxycyclopentyl)-2-hydroxy-2-phenylacetic acid and N-t-butoxycarbonyl-4-piperidine-methanol, the title compound was prepared by a method similar to steps 2 and 3 of Referential Example 12.

Referential Example 65

2-(Piperidin-4-yl)ethyl(2R)-((1R)-3,3-difluorocyclopentyl)-2-hydroxy-2-(4-chlorophenyl)ethanoate Using (2R)-2-((1R)-3,3-difluorocyclopentyl)-2-hydroxy-2-(4-chlorophenyl)acetic acid and t-butyl 4-(2-hydroxyethyl)tetrahydropyridine-1(2H)-carboxylate, the title compound was prepared by a method similar to steps 2 and 3 of Referential Example 12.

Referential Example 66

2-(Piperidin-4-yl)ethyl(2R)-((1R)-3,3-difluorocyclopentyl)-2-hydroxy-2-(4-bromophenyl)ethanoate Using (2R)-2-((1R)-3,3-difluorocyclopentyl)-2-hydroxy-2-(4-bromophenyl)acetic acid and t-butyl 4-(2-hydroxyethyl)tetrahydropyridine-1(2H)-carboxylate, the title compound was prepared by a method similar to steps 2 and 3 of Referential Example 12.

Referential Example 67

3-Endo-8-azabicyclo[3.2.1]oct-3-yl(2R)-2-((1R)-3,3-difluorocyclopentyl)-2-hydroxy-2-(4-chlorophenyl)ethanoate Using (2R)-2-((1R)-3,3-difluorocyclopentyl)-2-hydroxy-2-(4-chlorophenyl)acetic acid and t-butyl 3-endo-3-hydroxy-8-azabicyclo-[3.2.1]octane-8-carboxylate, the title compound was prepared by a method similar to steps 2 and 3 of Referential Example 12.

Referential Example 68

3-Endo-8-azabicyclo[3.2.1]oct-3-yl(2R)-2-((1R)-3,3-difluorocyclopentyl)-2-hydroxy-2-(4-bromophenyl)ethanoate Using (2R)-2-((1R)-3,3-difluorocyclopentyl)-2-hydroxy-2-(4-bromophenyl)acetic acid and t-butyl 3-endo-3-hydroxy-8-azabicyclo-[3.2.1]octane-8-carboxylate, the title compound was prepared by a method similar to steps 2 and 3 of Referential Example 12.

Referential Example 69

3-Endo-8-azabicyclo[3.2.1]oct-3-yl(2R)-2-((1R)-3,3-difluorocyclopentyl)-2-hydroxy-2-(2,4-difluorophenyl)ethanoate Using (2R)-2-((1R)-3,3-difluorocyclopentyl)-2-hydroxy-2-(2,4-difluorophenyl)acetic acid and t-butyl 3-endo-3-hydroxy-8-azabicyclo[3.2.1]octane-8-carboxylate, the title compound was prepared by a method similar to steps 2 and 3 of Referential Example 12.

Referential Example 70

(3R)-pyrrolidin-3-yl(2R)-2-((1R)-3,3-difluorocyclopentyl)-2-hydroxy-2-(4-fluorophenyl)ethanoate Using (2R)-2-((1R)-3,3-difluorocyclopentyl)-2-hydroxy-2-(4-fluorophenyl)acetic acid and t-butyl(3R)-3-hydroxypyrrolidine-1-carboxylate, the title compound was prepared by a method similar to Steps 2 and 3 of Referential Example 12.

Referential Example 71

(3R)-pyrrolidin-3-yl(2R)-2-((1R)-3,3-difluorocyclopentyl)-2-hydroxy-2-(4-chlorophenyl)ethanoate Using (2R)-2-((1R)-3,3-difluorocyclopentyl)-2-hydroxy-2-(4-chlorophenyl)acetic acid and t-butyl(3R)-3-hydroxypyrrolidine-1-carboxylate, the title compound was prepared by a method similar to Steps 2 and 3 of Referential Example 12.

Referential Example 72

(3R)-pyrrolidin-3-yl(2R)-2-((1R)-3,3-difluorocyclopentyl)-2-hydroxy-2-(4-bromophenyl)ethanoate Using (2R)-2-((1R)-3,3-difluorocyclopentyl)-2-hydroxy-2-(4-bromophenyl)acetic acid and t-butyl(3R)-3-hydroxypyrrolidine-1-carboxylate, the title compound was prepared by a method similar to Steps 2 and 3 of Referential Example 12.

Referential Example 73

(3R)-pyrrolidin-3-yl(2R)-2-((1R)-3,3-difluorocyclopentyl)-2-hydroxy-2-(4-methylphenyl)ethanoate Using the t-butyl (3R)-3-(((2R)-2-((1R)-3,3-difluorocyclopentyl)-2-hydroxy-2-(4-bromophenyl)ethanoyl)oxy)-pyrrolidine-1-carboxylate as obtained in Referential Example 72, the title compound was synthesized by a method similar to Step 1 of Referential Example 56 and Referential Example 57.

Referential Example 74

(3S)-pyrrolidin-3-yl(2R)-2-((1R)-3,3-difluorocyclopentyl)-2-hydroxy-2-(4-fluorophenyl)ethanoate Using(2R)-2-((1R)-3,3-difluorocyclopentyl)-2-hydroxy-2-(4-fluorophenyl)acetic acid and t-butyl(3S)-3-hydroxypyrrolidine-1-carboxylate, the title compound was prepared by a method similar to Steps 2 and 3 of Referential Example 12.

Referential Example 75

(3S)-pyrrolidin-3-yl(2R)-2-((1R)-3,3-difluorocyclopentyl)-2-hydroxy-2-(4-chlorophenyl)ethanoate Using(2R)-2-((1R)-3,3-difluorocyclopentyl)-2-hydroxy-2-(4-chlorophenyl)acetic acid and t-butyl(3S)-3-hydroxypyrrolidine-1-carboxylate, the title compound was prepared by a method similar to Steps 2 and 3 of Referential Example 12.

Referential Example 76

(3S)-pyrrolidin-3-yl(2R)-2-((1R)-3,3-difluorocyclopentyl)-2-hydroxy-2-(4-bromophenyl)ethanoate Using (2R)-2-((1R)-3,3-difluorocyclopentyl)-2-hydroxy-2-(4-bromophenyl)acetic acid and t-butyl(3S)-3-hydroxypyrrolidine-1-carboxylate, the title compound was prepared by a method similar to Steps 2 and 3 of Referential Example 12.

Referential Example 77

((4S)-2-thioxohexahydropyrimidin-4-yl)methyl(2R)-2-((1R)-3,3-difluorocyclopentyl)-2-hydroxy-2-phenylethanoate
(Step 1)
Synthesis of 2-((4R)-2,2-dimethyl-1,3-dioxolan-4-yl)ethan-1-ol To a solution of 1.0 g of methyl 2-((4R)-2,2-dimethyl-1,3-dioxolan-4-yl)acetate in 29 ml of diethyl ether, 110 mg of lithium aluminum hydride was added under cooling with ice, followed by 12 hours' stirring at the same temperature. Sodium sulfate decahydrate was added to the reaction liquid which was then stirred for 30 minutes and filtered with Celite. Distilling the solvent off under reduced pressure, 782 mg of the title compound was obtained.
(Step 2)
Synthesis of 1,2-((4R)-2,2-dimethyl-1,3-dioxolan-4-yl)-ethylazide To a solution of 782 mg of 2-((4R)-2,2-dimethyl-1,3-dioxolan-4-yl)ethan-1-ol in 21 ml of ethyl acetate, 1.5 ml of triethylamine and 643 mg of methanesulfonyl chloride were added, followed by 30 minutes' stirring at room temperature. The reaction liquid was diluted with ethyl acetate, washed successively with saturated aqueous sodium hydrogencarbonate solution and saturated brine, and dried over anhydrous sodium sulfate. Distilling the solvent off under reduced pressure, the residue was dissolved in 25 ml of dimethylformamide. To the solution 670 mg of sodium azide was added, followed by 12 hours' stirring at 90° C. The reaction liquid was diluted with ethyl acetate, washed successively with saturated aqueous ammonium chloride solution and saturated brine, and dried over anhydrous magnesium sulfate. Distilling the solvent off under reduced pressure, the resulting residue was purified on silica gel column chromatography (eluent: hexane/ethyl acetate=5/1) to provide 702 mg of the title compound.

(Step 3)

Synthesis of 1-((3R)-4-t-butyl(dimethyl)silyl)oxy-3-hydroxybutyl)azide

To a solution of 2.2 g of 1,2-((4R)-2,2-dimethyl-1,3-dioxolan-4-yl)-ethylazide in 15 ml of tetrahydrofuran, 6 ml of 2N hydrochloric acid was added, followed by 2 hours' stirring at room temperature. Distilling the solvent off under reduced pressure, the resulting residue was dissolved in 25 ml of dimethylformamide. To the solution 2.0 g of t-butyldimethylsilylchloride and 1.8 g of imidazole were added, followed by 19 hours' stirring at room temperature. The reaction liquid was diluted with ethyl acetate, washed successively with water and saturated brine, and dried over anhydrous sodium sulfate. Distilling the solvent off under reduced pressure, the resulting residue was purified on silica gel column chromatography (eluent: hexane/ethyl acetate= 30/1) to provide 1.6 g of the title compound.

(Step 4)

Synthesis of 1-((1S)-1-((t-butyl(dimethyl)silyl) oxymethyl)-3-triaza-1,2-dien-2-iumylpropyl)azide Using 1-((3R)-4-t-butyl(dimethyl)silyl)oxy-3-hydroxybutyl)azide, the title compound was prepared by a method similar to the method of Step 2.

(Step 5)

Synthesis of (3S)-4-(t-butyl(dimethyl)silyl)oxybutane-1,3-diamine

To a solution of 379 mg of 1-((1S)-1-((t-butyl(dimethyl)silyl)-oxymethyl)-3-triaza-1,2-dien-2-iumylpropyl)azide in 8 ml of methanol, 80 mg of 10% palladium-on-carbon catalyst was added, and stirred for an hour in hydrogen atmosphere. Filtering the catalyst off, the solvent was distilled off under reduced pressure to provide 306 mg of the title compound.

(Step 6)

Synthesis of (4S)-4-(hydroxymethyl) tetrahydropyrimidine-2(1H)-thione

To a solution of 98 mg of (3S)-4-(t-butyl(dimethyl)silyl)-oxybutane-1,3-diamine in 20 ml of acetonitrile, 65 mg of tetramethylthiuram monosulfide was added, followed by 6 hours' heating under reflux. Distilling the solvent off under reduced pressure, the resulting residue was purified on silica gel column chromatography (eluent: hexane/ethyl acetate= 1/1). The product was dissolved in 2 ml of tetrahydrofuran, and to the solution 0.16 ml of 1.0M tetrahydrofuran solution of tetrabutylammonium fluoride was added, followed by an hour's standing at room temperature. The reaction liquid was diluted with ethyl acetate, washed successively with water and saturated brine, and dried over anhydrous sodium sulfate. Distililng the solvent off under reduced pressure, 51 mg of the title compound was obtained.

(Step 7)

Synthesis of ((4S)-2-thioxohexahydropyrimidin-4-yl) methyl(2R)-2-((1R)-3,3-difluorocyclopentyl)-2-hydroxy-2-phenylethanoate Using (2R)-2-((1R)-3,3-difluorocyclopentyl)-2-hydroxy-2-phenylacetic acid and (4S)-4-(hydroxymethyl) tetrahydropyrimidine-2(1H)-thione, the title compound was prepared by a method similar to Step 2 of Referential Example 12.

Referential Example 78

((4R)-2-thioxohexahydropyrimidin-4-yl)methyl(2R)-2-((1R)-3,3-difluorocyclopentyl)-2-hydroxy-2-phenylethanoate Using methyl 2-((4S)-2,2-dimethyl-1,3-dioxolan-4-yl) acetate, the title compound was prepared by a method similar to Referential Example 77.

Referential Example 79

2-Thioxohexahydropyrimidin-5-yl(2R)-2-((1R)-3,3-difluorocyclopentyl)-2-hydroxy-2-phenylethanoate Using (2R)-2-((1R)-3,3-difluorocyclopentyl)-2-hydroxy-2-phenylacetic acid and 5-hydroxytetrahydropyrimidine-2 (1H)-thion (cf. JP-Hei01 (1989)-128970A), the title compound was prepared by a method similar to Step 2 of Referential Example 12.

Formulation Example 1

The compound of Example 1, 0.1 g, was dissolved in 900 ml of isotonic sodium chloride solution. Further isotonic sodium chloride solution was added to make the total amount 1000 ml, and the solution was given a sterile filtration through a membrane filter of 0.25 µm in pore size. One (1) ml each of the solution was poured in sterilized ampoules to provide a liquid inhalant.

Formulation Example 2

Ten (10) g of the compound of Example 1 was homogeneously mixed with 70 g of lactose, and 100 mg of the mixed powder was filled in an exclusive powder inhaler, to provide a powder inhalant (400 µg per inhalation).

INDUSTRIAL APPLICABILITY

Because those compounds of the present invention exhibit selective antagonism to muscarine $M_3$ receptors, they have little side effect and are safe. They exhibit excellent pharmacological effect and prolonged action also in inhalation therapy, and hence are useful as treating agents for diseases of respiratory organs.

What is claimed is:

1. A compound which is represented by the following general formula (I):

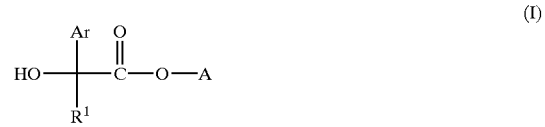

wherein A is a 6-membered single nitrogen-containing ring having:

(i) the formula ($a_1$):

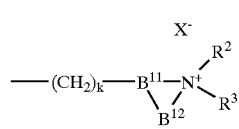

wherein $B^{11}$ and $B^{12}$ signify, independently of each other, a $C_1$–$C_6$ saturated or unsaturated aliphatic hydrocarbon group; k signifies 0, 1 or 2; $R^2$ and $R^3$ signify, either independently of each other, an optionally phenyl-substituted lower alkyl; and $X^-$ signifies an anion, provided that the sum of carbon atoms of $B^{11}$ and $B^{12}$ and k does not exceed 13; or (ii) the formula ($a_{p1}$):

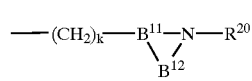

wherein $B^{11}$ and $B^{12}$ signify, independently of each other, $C_1$–$C_6$ saturated or unsaturated aliphatic hydrocarbon; k signifies 0, 1 or 2; $R^{20}$ signifies hydrogen or a lower alkyl optionally having substituent(s) selected from a group consisting of phenyl and cycloalkyl, provided that the sum of carbon atoms of $B^{11}$ and $B^{12}$ and k does not exceed 13; or (iii) the formula ($b_1$):

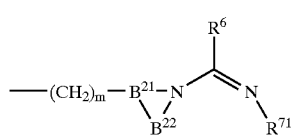

wherein $B^{21}$ and $B^{22}$ signify, independently of each other, a $C_1$–$C_6$ saturated or unsaturated aliphatic hydrocarbon group; m signifies 0, 1 or 2; $R^6$ signifies hydrogen, lower alkyl or a group represented by —$N(R^8)R^9$; $R^8$ and $R^9$ signify, independently of each other, hydrogen or lower alkyl; and $R^{71}$ signifies hydrogen or lower alkyl, provided that the sum of carbon atoms of $B^{21}$ and $B^{22}$ and m does not exceed 13; or (iv) the formula ($b_{p1}$):

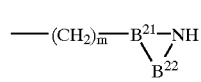

wherein $B^{21}$ and $B^{22}$ signify, independently of each other, $C_1$–$C_6$ saturated or unsaturated aliphatic hydrocarbon; m signifies 0, 1 or 2, provided that the sum of carbon atoms of $B^{21}$ and $B^{22}$ and m does not exceed 13;

Ar is phenyl optionally having substituent(s) selected from the group consisting of halogen, lower alkyl, lower alkenyl and lower alkoxy; and $R^1$ is a fluorine-substituted $C_4$–$C_6$ cycloalkyl optionally having hydroxyl group(s);

or a pharmaceutically acceptable salt thereof.

2. The compound according to claim 1, in which A is a group represented by one of the formula ($a_2$):

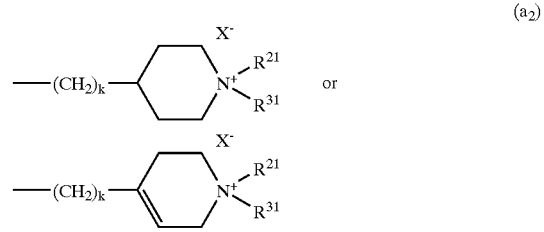

wherein k signifies 0, 1 or 2; $R^{21}$ and $R^{31}$ signify, independently of each other, a lower alkyl; and $X^-$ signifies an anion.

3. The compound according to claim 2, in which $R^1$ is fluorine-substituted cyclopentyl group.

4. The compound according to claim 3, in which $R^1$ is 3,3-difluorocyclopentyl group.

5. The compound according to claim 2, in which k is 0.

6. The compound according to claim 2, in which both $R^{21}$ and $R^{31}$ are methyl.

7. The compound according to claim 2, in which Ar is a phenyl having a substituent selected from the group consisting of halogen, lower alkyl, lower alkenyl and lower alkoxy.

8. The compound according to claim 7, in which Ar is 4-chlorophenyl.

9. The compound according to claim 1, in which A is a group represented by the formula ($a_3$):

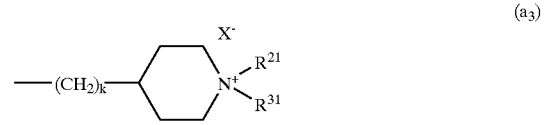

wherein k signifies 0, 1 or 2; $R^{21}$ and $R^{31}$ signify, independently of each other, a lower alkyl; and $X^-$ signifies an anion.

10. The compound according to claim 1, in which A is a group represented by one of the following formula ($b_2$):

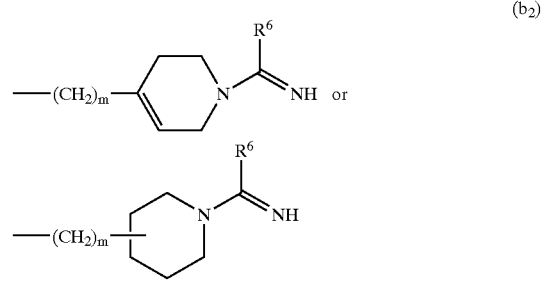

in which m signifies 0, 1 or 2; $R^6$ signifies hydrogen, lower alkyl or a group represented by —$N(R^8)R^9$; and $R^8$ and $R^9$ signify, independently of each other, hydrogen or lower alkyl.

11. The compound according to claim 10, in which $R^1$ is fluorine-substituted cyclopentyl group.

12. The compound according to claim 11, in which $R^1$ is 3,3-difluorocyclopentyl group.

13. The compound according to claim 10, in which m is 1 or 2.

14. The compound according to claim 10, in which $R^6$ is hydrogen.

15. The compound according to claim 10, in which Ar is unsubstituted phenyl.

16. The compound according to claim 1, in which A is a group represented by the formula (b₃):

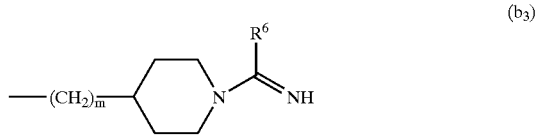

in which m signifies 0, 1 or 2; $R^6$ signifies hydrogen, lower alkyl or a group represented by —$N(R^8)R^9$; and $R^8$ and $R^9$ signify, independently of each other, hydrogen or lower alkyl.

17. The compound according to claim 1, in which A is a group represented by one of the formula (a_{p2}):

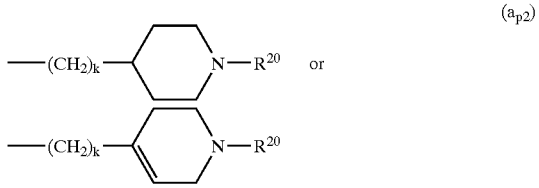

in which k signifies 0, 1 or 2; and $R^{20}$ signifies hydrogen or a lower alkyl optionally having substituent(s) selected from a group consisting of phenyl and cycloalkyl.

18. The compound according to claim 17, in which $R^1$ is a fluorine-substituted cyclopentyl group.

19. The compound according to claim 18, in which $R^1$ is 3,3-difluorocyclopentyl group.

20. The compounds according to claim 17, in which A is a group represented by a formula (a_{p3}):

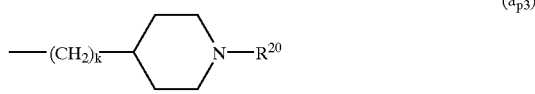

in which k signifies 0, 1 or 2; and $R^{20}$ signifies hydrogen or a lower alkyl optionally having substituent(s) selected from a group consisting of phenyl and cycloalkyl.

21. The compound according to claim 17, in which k is 0.

22. The compound according to claim 17, in which Ar is phenyl which has substituent(s) selected from a group consisting of halogen, lower alkyl, lower alkenyl and lower alkoxy.

23. The compound according to claim 22, in which Ar is 4-chlorophenyl.

24. The compound according to claim 1, in which A is represented by one of the following formulae (b_{p2}):

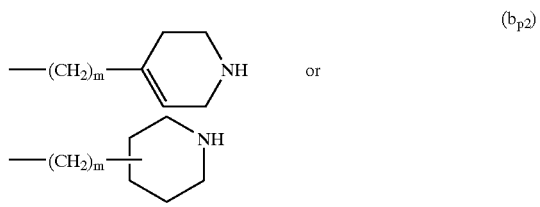

in which m signifies 0, 1 or 2.

25. The compound according to claim 24, in which $R^1$ is a fluorine-substituted cyclopentyl group.

26. The compound according to claim 25, in which $R^1$ is 3,3-difluorocyclopentyl group.

27. The compound according to claim 24, in which A is represented by the formula (b_{p3}):

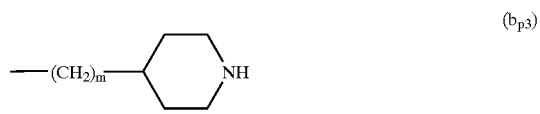

in which m signifies 0, 1 or 2.

28. The compound according to claim 24, in which m is 1 or 2.

29. The compound according to claim 24, in which Ar is unsubstituted phenyl.

30. A pharmaceutical composition comprising the compound according to claim 1, or a pharmaceutically acceptable salt thereof, together with a pharmaceutically acceptable adjuvant.

31. The composition according to claim 30, which is in the form of an inhalant.

32. A method for treating chronic obstructive pulmonary disease, chronic bronchitis, asthma, chronic respiratory tract obstruction, fibroid lung, pulmonary emphysema or rhinitis, which comprises administering a therapeutically effective amount of the compound according to claim 1 to a patient in need thereof.

* * * * *